(12) United States Patent
Nakata et al.

(10) Patent No.: US 9,117,475 B2
(45) Date of Patent: Aug. 25, 2015

(54) LUBRICANT COMPOSITION AND USE THEREOF

(75) Inventors: Hiyoku Nakata, Minami-ashigara (JP); Akiko Hattori, Minami-ashigara (JP); Atsushi Tatsugawa, Minami-ashigara (JP); Ken Kawata, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 643 days.

(21) Appl. No.: 13/260,155

(22) PCT Filed: Mar. 24, 2010

(86) PCT No.: PCT/JP2010/002055
§ 371 (c)(1),
(2), (4) Date: Sep. 23, 2011

(87) PCT Pub. No.: WO2010/109851
PCT Pub. Date: Sep. 30, 2010

(65) Prior Publication Data
US 2012/0021253 A1    Jan. 26, 2012

(30) Foreign Application Priority Data

Mar. 25, 2009 (JP) .................. 2009-074527
Sep. 18, 2009 (JP) .................. 2009-216679

(51) Int. Cl.
*C10M 105/50* (2006.01)
*G11B 5/725* (2006.01)
(Continued)

(52) U.S. Cl.
CPC .............. *G11B 5/725* (2013.01); *C07C 43/225* (2013.01); *C07C 43/23* (2013.01); *C07D 251/70* (2013.01);
(Continued)

(58) Field of Classification Search
CPC .............. C10M 107/38; C10M 147/00; C10M 147/04; C10M 2213/06
USPC ....................................................... 508/582
See application file for complete search history.

(56) References Cited

U.S. PATENT DOCUMENTS 5,374,480 A    12/1994  Nishikawa et al.
5,456,980 A    10/1995  Murakami et al.
(Continued)

FOREIGN PATENT DOCUMENTS

EP    1219629 A1    7/2002
EP    1295934 A1    3/2003
(Continued)

OTHER PUBLICATIONS

Paul H. Kasai, et al., "Degradation of perfluoropolyethers catalyzed by aluminum oxide", Applied Surface Science, 1991, pp. 201-211, vol. 51.
(Continued)

*Primary Examiner* — Taiwo Oladapo
(74) *Attorney, Agent, or Firm* — Sughrue Mion, PLLC

(57) ABSTRACT

[Problem] Provided is a novel lubricant composition that is useful as a material of a lubricating layer of a magnetic recording medium.
[Means for Resolution] The lubricant composition contains at least one kind of compound represented by the following Formula (1). In the formula, X represents a cyclic group that may be substituted, and Y represents a single bond or a linking group having a valency of 2 or more. Here, at least one of X and Y includes 1 or more polar groups such as a hydroxyl group; Z represents a linking group having a valency of 2 or more and constituted with a carbon atom (C), a fluorine atom (F), and 1 or 2 kinds of arbitrary atoms (here, a hydrogen atom is excluded); n represents a real number of 1 to 10; m represents a real number of 0 to 1; and s and t independently represent a real number of 1 or greater.

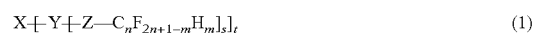

19 Claims, 2 Drawing Sheets

(51) Int. Cl.

| | | |
|---|---|---|
| C10M 147/04 | (2006.01) | |
| C07C 43/225 | (2006.01) | |
| C07C 43/23 | (2006.01) | |
| C07D 251/70 | (2006.01) | |
| C07D 401/14 | (2006.01) | |
| C07D 403/14 | (2006.01) | |
| C07D 405/14 | (2006.01) | |
| C07D 409/14 | (2006.01) | |
| C07D 413/12 | (2006.01) | |
| C07D 417/12 | (2006.01) | |
| C10M 105/70 | (2006.01) | |
| C10M 105/72 | (2006.01) | |
| C10M 133/42 | (2006.01) | |
| C23C 16/44 | (2006.01) | |
| B32B 9/00 | (2006.01) | |
| C10M 147/00 | (2006.01) | |
| B05D 3/12 | (2006.01) | |
| G11B 5/65 | (2006.01) | |
| C10M 107/38 | (2006.01) | |
| G11B 5/33 | (2006.01) | |
| C07D 251/54 | (2006.01) | |
| B05D 1/18 | (2006.01) | |
| C07D 225/00 | (2006.01) | |

(52) U.S. Cl.
CPC ............ *C07D 401/14* (2013.01); *C07D 403/14* (2013.01); *C07D 405/14* (2013.01); *C07D 409/14* (2013.01); *C07D 413/12* (2013.01); *C07D 417/12* (2013.01); *C10M 105/70* (2013.01); *C10M 105/72* (2013.01); *C10M 133/42* (2013.01); *C10M 147/04* (2013.01); *B05D 1/18* (2013.01); *B05D 3/12* (2013.01); *B32B 9/00* (2013.01); *C07D 225/00* (2013.01); *C07D 251/54* (2013.01); *C10M 107/38* (2013.01); *C10M 147/00* (2013.01); *C10M 2211/04* (2013.01); *C10M 2213/04* (2013.01); *C10M 2213/06* (2013.01); *C10M 2215/222* (2013.01); *C10M 2215/2225* (2013.01); *C10M 2223/083* (2013.01); *C10N 2240/204* (2013.01); *C23C 16/44* (2013.01); *G11B 5/33* (2013.01); *G11B 5/65* (2013.01); *Y10T 428/11* (2015.01); *Y10T 428/30* (2015.01)

(56) References Cited

U.S. PATENT DOCUMENTS

| | | | | |
|---|---|---|---|---|
| 5,536,578 | A | | 7/1996 | Shoji et al. |
| 5,663,127 | A | | 9/1997 | Flynn et al. |
| 6,559,108 | B1 | * | 5/2003 | Howell et al. ................ 508/427 |
| 6,608,009 | B2 | | 8/2003 | Akada et al. |
| 8,492,011 | B2 | | 7/2013 | Itoh et al. |
| 2002/0183211 | A1 | | 12/2002 | Akada et al. |
| 2003/0138670 | A1 | | 7/2003 | Liu et al. |
| 2003/0207774 | A1 | | 11/2003 | Negoro et al. |
| 2005/0277558 | A1 | * | 12/2005 | Deng et al. ................ 508/548 |
| 2006/0052262 | A1 | | 3/2006 | Akada et al. |
| 2007/0054814 | A1 | | 3/2007 | Negoro et al. |
| 2008/0194441 | A1 | * | 8/2008 | Kawata et al. ............... 508/208 |
| 2009/0143262 | A1 | | 6/2009 | Kawata |
| 2011/0015107 | A1 | | 1/2011 | Marchionni et al. |
| 2011/0026162 | A1 | | 2/2011 | Hamakubo et al. |
| 2012/0021253 | A1 | | 1/2012 | Nakata et al. |

FOREIGN PATENT DOCUMENTS

| | | | | |
|---|---|---|---|---|
| JP | 1-246237 | A | | 10/1989 |
| JP | 4-19816 | A | | 1/1992 |
| JP | 6-157471 | A | | 6/1994 |
| JP | 7-228575 | A | | 8/1995 |
| JP | 10-143838 | A | | 5/1998 |
| JP | 2001-184622 | A | | 7/2001 |
| JP | 2002-69472 | A | | 3/2002 |
| JP | 2003-192677 | A | | 7/2003 |
| JP | 2004-352999 | A | | 12/2004 |
| JP | 2006-257382 | A | | 9/2006 |
| JP | 2006257382 | A | * | 9/2006 |
| JP | 2006-307201 | A | | 11/2006 |
| JP | 2006-307202 | A | | 11/2006 |
| JP | 2007-92055 | A | | 4/2007 |
| JP | 2008-195799 | A | | 8/2008 |
| JP | 2008-214603 | A | | 9/2008 |
| JP | 2010-143855 | A | | 7/2010 |
| JP | 2010-248463 | A | | 11/2010 |
| WO | 01/21630 | A1 | | 3/2001 |
| WO | 2004/031261 | A1 | | 4/2004 |
| WO | 2008/096875 | A1 | | 8/2008 |
| WO | 2009/123037 | A1 | | 10/2009 |
| WO | 2010/109851 | A1 | | 9/2010 |

OTHER PUBLICATIONS

Ken Kawata, "Orientation Control and Fixation of Discotic Liquid Crystal", The Chemical Record, 2002, pp. 59-80, vol. 2.
Office Action dated Sep. 10, 2013 in Japanese Application No. 2011-048763.
English translation of International Preliminary Report on Patentability dated Oct. 27, 2011 in PCT/JP2010/002055.
International Preliminary Report on Patentability dated Oct. 6, 2011 in PCT/JP2010/002055.
Extended European Search Report dated Sep. 3, 2012 in European Patent Application No. 10755653.2.
Office Action dated Nov. 19, 2013 in Japanese Application No. 2009-216679.
Office Action dated Dec. 16, 2013 in U.S. Appl. No. 13/414,042.
Derwent Abstract Translation of WO 2010109851 A1 (published Sep. 2010).

* cited by examiner

LUBRICANT COMPOSITION AND USE THEREOF

CROSS REFERENCE TO RELATED APPLICATIONS

This application is a National Stage of International Application No. PCT/JP2010/002055, filed on Mar. 24, 2010, which claims priority from Japanese Patent Application Nos. 2009-074527, filed on Mar. 25, 2009 and 2009-216679 filed on Sept. 18, 2009, the contents of all of which are incorporated herein by reference in their entirety

TECHNICAL FIELD

The present invention relates to a lubricant composition that contains a compound having a substituent which includes a polar group and a fluorine atom. More specifically, the invention relates to a lubricant composition useful as a lubricant for a recording medium such as a magnetic disk and a magnetic tape as a mass-storage recording medium. In addition, the invention relates to various uses of the lubricant composition, and specifically to a film, a laminate, a magnetic recording medium, a head slider, and a magnetic recording device which are formed using the lubricant composition.

BACKGROUND ART

A thin film type magnetic recording medium is produced by forming a magnetic layer formed of a ferromagnetic metal or an alloy thereof on a nonmagnetic substrate by means of various methods (for example, sputtering, vapor deposition, and non-electrolytic plating). When practically used, the magnetic recording medium performs contact-slide with respect to a magnetic head at a high speed, so the medium suffers from abrasion damage or is caused to have deterioration of magnetic characteristics in some cases. Accordingly, a protective film and a lubricating layer are provided on the magnetic layer so as to improve abrasion resistance. Hitherto, as a material of the protective film layer, a carbonaceous film, an oxide film such as $SiO_2$, $ZrO_2$, a nitride film, a boride film, and the like have been generally used. In addition, as a material of the lubricating layer, a fluorine-based compound is generally used.

In this way, the lubricating layer of the recording medium is very useful for the purpose of reducing the abrasion damage and the deterioration of magnetic characteristics caused by the contact-slide that occurs between the head and the medium, by means of reducing a coefficient of kinetic friction. On the other hand, particularly, when the film thickness of the lubricating layer is large, adsorption easily occurs between the head and the disk in some cases due to the presence of the lubricating layer. Due to the adsorption, a coefficient of static friction increases, and the head sticks to the disk and does not operate any more in some cases. This adsorption occurs more easily as the medium substrate becomes smoother. In order to heighten surface recording density, it is required to keep the floating height of the head low and speed up the disk rotation. Therefore, since the surface of the medium substrate tends to be smoother, it is important to suppress the adsorption. On the other hand, if the film thickness of the lubricating layer is reduced, though the adsorption does not easily occur, the function of the lubricating layer, that is, the suppression of the abrasion damage and deterioration of the magnetic characteristics caused by the high-speed contact-slide cannot be accomplished in some cases.

Accordingly, various attempts for solving the above problem by carefully selecting a lubricant used for the lubricating layer have been made. For example, compounds disclosed in PTLs 1 and 2 and a lubricant "FOMBLIN Z-DOL" manufactured by Ausimont, Inc. have a $CH_2OH$ group at both terminals of a molecule. Therefore, if these are used, it is possible to impart an excellent sliding-resistance characteristic in which the lubricant strongly binds to the surface of the protective film layer.

However, as shown in NPL 1, since the "FOMBLIN Z-DOL" has a bond of an O—$CF_2$—O unit in a molecule, "FOMBLIN Z-DOL" is easily degraded at about 200° C. in the presence of aluminum oxide ($\alpha$-$Al_2O_3$) that is a constituent component of the magnetic head. In addition, at the time of CSS (contact start stop), there are instantaneous local temperature increases up to 90° C. to 450° C. or higher due to the contact between the magnetic recording medium and the magnetic head. Consequently, the aluminum oxide which is a constituent component of the slider portion of the magnetic head serves as a catalyst, and the "FOMBLIN Z-DOL" is degraded. If the lubricant is degraded in this way, the film thickness of the lubricating layer is reduced since the degraded component volatilizes, and the coefficient of kinetic friction increases. As a result, a problem that the abrasion damage and the deterioration of the magnetic characteristics caused by the high-speed contact-slide easily occur arises. Moreover, a part of the degraded component is attached to the magnetic head, which leads to a problem that reproduction output is reduced due to an increase in floating height of the head, and that the head is adsorbed onto the recording medium surface, for example. In this respect, there is a demand for a method that suppresses the contact degradation caused by the magnetic head while maintaining a high substrate-adsorptive property and sliding-resistance characteristic that are advantages of "FOMBLIN Z-DOL".

As one of the methods, there is a method of using a lubricant "FOMBLIN Z-TETRAOL" manufactured by Ausimont, Inc. having a $CH(OH)CH_2OH$ group at both terminals of a molecule. Though including a structure of the O—$CF_2$—O unit in a molecule as in "FOMBLIN Z-DOL", this lubricant is chemically stable since the contact reaction (degradation) to the aluminum oxide at the slider portion of the head is relieved due to a multidentate structure of a polar functional group. Moreover, the polar functional groups at both terminals have high affinity with a carbon-based or an oxide ceramics-based protective film, which contributes to the improvement of a spin-off property; therefore, "FOMBLIN Z-TETRAOL" has excellent stability.

However, since a large number of the polar functional groups having high affinity with the substrate are present at both terminals, a degree of freedom of the molecules in the lubricating layer is reduced. As a result, a lubricating property becomes insufficient, and the sliding durability deteriorates when "FOMBLIN Z-TETRAOL" is used in combination with a pseudo-contact type head.

In order to solve the above problem, a method of improving the lubricating property and maintaining durability by providing a lubricant component (non-substrate-adsorptive component) (hereinafter, a layer formed of the non-substrate-adsorptive component is referred to as a "non-adsorptive layer") that can freely move inside the lubricating layer is used (for example, PTL 3).

However, problems that the non-substrate-adsorptive component in the lubricating layer volatilizes easily, and that the reproduction output is reduced due to the increase in the floating height of the head since the non-adsorptive component is attached to the magnetic head when the magnetic head contacts the disk have been reported. In addition, since keeping the floating height of the head low will be promoted in the future to improve the surface recording density, and the lubricating layer is expected to become thinner, the non-adsorptive layer in the lubricating layer is assumed to go against this trend. Consequently, there is a demand for the development of a lubricant that enables the configuration to include only an adsorptive layer while maintaining the high substrate-adsorptive property, sliding-resistance characteristic, and high stability that are advantages of "FOMBLIN Z-TETRAOL".

Meanwhile, the use of a phosphazene compound, a lubricant composition containing the same, and the use of the lubricant composition as a lubricant for a recording medium have been proposed (PTLs 4 and 5). However, since the adsorptive property or the like of the phosphazene compound with respect to a substrate is insufficient, the phosphazene compound needs to be used in combination with a lubricant such as the FOMBLIN Z-TETRAOL.

Furthermore, various lubricant compositions using a polymer that includes a mesogen structure in a main chain or a side chain and grease compositions have been proposed (for example, Patent PTLs 6, 7, and 8), but whether these compositions are useful as materials used for the lubricating layer for a recording medium has not been clarified.

CITATION LIST

Patent Literature

[PTL 1] WO 04/031261A1
[PTL 2] JP-A-10-143838
[PTL 3] JP-A-2001-184622
[PTL 4] WO 01/021630 A1
[PTL 5] JP-A-2004-352999
[PTL 6] JP-A-2006-307201
[PTL 7] JP-A-2006-307202
[PTL 8] JP-A-2008-195799

Non Patent Literature

[NPL 1] "Degradation of perfluoropolyethers catalyzed by aluminum oxide", Paul H. Kasai, Wing T. Tang and Patrick Wheeler, Applied Surface Science, 51 (1991) 201-211

SUMMARY OF INVENTION

Problems to be Resolved by the Invention

An object of the invention is to provide a novel lubricant composition that is useful as a material used for a lubricating layer or the like of a magnetic recording medium and a magnetic recording medium using the lubricant composition.

Particularly, the object of the invention is to provide a novel lubricant composition that can realize a thin layer and can accomplish a high substrate-adsorptive property, sliding-resistance characteristic, and high stability with a thin layer and a magnetic recording medium using the composition.

Another object of the invention is to provide various uses of the lubricant composition, and the invention relates to a film, a laminate, a magnetic recording medium, a head slider, and a magnetic recording device that are produced using the composition.

Means of Solving the Problems

In order to solve the above problems, the present inventors synthesized various compounds, and examined the characteristics. As a result, the inventors found that the above object can be accomplished by a lubricant composition that contains a fluorine-based compound including a polar group such as a hydroxyl group near a cyclic group of a molecule having the cyclic group. The inventors also found that a magnetic disk using the compound for the lubricating layer is suitable for a high rotation disk device. Based on the findings, the inventors further repeated the examination, thereby completing the invention.

[1] A lubricant composition comprising at least one kind of a compound represented by the following Formula (1).

[Formula 1]

$$X\text{-}[Y\text{-}[Z\text{---}C_nF_{2n+1-m}H_m]_s]_t \quad (1)$$

[In the formula, X represents a cyclic group that may be substituted, and Y represents a single bond or a linking group having a valency of 2 or more, provided that at least one of X and Y includes 1 or more polar groups; Z represents a linking group having a valency of 2 or more and constituted with a carbon atom (C), a fluorine atom (F), and one or two kinds of arbitrary atoms (here, a hydrogen atom is excluded); n represents a real number of 1 to 10; m represents a real number of 0 to 1; and s and t independently represent a real number of 1 or greater. Here, when s is 2 or greater, a plurality of n, m, and Z may be independently the same as or different from each other, and when t is 2 or greater, a plurality of s and Y may be independently the same as or different from each other.]

[2] The lubricant composition according to [1],
wherein the one or more polar groups are selected from a group consisting of a hydroxyl group (—OH), an amino group (—NH$_2$), a mercapto group (—SH), a carboxyl group (—COOH), an alkoxycarbonyl group (—COOR; here, R is an alkyl group), a carbamoyl group (—CONH$_2$), a ureide group (—NHCONH$_2$), a sulfonamide group (—SO$_2$NH$_2$), a phosphoric acid group (—P(=O)(OH)$_3$), a phosphate group (—OP(=O)(OH)$_2$), a sulfide group (—S—), a disulfide group (—S—S—), an aminocarbonyl group (—NHCO—), a ureylene group (—NHCONH—), an imino group (NH or NR (R is a substituent)), and an aminosulfonyl group (—NHSO$_2$—).

[3] The lubricant composition according to [2],
wherein X includes 1 or more polar groups.

[4] The lubricant composition according to [2],
wherein Y includes 1 or more polar groups.

[5] The lubricant composition according to [2],
wherein X and Y independently include 1 or more polar groups.

[6] The lubricant composition according to any one of [1] to [5],
wherein the 1 or more polar groups are hydroxyl groups.

[7] The lubricant composition according to any one of [1] to [6],
wherein the fluorine atom content of Z is 50% by mass or more.

[8] The lubricant composition according to any one of [1] to [7],
wherein 1 or 2 kinds of the arbitrary atoms included in Z are selected from a group consisting of an oxygen atom (O), a nitrogen atom (N), and a sulfur atom (S).

[9] The lubricant composition according to any one of [1] to [8],
wherein said at least one kind of the compound represented by Formula (1) is a compound represented by the following Formula (2).

[Formula 2]

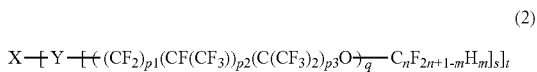

(2)

[In the formula, X represents a cyclic group that may be substituted, and Y represents a linking group having a valency of 2 or more, provided that at least one of X and Y includes 1 or more polar groups; p1 represents a real number of 1 to 4; p2 and p3 independently represent a real number of 0 to 4; q represents a real number of 1 to 30; n represents a real number of 1 to 10; m represents a real number of 0 to 1; and s and t independently represent a real number of 1 or greater. Here, there is no limitation on the binding order of $—(CF_2)_{p1}—$, $—(CFCF_3)_{p2}—$, and $—(C(CF_3)_2)_{p3}$ which constitute $—((CF_2)_{p1}(CFCF_3)_{p2}(C(CF_3)_2)_{p3}O)—$ in a polyfluoride polyether chain, and $—((CF_2)_{p1}(CFCF_3)_{p2}(C(CF_3)_2)_{p3}O)—$ means a group in which a perfluoroalkylene unit selected from $—(CF_2)_{p1}—$, $—(CFCF_3)_{p2}—$, and $—(C(CF_3)_2)_{p3}—$ and an oxygen atom are randomly distributed. When q is 2 or greater, a plurality of $—((CF_2)_{p1}(CFCF_3)_{p2}(C(CF_3)_2)_{p3}O)—$ may be the same as or different from each other, when s is 2 or greater, a plurality of n, m, and q may be independently the same as or different from each other, and when t is 2 or greater, a plurality of s and Y may be independently the same as or different from each other.]

[10] The lubricant composition according to any one of [1] to [9],
wherein the fluorine content per molecule is 35% by mass or more.

[11] The lubricant composition according to any one of [1] to [10],
wherein X is an aromatic cyclic group, a non-aromatic cyclic group, or a residue of a ligand coordinated with a metal.

[12] The lubricant composition according to any one of [1] to [11],
wherein Y is a linking group having a valency of 2 or more that includes at least an aromatic cyclic group and a polar group.

[13] The lubricant composition according to any one of [1] to [12],
wherein Y is a linking group having a valency of 2 or more that contains an aromatic cyclic group substituted with the polar group.

[14] The lubricant composition according to any one of [1] to [13],
wherein t is a real number of 2 or greater.

[15] The lubricant composition according to any one of [1] to [14],
wherein the fluorine content per molecule is 40% by mass or more.

[16] The lubricant composition according to any one of [1] to [15],
wherein Y is a linking group having a valency of 2 or more that contains a residue of an aromatic ring selected from a group consisting of benzene, acene, phenanthrene, chrysene, triphenylene, pyrene, picene, tetraphene, perylene, coronene, annulene, pyrrole, furan, benzofuran, isobenzofuran, indole, isoindole, thiophene, benzothiophene, imidazole, benzimidazole, purine, pyrazole, indazole, oxazole, isoxazole, benzoxazole, benzisoxazole, thiazole, isothiazole, benzothiazole, pyridine, quinoline, isoquinoline, pyridazine, pyrimidine, pyrazine, quinoxaline, acridine, quinazoline, cinnoline, and triazine, which are substituted with a polar group.

[17] The lubricant composition according to any one of [1] to [16],
wherein Y is a linking group having a valency of 2 or more that contains a residue of a benzene ring which is substituted with a polar group.

[18] The lubricant composition according to any one of [1] to [17],
wherein at least one of s units of $—Z—C_nF_{2n+1-m}H_m$ in Formula (1) includes $—(OCF_2CF_2)_kOC_nF_{2n+1}$ (here, k+n is 8 or less, and k is 6 or less) at the terminal.

[19] The lubricant composition according to any one of [1] to [17],
wherein at least one of s units of $—Z—C_nF_{2n+1-m}H_m$ in Formula (1) includes $—OCH_2CF_2—(OCF_2CF_2)_kOC_nF_{2n+1}$ (here, k+n is 8 or less, and k is 6 or less) at the terminal.

[20] The lubricant composition according to any one of [1] to [19],
wherein said at least one kind of the compound represented by Formula (1) is represented by the following Formula (3).

[Formula 3]

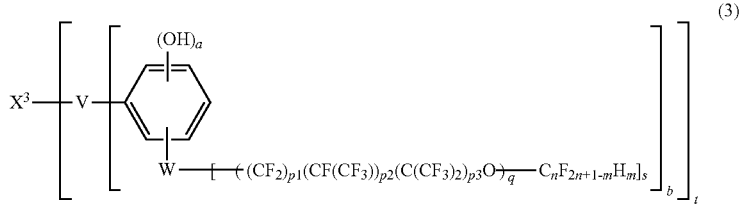

(3)

[In the formula, $X^3$ represents a cyclic group that may be substituted; V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4, provided that a+b is 2 to 5. Here, there is no limitation on the binding order of $—(CF_2)_{p1}—$, $—(CFCF_3)_{p2}—$, and $—(C(CF_3)_2)_{p3}$ which constitute $—((CF_2)_{p1}(CFCF_3)_{p2}(C(CF_3)_2)_{p3}O)—$ in a polyfluoride polyether chain in the formula, and $—((CF_2)_{p1}(CFCF_3)_{p2}(C(CF_3)_2)_{p3}O)—$ means a group in which a perfluoroalkylene unit selected from $—(CF_2)_{p1}—$, $—(CFCF_3)_{p2}—$, and $—(C(CF_3)_2)_{p3}—$ and an oxygen atom are randomly distributed. When q is 2 or greater, a plurality of $—((CF_2)_{p1}(CFCF_3)_{p2}(C(CF_3)_2)_{p3}O)—$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.]

[21] The lubricant composition according to [20], wherein $X^3$ is a residue of an aromatic ring selected from a group consisting of benzene, triphenylene, perylene, triazine, phthalocyanine, porphyrin, corrole, and coronene, which may be substituted.

[22] The lubricant composition according to any one of [1] to [21], wherein said at least one kind of the compound represented by Formula (1) is a compound represented by the following Formula (4).

[Formula 4]

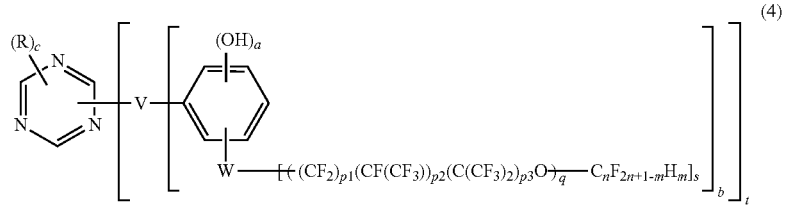

(4)

[In the formula, V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4, provided that a+b is 2 to 5; R represents an arbitrary substituent; and c represents a real number of 0 to 1. Here, c+t=3. Here, there is no limitation on the binding order of $-(CF_2)_{p1}-$, $-(CFCF_3)_{p2}-$, and $-(C(CF_3)_2)_{p3}$ which constitute $-((CF_2)_{p1}(CFCF_3)_{p2}(C(CF_3)_2)_{p3}O)-$ in a polyfluoride polyether chain in the formula, and $-((CF_2)_{p1}(CFCF_3)_{p2}(C(CF_3)_2)_{p3}O)-$ means a group in which a perfluoroalkylene unit selected from $-(CF_2)_{p1}-$, $-(CFCF_3)_{p2}-$, and $-(C(CF_3)_2)_{p3}-$ and an oxygen atom are randomly distributed. When q is 2 or greater, a plurality of $-((CF_2)_{p1}(CFCF_3)_{p2}(C(CF_3)_2)_{p3}O)-$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.]

[23] The lubricant composition according to any one of [20] to [22], wherein W is a divalent linking group including an imino group (NH or NR (R is a substituent)), an alkylene group with 1 to 20 carbon atoms (here, one carbon atom or two or more carbon atoms that are not adjacent to each other may be substituted with an oxygen atom), a carbonyl group (C=O), an oxy group (O), and a combination of 1 or more kinds selected from these groups.

[24] The lubricant composition according to any one of [20] to [23], wherein V is a single bond, an oxy group, —NH—, —N(alkyl)-, —N(substituted alkyl), a carbonyl group, a sulfonyl group, an alkylene group, or a combination thereof.

[25] The lubricant composition according to any one of [20] to [24], wherein at least one polyfluoride polyether chain in the formula is $-(OCF_2CF_2)_kOC_nF_{2n+1}$ (here, k+n is 8 or less, and k is 6 or less).

[26] The lubricant composition according to any one of [20] to [25], wherein a chain configured with at least one of —W and polyfluoride polyether chain in the formula is $-OCH_2CF_2-(OCF_2CF_2)_kOC_nF_{2n+1}$ (here, k+n is 8 or less, and k is 6 or less).

[27] The lubricant composition according to any one of [1] to [26], further comprising at least one kind of a perfluoroalkyl polyether oligomer represented by formulae (a), (b), (c), and (d):

$$A-CF_2O(CF_2CF_2O)_r(CF_2O)_sCF_2-B \quad (a)$$

[A and B independently represent $OHCH_2-$ or at least one kind of group selected from the following formula; r is any number from 1 to 30; and s is any number from 1 to 30; here, x is any number from 1 to 5]

[Formula 5]

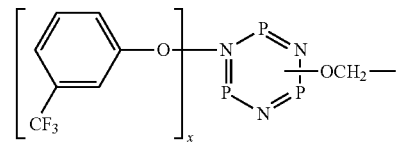

$$X-CF_2O(CF_2CF_2O)_m(CF_2O)_nCF_2-Y \quad (b)$$

[X and Y independently represent a group selected from F, $HO(CH_2CH_2O)_tCH_2-$, $HOCH_2CH(OH)CH_2OCH_2-$, HOOC—, and a piperonyl group; m is any number from 1 to 60; n is any number from 1 to 60; and t is any number from 1 to 30]

$$F[CF(CF_3)CF_2O]_uCF(CF_3)-X' \quad (c)$$

[X' represents F or —COOH; and u is any number from 1 to 60]

$$F[CF_2CF_2CF_2O]_vCF_2CF_2CH_2-Z \quad (d)$$

[Z represents a group selected from F, HO—, and COOH—, and v is any number from 1 to 60]

[28] The lubricant composition according to any one of [1] to [27], which is used as a lubricant of a disk for a magnetic recording medium.

[29] A film including the lubricant composition according to any one of [1] to [28].
[30] The film according to [29], which is formed by a dip coating method, a spin coating method, or vacuum vapor deposition.
[31] A laminate comprising:
a substrate in which at least a portion of the surface thereof includes carbon as a main material; and
the film according to [29] or [30] on the substrate.
[32] A magnetic recording medium at least comprising:
a magnetic layer; and
the film according to [29] or [30].
[33] The magnetic recording medium according to [32], further comprising a protective layer between the magnetic layer and the film.
[34] A head slider provided with a magnetic head, comprising the film according to [29] or [30] on at least a portion of the surface thereof.
[35] A magnetic recording device at least comprising one of:
the magnetic recording medium according to [32] or [33]; and
the head slider according to [34].
[36] A compound represented by the following Formula (3).

[Formula 6]

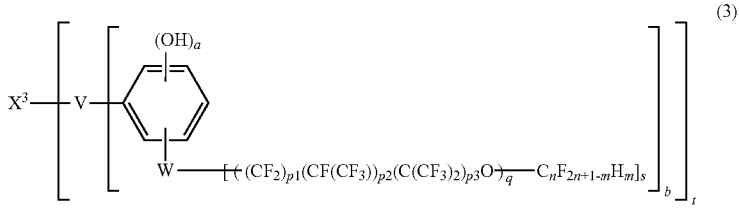

(3)

[In the formula, $X^3$ represents a cyclic group that may be substituted; V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4, provided that a+b is 2 to 5. Here, there is no limitation on the binding order of $-(CF_2)_{p1}-$, $-(CFCF_3)_{p2}-$, and $-(C(CF_3)_2)_{p3}-$ which constitute $-((CF_2)_{p1}(CFCF_3)_{p2}(C(CF_3)_2)_{p3}O)-$ in a polyfluoride polyether chain in the formula, and $-((CF_2)_{p1}(CFCF_3)_{p2}(C(CF_3)_2)_{p3}O)-$ means a group in which a perfluoroalkylene unit selected from $-(CF_2)_{p1}-$, $-(CFCF_3)_{p2}-$, and $-(C(CF_3)_2)_{p3}-$ and an oxygen atom are randomly distributed. When q is 2 or greater, a plurality of $-((CF_2)_{p1}(CFCF_3)_{p2}(C(CF_3)_2)_{p3}O)-$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.]
[37] The compound according to [36],
wherein $X^3$ is a substituted or unsubstituted triazine ring residue, a substituted or unsubstituted triphenylene residue, or a residue of an aza-crown ether ring.

EFFECT OF THE INVENTION

According to the invention, it is possible to provide a novel lubricant composition that is useful as a material used for a lubricating layer or the like of a magnetic recording medium and a magnetic recording medium using the lubricant composition.

Particularly, it is possible to provide a novel lubricant composition that can realize a thin layer and can accomplish a high substrate-adsorptive property, sliding-resistance characteristic, and high stability with a thin layer and a magnetic recording medium using the composition.

MODE FOR CARRYING OUT THE INVENTION

Figure 1:
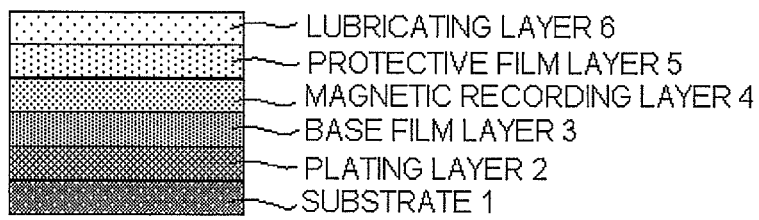
FIG. 1 is a schematic cross-sectional view of an example of a magnetic recording medium of the invention.

Hereinafter, the invention will be described in detail. In the present specification, a range of numerical values represented using "to" means a range that includes the numerical values described before and after the "to" as a minimum value and a maximum value.
1. Lubricant Composition
The invention relates to a lubricant composition that contains at least one kind of compound represented by the following Formula (1). The following compound contains a polar group such as a hydroxyl group or the like in at least one of X and Y in the formula. The polar group acts as a group binding to a substrate (or to a protective film layer such as a carbonaceous film, an oxide film such as $SiO_2$ and $ZrO_2$, a nitride film, and a boride film, and the like, which are formed on the substrate). For example, in the well-known lubricants "FOMBLIN Z-DOL" and "FOMBLIN Z-TETRAOL" described above, by using a compound that includes a hydroxyl group as a polar group at both terminals of perfluoropolyether, a substrate-adsorptive property is secured. As described above, the compound represented by the following Formula (1) has a polar group near a cyclic group of a molecule having the cyclic group. Accordingly, this compound has a higher degree of molecular freedom on the substrate compared to a compound having a hydroxyl group at both terminals of a chain-like molecule. As a result, the lubricant composition of the invention has an excellent sliding-resistance characteristic, and can maintain the sliding-resistance characteristic even if the non-adsorptive layer is absent.

Moreover, in the invention, by using the compound of the following Formula (1), the non-adsorptive layer can be removed, and the lubricating layer can be thinner.
[Formula 7]

(1)

In the formula, X represents a cyclic group that may be substituted, and Y represents a single bond or a linking group having a valency of 2 or more. Here, at least one of X and Y includes 1 or more polar groups; Z represents a linking group having a valency of 2 or more and constituted with a carbon atom (C), a fluorine atom (F), and 1 or 2 kinds of arbitrary atoms (here, a hydrogen atom is excluded); n represents a real number of 1 to 10; m represents a real number of 0 to 1; and s and t independently represent a real number of 1 or greater. Here, when s is 2 or greater, a plurality of n, m, and Z may be independently the same as or different from each other, and when t is 2 or greater, a plurality of s and Y may be independently the same as or different from each other.

In Formula (1), X represents a cyclic group that may be substituted. Examples of the cyclic group include both the residue of an aromatic ring (aromatic cyclic group) and the residue of a non-aromatic ring (non-aromatic cyclic group such as an aza-crown ring including 12-aza-crown-4, 15,18, 21,24-aza-crown, and the like and a cyclohexane ring). In addition, the cyclic group may be a residue of a ligand coordinated with a metal, or may be a group that is originally a chain-like group but forms a cyclic structure for the first time by being coordinated with a central metal. That is, in the present specification, the "cyclic group" is included in the meaning of a cyclic group as long as the cyclic group forms a cyclic structure type aggregate, supermolecule, or complex by clustering of a plurality of molecules, even if the "cyclic group" is originally a non-cyclic group such as a chain-like group. Among those, an aromatic cyclic group is preferable. Though there is no particular limitation on atoms constituting the cyclic group, it is preferable that at least a carbon atom be included as a ring-constituting atom. The cyclic group may be selected from cyclic groups including only the carbon atom as the ring-constituting atom, or from cyclic groups including a hetero atom such as a nitrogen atom, an oxygen atom, and a sulfur atom as the ring-constituting atom together with the carbon atom. From the viewpoint of a substrate-adsorptive property, it is preferable that the cyclic group be selected from cyclic groups including the hetero atom as the ring-constituting atom, and particularly, from cyclic groups including the nitrogen atom, such as a residue of a triazine ring. Furthermore, a cyclic group formed by connecting a plurality of residues of hetero rings into a ring shape is also preferable. As a cyclic multidentate ligand, a well-known residue of phthalocyanine, porphyrin, corrole, and the like is also preferable. These cyclic groups may be in a state of being coordinated to the central metal. Hereinbelow, examples of the hetero cyclic group that is preferable as examples of X are shown, but the cyclic group is not limited thereto. Moreover, hereinbelow, the substituent of the cyclic group and the central metal are removed, and only the skeleton of the cyclic group is shown. Y may be substituted in any position, and among the cyclic groups shown below, any of substitutable hydrogen atoms may be substituted with Y.

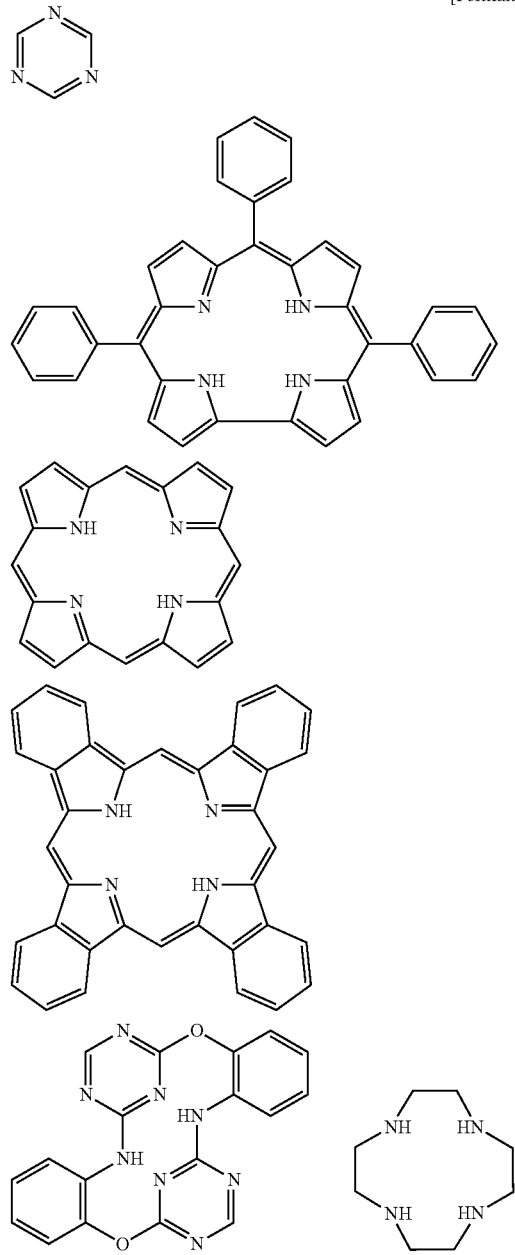
[Formula 8]

Examples of the aromatic cyclic group having only carbon atoms as the ring-constituting atom include a residue of a benzene ring. A residue of a ring (for example, triphenylene, phenylene, and coronene) formed by the condensation of a plurality of benzene rings, and a cyclic group formed when a plurality of benzene rings are connected into a ring shape are also preferable. Hereinbelow, examples of the aromatic cyclic group including only the carbon atoms as the ring-constituting atom are shown, but the cyclic group is not limited thereto. Moreover, hereinbelow, the substituent is removed, and only the skeleton of the cyclic group is shown. Y may be substituted in any position, and among the cyclic groups shown below, any of substitutable hydrogen atoms may be substituted with Y.

[Formula 9]

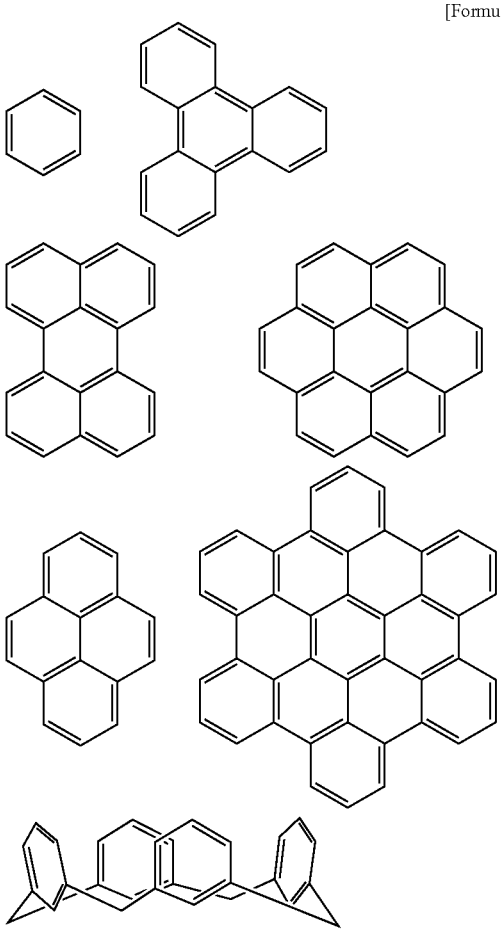

Examples of the non-aromatic alicyclic group include the following ones, but the alicyclic group is not limited thereto. Moreover, hereinbelow, the substituent is removed, and only the skeleton of the cyclic group is shown. Y may be substituted in any position, and among the cyclic groups shown below, any of substitutable hydrogen atoms may be substituted with Y.

[Formula 10]

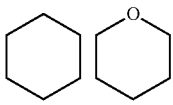

The cyclic group represented by X may include 1 or more substituents. Examples of the substituent include various substituents including a polar group such as a hydroxyl group. The polar group such as a hydroxyl group may bind to the ring-constituting atom of the cyclic group directly or through a linking group. Examples of the linking group include an alkylene group with 1 to 20 carbon atoms, an alkenylene group with 2 to 20 carbon atoms, an alkynylene group with 2 to 20 carbon atoms, an aromatic cyclic group with 1 to 20 carbon atoms, and the like (here, one carbon atom in a linking chain or 2 or more carbon atoms that are not adjacent to each other may be substituted with atoms of oxygen, nitrogen, sulfur, and the like, and a hydrogen atom may be substituted with a fluorine atom).

And, examples of the substituent with which the cyclic group represented by X may be substituted include a hydrogen atom and the following Substituent Group T.

Substituent Group T:

Halogen atoms (e.g., fluorine, chlorine, bromine and iodine atoms), alkyls (preferably $C_{1-30}$ alkyls such as methyl, ethyl, n-propyl, isopropyl, tert-butyl, n-octyl and 2-ethylhexyl), cycloalkyls (preferably $C_{3-30}$ substituted or non-substituted cycloalkyls such as cyclohexyl, cyclopentyl and 4-n-dodecyl cyclohexyl), bicycloalkyls (preferably $C_{5-30}$ substitute or non-substituted bicycloalkyls, namely monovalent residues formed from $C_{5-30}$ bicycloalkanes from which a hydrogen atom is removed, such as bicyclo [1,2,2]heptane-2-yl and bicyclo [2,2,2]octane-3-yl), alkenyls (preferably $C_{2-30}$ alkenyls such as vinyl and allyl); cycloalkenyls (preferably $C_{3-30}$ substituted or non-substituted cycloalkenyls, namely monovalent residues formed from $C_{3-30}$ cycloalkenes from which a hydrogen atom is removed, such as 2-cyclopentene-1-yl and 2-cyclohexene-1-yl), bicycloalkenyls (preferably $C_{5-30}$ substituted or non-substituted bicycloalkenyls, namely monovalent residues formed from $C_{5-30}$ bicycloalkenes from which a hydrogen atom is removed, such as bicyclo [2,2,1]hepto-2-en-1-yl and bicyclo[2,2,2]octo-2-en-4-yl), alkynyls (preferably $C_{2-30}$ substitute or non-substituted alkynyls such as ethynyl and propargyl), aryls (preferably $C_{6-30}$ substitute or non-substituted aryls such as phenyl, p-tolyl and naphthyl), heterocyclic groups (preferably (more preferably $C_{3-30}$) substituted or non-substituted, 5-membered or 6-membered, aromatic or non-aromatic heterocyclic monovalent residues such as 2-furyl, 2-thienyl, 2-pyrimidinyl and 2-benzothiazolyl), cyano, hydroxyl, nitro, carboxyl, alkoxys (preferably $C_{1-30}$ substituted or non-substituted alkoxys such as methoxy, ethoxy, iso-propoxy, tert-butoxy, n-octyloxy and 2-methoxyethoxy), aryloxys (preferably $C_{6-30}$ substituted or non-substituted aryloxys such as phenoxy, 2-methylphenoxy, 4-t-butylphenoxy, 3-nitrophenoxy and 2-tetradecanoyl aminophenoxy), silyloxys (preferably $C_{3-20}$ silyloxys such as trimethylsilyloxy and tert-butyldimethylsilyloxy), hetero-cyclic-oxys (preferably $C_{2-30}$ substituted or non-substituted hetero-cyclic-oxys such as 1-phenyltetrazole-5-oxy and 2-tetrahydropyrenyloxy), acyloxys (preferably $C_{2-30}$ substitute or non-substituted alkylcarbonyloxys and $C_{6-30}$ substituted or non-substituted arylcarbonyloxys such as formyloxy, acetyloxy, pivaloyloxy, stearoyoxy, benzoyloxy and p-methoxyphenylcarbonyloxy), carbamoyloxys (preferably $C_{1-30}$ substituted or non-substituted carbamoyloxys such as N,N-dimethyl carbamoyloxy, N,N-diethyl carbamoyloxy, morpholinocarbonyloxy, N,N-di-n-octylaminocarbonyloxy and N-n-octylcarbamyloxy), alkoxy carbonyloxys (preferably $C_{2-30}$ substituted or non-substituted alkoxy carbonyloxys such as methoxy carbonyloxy, ethoxy carbonyloxy, tert-butoxy carbonyloxy and n-octyloxy carbonyloxy), aryloxy carbonyloxys (preferably $C_{7-30}$ substituted or non-substituted aryloxy carbonyloxys such as phenoxy carbonyloxy, p-methoxyphenoxy carbonyloxy and p-n-hexadecyloxyphenoxy carbonyloxy), aminos (preferably $C_{0-30}$ substituted or non-substituted alkylaminos and $C_{6-30}$ substituted or non-substituted arylaminos such as amino, methylamino, dimethylamino, anilino, N-methyl-anilino and diphenylamino), acylaminos (preferably $C_{1-30}$ substituted or non-substituted alkylcarbonylaminos and $C_{6-30}$ substituted or non-substituted arylcarbonylaminos such as formylamino, acetylamino, pivaloylamino, lauroylamino and benzoylamino), aminocarbonylaminos (preferably $C_{1-30}$ substituted or non-substituted aminocarbonylaminos such as carbamoylamino, N,N-dimethylaminocarbonylamino, N,N-diethylamino carbonylamino and morpholino carbonylamino), alkoxycarbonylaminos (preferably $C_{2-30}$ substituted or non-substituted alkoxycarbonylaminos such as methoxycarbonylamino, ethoxycarbonylamino, tert-butoxycarbonylamino, n-octadecyloxycarbonylamino and N-methyl-methoxy carbonylamino), aryloxycarbonylaminos (preferably $O_{7-30}$ substituted or non-substituted aryloxycarbonylaminos such as phenoxycarbonylamino, p-chloro phenoxycarbonylamino and m-n-octyloxy phenoxy carbonylamino), sulfamoylaminos (preferably $C_{0-30}$ substituted or non-substituted sulfamoylaminos such as sulfamoylamino, N,N-dimethylamino sulfonylamino and N-n-octylamino sulfonylamino), alkyl- and aryl-sulfonylaminos (preferably $C_{1-30}$ substituted or non-substituted alkyl-sulfonylaminos and $C_{6-30}$ substituted or non-substituted aryl-sulfonylaminos such as methyl-sulfonylamino, butyl-sulfonylamino, phenyl-sulfonylamino, 2,3,5-trichlorophenyl-sulfonylamino and p-methylphenyl-sulfonylamino), mercapto, alkylthios (preferably substituted or non-substituted $C_{1-30}$ alkylthios such as methylthio, ethylthio and n-hexadecylthio), arylthios (preferably $C_{6-30}$ substituted or non-substituted arylthios such as phenylthio, p-chlorophenylthio and m-methoxyphenylthio), heterocyclic-thios (preferably $C_{2-30}$ substituted or non-substituted heterocyclic-thios such as 2-benzothiazolyl thio and 1-phenyltetrazol-5-yl-thio), sulfamoyls (preferably $C_{0-30}$ substituted or non-substituted sulfamoyls such as N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl), sulfo, alkyl- and aryl-sulfinyls (preferably $C_{1-30}$ substituted or non-substituted alkyl- or $C_{6-30}$ substituted or non-substituted aryl-sulfinyls such as methylsulfinyl, ethylsulfinyl, phenylsulfinyl and p-methylphenylsulfinyl), alkyl- and aryl-sulfonyls (preferably $C_{1-30}$ substituted or non-substituted alkyl-sulfonyls and $C_{6-30}$ substituted or non-substituted arylsulfonyls such as methylsulfonyl, ethylsulfonyl, phenylsulfonyl and p-methylphenylsulfonyl), acyls (preferably $C_{2-30}$ substituted non-substituted alkylcarbonyls, and $C_{7-30}$ substituted or non-substituted arylcarbonyls such as formyl, acetyl and pivaloyl benzyl), aryloxycarbonyls (preferably $C_{7-30}$ substituted or non-substituted aryloxycarbonyls such as phenoxycarbonyl, o-chlorophenoxycarbonyl, m-nitrophenoxycarbonyl and p-tert-butylphenoxycarbonyl), alkoxycarbonyls (preferably $C_{2-30}$ substituted or non-substituted alkoxycarbonyls such as methoxycarbonyl, ethoxycarbonyl, tert-butoxycarbonyl and n-octadecyloxycarbonyl), carbamoyls (preferably $C_{1-30}$ substituted or non-substituted carbamoyls such as carbamoyl, N-methylcarbamoyl, N,N-dimethylcarbamoyl, N,N-di-n-octylcarbamoyl and N-(methylsulfonyl)carbamoyl), aryl- and heterocyclic-azos (preferably $C_{6-30}$ substituted or non-substituted arylazos and $C_{3-30}$ substituted or non-substituted heterocyclicazos such as phenylazo, p-chlorophenylazo, 5-ethylthio-1,3,4-thiadiazol-2-yl-azo), imides (preferably, N-succinimide and N-phthalimide), phosphinos (preferably $C_{2-30}$ substituted or non-substituted phosphinos such as dimethyl phosphino, diphenyl phosphino and methylphenoxy phosphino), phosphinyls (preferably $C_{2-30}$ substituted or non-substituted phosphinyls such as phosphinyl, dioctyloxy phosphinyl and diethoxy phosphinyl), phosphinyloxys (preferably $C_{2-30}$ substituted or non-substituted phosphinyloxys such as diphenoxyphosphinyloxy and dioctyloxyphosphinyloxy), phosphinylaminos (preferably $C_{2-30}$ substituted or non-substituted phosphinylaminos such as dimethoxy phosphinylamino and dimethylamino phosphinylamino) and silyls (preferably $C_{3-30}$ substituted or non-substituted silyls such as trimethylsilyl, tert-butylmethylsilyl and phenyldimethylsilyl).

In the Formula (1), preferable examples of the substituent of X include a substituent including a polar group such as a hydroxyl group (which means that a polar group itself such as a hydroxyl group is also included), and a substituent including a fluorine atom. It is preferable that X include a substituent including a polar group such as a hydroxyl group, or be unsubstituted.

In Formula (1), Y represents a single bond or a linking group having a valency of 2 or more. It is preferable that Y be a linking group including a polar group such as a hydroxyl group. As the linking group having a valency of 2 or more represented by Y, a substituted or unsubstituted imino group (NH or NR(R is a substituent)), sulfide group (S), alkylene group with 1 to 20 carbon atoms (here, one carbon atom or 2 or more carbon atoms that are not adjacent to each other may be substituted with atoms of oxygen, nitrogen, sulfur, and the like, and a hydrogen atom may be substituted with a fluorine atom), alkenylene group with 2 to 20 carbon atoms, alkynylene group with 2 to 20 carbon atoms, aromatic cyclic group, carbonyl group (C=O), sulfonyl group (S=O), a phosphoryl group (P=O), oxy group (O), and a linking group having a valency of 2 or more and including a combination of 1 or more kinds selected from these groups are preferable.

Among these, it is preferable that Y include an aromatic cyclic group that may be substituted, that is, a residue of an aromatic ring. It is preferable that the aromatic cyclic group be substituted with a polar group such as a hydroxyl group directly or through a linking group. In the present specification, the term "aromatic cyclic group" is used not only for a residue of a hydrocarbon aromatic ring but for a residue of an aromatic hetero ring that includes a hetero atom as a ring-constituting atom. Examples of the linking group are the same as the examples of a linking group in an embodiment in which the linking group is present between X and a polar group such as a hydroxyl group. Preferable examples of the aromatic cyclic group include a residue of an aromatic ring selected from a group consisting of benzene, acene, phenanthrene, chrysene, triphenylene, pyrene, picene, tetraphene, perylene, coronene, annulene, pyrrole, furan, benzofuran, isobenzofuran, indole, isoindole, thiophene, benzothiophene, imidazole, benzimidazole, purine, pyrazole, indazole, oxazole, isoxazole, benzoxazole, benzisoxazole, thiazole, isothiazole, benzothiazole, pyridine, quinoline, isoquinoline, pyridazine, pyrimidine, pyrazine, quinoxaline, acridine, quinazoline, cinnoline, and triazine. Among these, Y preferably includes a residue of a benzene ring (for example, a phenylene group if Y has a valency of 2), and particularly preferably includes a residue of a benzene ring that is substituted with a polar group such as a hydroxyl group directly or through a linking group.

The compound of Formula (1) includes one or more polar groups in at least one of X and Y The polar group may be a monovalent group located at a terminal or a divalent group located at positions other than the terminal. In respect of the adsorptive property with respect to the substrate surface, the polar group is preferably a monovalent group located at the terminal. Examples of the polar group include a hydroxyl group (—OH), an amino group (—$NH_2$), a mercapto group (—SH), a carboxyl group (—COOH), an alkoxycarbonyl group (—COOR; here, R is an alkyl group), a carbamoyl group (—$CONH_2$), a ureide group (—$NHCONH_2$), a sulfonamide group (—$SO_2NH_2$), a phosphoric acid group (—P(=O)($OH)_3$), a phosphate group (—OP(=O)($OH)_2$), a sulfide group (—S—), a disulfide group (—S—S—), an aminocarbonyl group (—NHCO—), a ureylene group (—NHCONH—), an imino group (NH or NR (R is a substituent)), and an aminosulfonyl group (—$NHSO_2$—). When Y includes a polar group in a linking portion with X and Z, the polar group is selected from divalent groups among the above groups.

Among these, from the viewpoint described above, a monovalent polar group is preferable, and a hydroxyl group is preferable among the groups.

Examples of the compound of Formula (1) include all of an example in which only X includes a polar group such as a hydroxyl group, an example in which only Y includes a polar group such as a hydroxyl group, and an example in which both the X and Y include a polar group such as a hydroxyl group. In the invention, by positioning, as a substituent, a polar group such as a hydroxyl group having the substrate-binding property in one of X that is a cyclic group positioned not at both terminals of a molecule but at the center of the molecule and Y (preferably, Y including an aromatic cyclic group) that binds to X, the substrate-binding property of the polar group such as a hydroxyl group is more enhanced, and the sliding-resistance characteristic improves.

In Formula (1), Z represents a linking group having a valency of 2 or more and constituted with a hydrogen atom (C), a fluorine atom (F), and 1 or 2 or more kinds of arbitrary atoms (here, a hydrogen atom is excluded). Preferable examples of atoms (here, a hydrogen atom is excluded) other than C and F included in Z include an oxygen atom (O), a nitrogen atom (N), and a sulfur atom (S). Among these, 0 is preferable. Preferable examples of Z include —$[(CF_2)_{p1}(CFCF_3)_{p2}(C(CF_3)_2)_{p3}O]_q$—. In the formula, p1 represents a real number of 1 to 4; p2 and p3 independently represent a real number of 0 to 4; and q represents a real number of 1 to 30. Among these, p1 is preferably 2 to 3, p2 is preferably 0 to 2, and p3 is preferably 0 to 2. q is preferably 2 to 20, and more preferably 3 to 10. These are not necessarily integers. That is, the compound of Formula (1) may be a mixture of 2 or more kinds of compounds in which one of p1, p2, p3, and q has a different group. When q is 2 or greater, a plurality of groups —$[(CF_2)_{p1}(CFCF_3)_{p2}(C(CF_3)_2)_{p3}O]$— may be the same as or different from each other.

The fluorine atom content of the linking group Z having a valency of 2 or more is preferably 50% by mass or more, and more preferably 55% to 80% by mass. If the fluorine atom content of Z is in this range, it is preferable in terms of the improvement of the lubricating property. The fluorine atom content of all compounds represented by Formula (1) is preferably 35% by mass or more, more preferably 45% to 65% by mass, and even more preferably 50% to 60% by mass. If the fluorine atom content of all molecules is in this range, it is preferable in terms of the reduction of surface energy, for example.

The compound represented by Formula (1) includes a group —$C_nF_{2n+1-m}H_m$ at a terminal portion of a side chain. n is a real number of 1 to 10, and m is a real number of 0 to 1. n is preferably 2 to 8, and m is preferably 0.

In the Formula (1), s and t independently represent a real number of 1 or greater. s is preferably 1 to 4, and more preferably 1 to 3. t is preferably 2 or greater, and more preferably 2 to 6. If t is 2 or greater, it is preferable in terms of the improvement of the lubricating property and the reduction of the surface energy, for example.

Preferable examples of the compound of the Formula (1) includes a compound in which at least one of s units of —Z—$C_nF_{2n+1-m}$ in Formula (1) includes —$(OCF_2CF_2)_kOC_nF_{2n+1}$ (here, k+n is 8 or less, and k is 6 or less) at the terminal; and a compound in which at least one of s units of —Z—$C_nF_{2n+1-m}H_m$ in Formula (1) includes —$OCH_2CF_2$—$(OCF_2CF_2)_kOC_nF_{2n+1}$ (here, k+n is 8 or less, and k is 6 or less) at the terminal.

The compound of the Formula (1) according to the invention has a property in which a perfluoropolyether (PFPE) chain of the side chain thereof is oriented vertically with respect to a substrate surface while the cyclic group faces the substrate surface, as described later. According to this property, if there is a large number of short PFPE chains, the lubricating layer could be made thin. If the value of k+n and k are in the range described above, a compound that sufficiently exhibits those properties of the PFPE chain can be produced at low cost, which is thus preferable.

Preferable examples of the compound represented by Formula (1) include a compound represented by the following Formula (2).

[Formula 11]

(2)

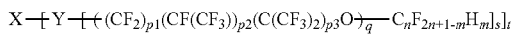

In the formula, X represents a cyclic group that may be substituted, and Y represents a linking group having a valency of 2 or more. Here, at least one of X and Y includes 1 or more polar groups such as a hydroxyl group; p1 represents a real number of 1 to 4; p2 and p3 independently represent a real number of 0 to 4; q represents a real number of 1 to 30; n represents a real number of 1 to 10; m represents a real number of 0 to 1; and s and t independently represent a real number of 1 or greater. The definitions and preferable ranges of the respective signs in Formula (2) are the same as those in the Formula (1), and the preferable ranges thereof are also the same. The preferable ranges of p1, p2, p3, and q are also the same as those described above.

Here, there is no limitation on the binding order of —$(CF_2)_{p1}$—, —$(CFCF_3)_{p2}$—, and —$(C(CF_3)_2)_{p3}$— in —$((CF_2)_{p1}(CFCF_3)_{p2}(C(CF_3)_2)_{p3}O)$— of Formula (2). —$((CF_2)_{p1}(CFCF_3)_{p2}(C(CF_3)_2)_{p3}O)$— means a group in which a perfluoroalkylene unit selected from —$(CF_2)_{p1}$—, —$(CFCF_3)_{p2}$—, and —$(C(CF_3)_2)_{p3}$— and an oxygen atom are randomly distributed. The compound of Formula (2) is a compound in which t units of linking groups Y each of which has s units of side chains where the perfluoroalkylene unit selected from —$(CF_2)_{p1}$—, —$(CFCF_3)_{p2}$—, and —$(C(CF_3)_2)_{p3}$— and an oxygen atom are randomly distributed is coordinated to the cyclic group X. When q is 2 or greater, a plurality of —$((CF_2)_{p1}(CFCF_3)_{p2}(C(CF_3)_2)_{p3}O)$— may be the same as or different from each other, when s is 2 or greater, a plurality of n, m, and q may be independently the same as or different from each other, and when t is 2 or greater, a plurality of s and Y may be independently the same as or different from each other.

Preferable examples of the compound represented by Formula (1) include a compound represented by the following Formula (3).

[Formula 12]

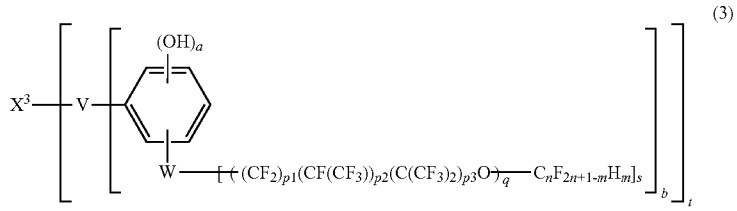

In the formula, $X^3$ represents a cyclic group that may be substituted; V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4. Here, a+b is 2 to 5. The definitions and preferable ranges of the respective signs in Formula (3) are the same as those in the Formula (1), and the preferable ranges thereof are also the same. The preferable ranges of p1, p2, p3, and q are also the same as those described above. In addition, when q is 2 or greater, a plurality of $-((CF_2)_{p1}(CFCF_3)_{p2}(C(CF_3)_2)_{p3}O)-$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.

In Formula (3), $X^3$ represents a cyclic group that may be substituted. Preferable examples of the cyclic group represented by $X^3$ are the same as the preferable examples of the cyclic group represented by X in Formula (1). Examples of the substituent are also the same as the substituent included in X. $X^3$ may be an aromatic cyclic group or a non-aromatic cyclic group. Preferable examples of the aromatic cyclic group include a substituted or unsubstituted triazine ring residue, a substituted or unsubstituted triphenylene residue, and a substituted or unsubstituted benzene ring residue, but the aromatic cyclic group is not limited thereto. Preferable examples of the non-aromatic cyclic group include a residue of an aza-crown ether ring, but the non-aromatic cyclic group is not limited thereto.

In Formula (3), V and W independently represent a single bond or a linking group having a valency of 2 or more (preferably, valency of 2 or 3). It is preferable that the linking group having a valency of 2 or more represented by the respective V and W have a chain shape. Examples of the linking group include a substituted or unsubstituted imino group (NH or NR (R is a substituent)), sulfide group (S), alkylene group with 1 to 20 carbon atoms (here, one carbon atom or 2 or more carbon atoms that are not adjacent to each other may be substituted with an oxygen atom), alkenylene group with 2 to 20 carbon atoms, alkynylene group with 2 to 20 carbon atoms, carbonyl group (C=O), sulfonyl group (S=O), phosphoryl group (P=O), oxy group (O), and a linking group having a valency of 2 or more and including a combination of 1 or more kinds selected from these groups.

In Formula (3), as V, a single bond, a substituted or unsubstituted imino group, oxy group, and an alkynylene group with 2 to 20 carbon atoms are preferable. A substituent R of the substituted imino group is preferably an alkyl group with 1 to 20 carbon atoms (here, one carbon atom or 2 or more carbon atoms that are not adjacent to each other may be substituted with an oxygen atom). Among these, V is preferably a single bond, an oxy group, —NH—, —N(alkyl)-, —N(substituted alkyl), a carbonyl group, a sulfonyl group, an alkylene group, or a combination thereof. Particularly, when $X^3$ is a substituted or unsubstituted triazine residue, V is preferably a single bond, an oxy group (—O—), —NH—, —N(alkyl group)-, and —N(substituted alkyl group)-. From the viewpoints of the simplicity of synthesis and performance, V is preferably —N(alkyl)-, —N(methyl)-, or —N(ethyl)-.

In Formula (3), as W, an imino group (NH or NR (R is a substituent)), an alkylene group with 1 to 20 carbon atoms (here, one carbon atom or two or more carbon atoms that are not adjacent to each other may be substituted with an oxygen atom), a carbonyl group (C=O), an oxy group (O), and a linking group having a valency of 2 or more and including a combination of 1 of more kinds selected from these groups are preferable.

In Formula (3), a and b independently represent a real number of 1 to 4. Here, a+b is 2 to 5.

Preferable examples of the compound represented by Formula (1) include a compound represented by the following Formula (4).

[Formula 13]

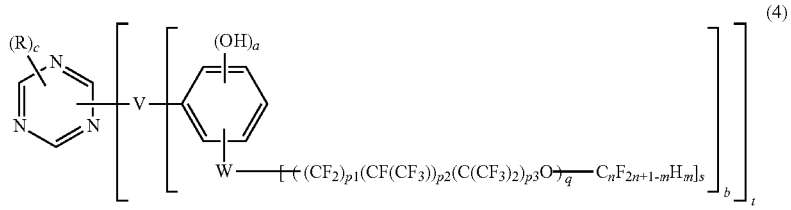

In the formula, V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4. Here, a+b is 2 to 5; R represents an arbitrary substituent; and c represents a real number of 0 to 1. Here, c+t=3. When q is 2 or greater, a plurality of $-((CF_2)_{p1}(CFCF_3)_{p2}(C(CF_3)_2)_{p3}O)-$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and v may be independently the same as or different from each other.

The definitions of signs in Formula (4) are the same as the respective signs in Formula (3), and preferable ranges thereof are also the same.

Examples of the substituent R in Formula (4) are the same as the examples of the substituent included in the cyclic group X in Formula (1), and the preferable ranges thereof are also the same. That is, R is preferably a substituent including a polar group such as a hydroxyl group (which means that a polar group itself such as a hydroxyl group is also included), and a substituent including a fluorine atom. It is preferable that the triazine ring in Formula (4) have a substituent including a polar group such as a hydroxyl group or the like, or be unsubstituted.

Examples of the compound represented by formula (1) include, but are not limited to, those shown below. The numerical value in the parenthesis added to each of the exemplified compound numbers means the fluorine atom content thereof.

[Formula 14]

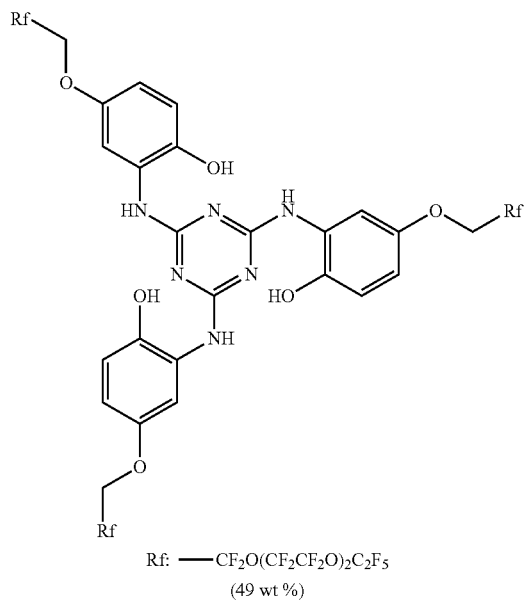

1

Rf: —$CF_2O(CF_2CF_2O)_2C_2F_5$
(49 wt %)

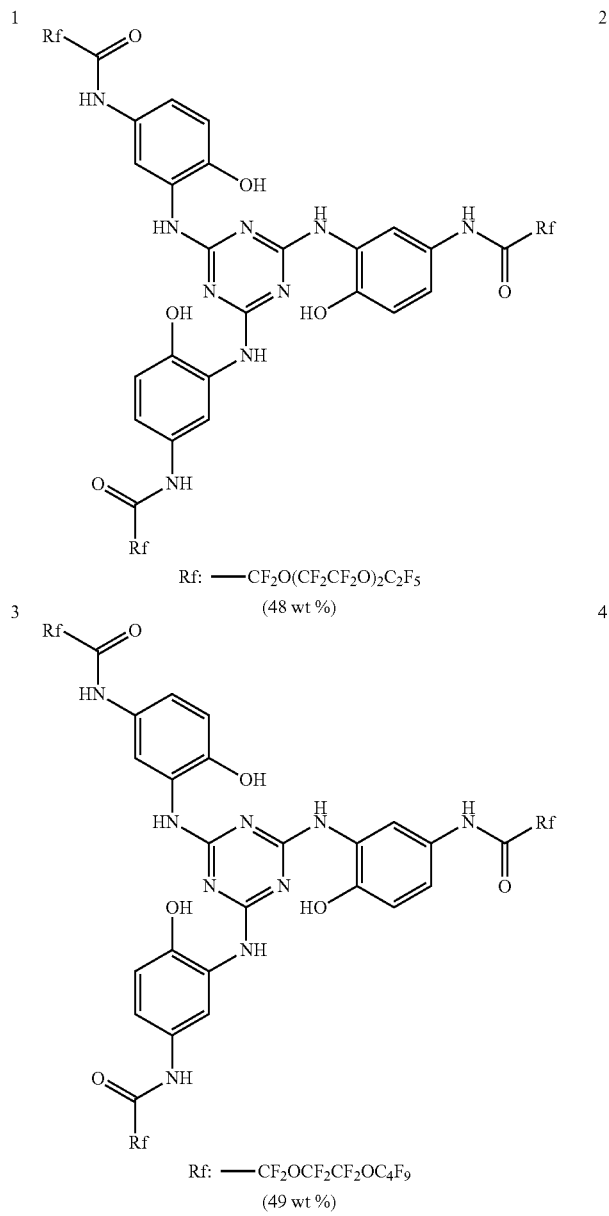

2

Rf: —$CF_2O(CF_2CF_2O)_2C_2F_5$
(48 wt %)

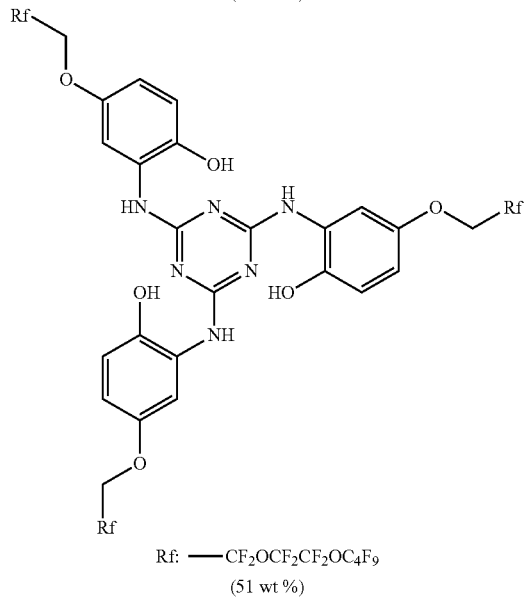

3

Rf: —$CF_2OCF_2CF_2OC_4F_9$
(51 wt %)

4

Rf: —$CF_2OCF_2CF_2OC_4F_9$
(49 wt %)

-continued
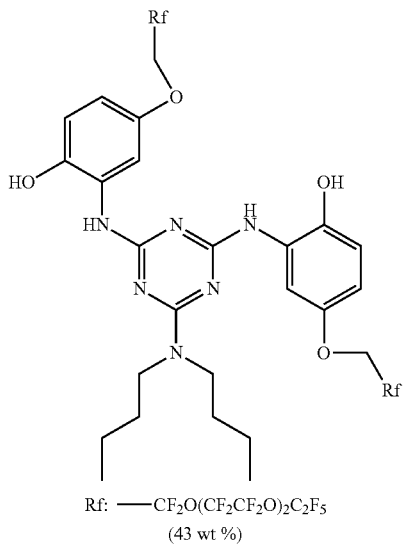
5
Rf: —CF$_2$O(CF$_2$CF$_2$O)$_2$C$_2$F$_5$
(43 wt %)
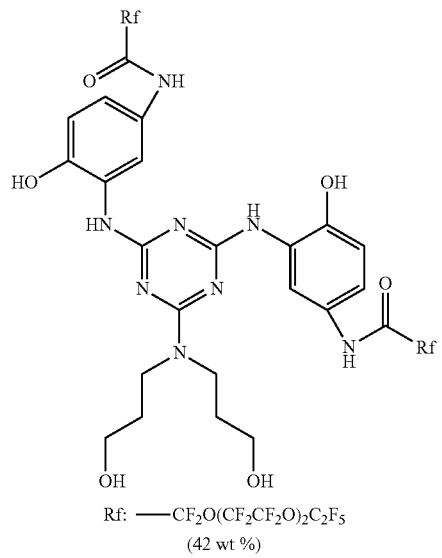
6
Rf: —CF$_2$O(CF$_2$CF$_2$O)$_2$C$_2$F$_5$
(42 wt %)
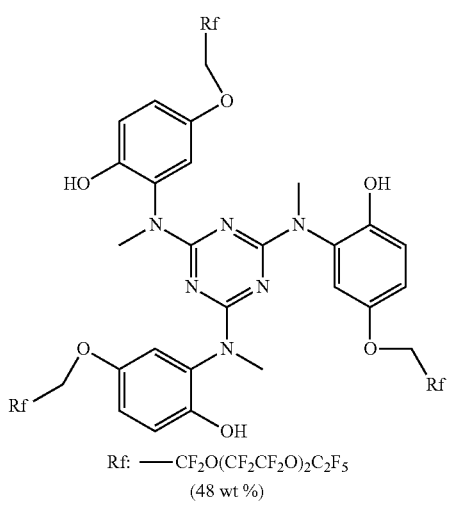
7
Rf: —CF$_2$O(CF$_2$CF$_2$O)$_2$C$_2$F$_5$
(48 wt %)
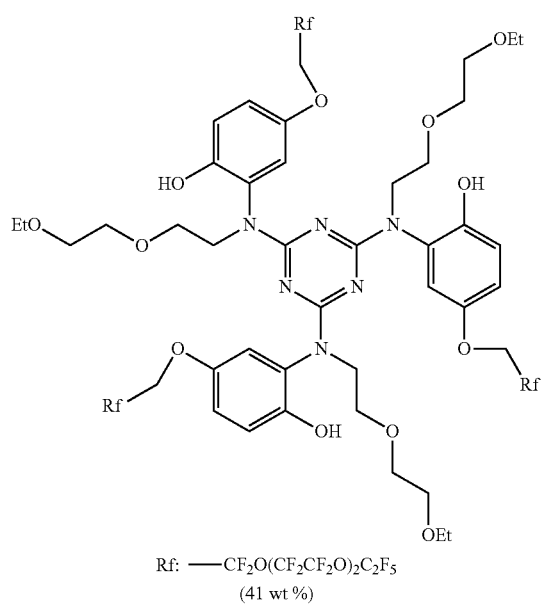
8
Rf: —CF$_2$O(CF$_2$CF$_2$O)$_2$C$_2$F$_5$
(41 wt %)

-continued
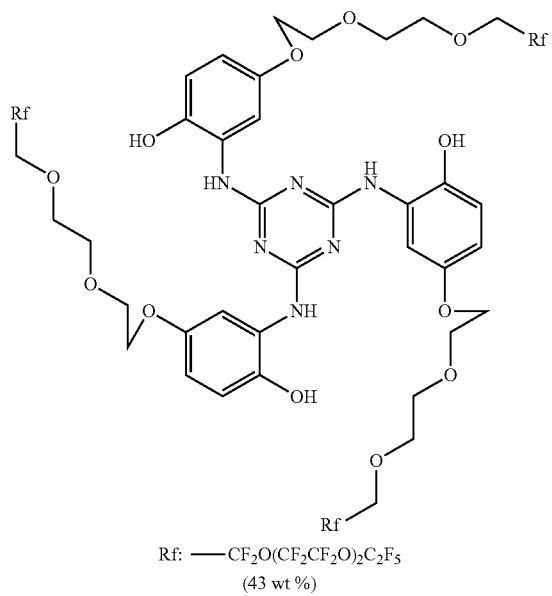
9
Rf: —CF$_2$O(CF$_2$CF$_2$O)$_2$C$_2$F$_5$
(43 wt %)
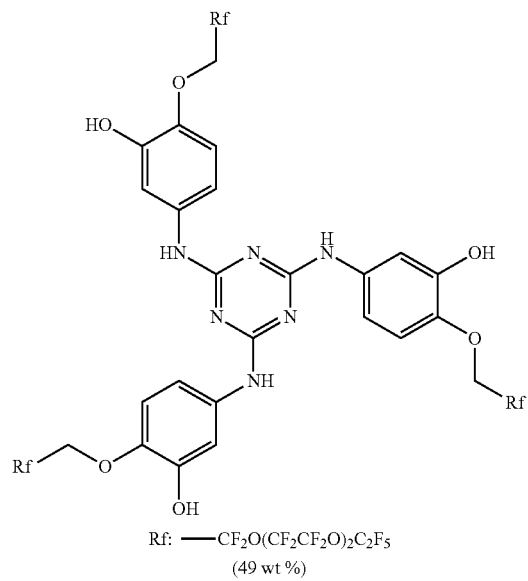
10
Rf: —CF$_2$O(CF$_2$CF$_2$O)$_2$C$_2$F$_5$
(49 wt %)
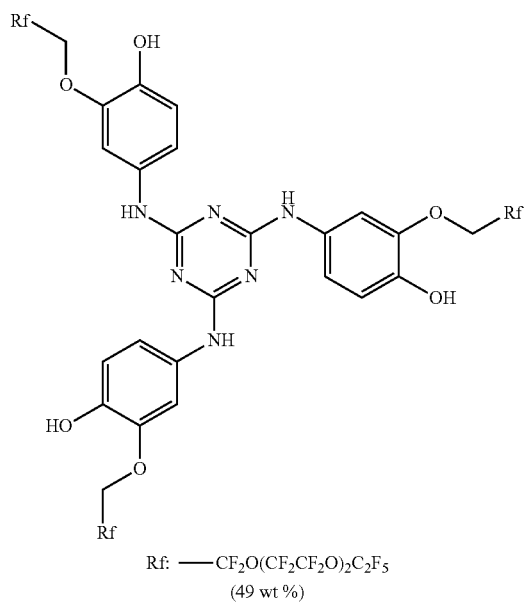
11
Rf: —CF$_2$O(CF$_2$CF$_2$O)$_2$C$_2$F$_5$
(49 wt %)
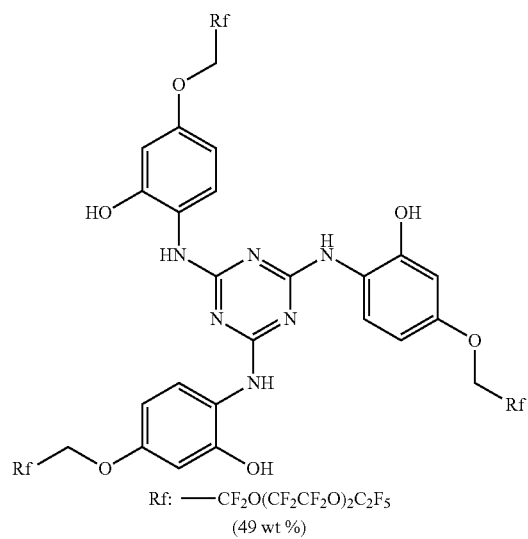
12
Rf: —CF$_2$O(CF$_2$CF$_2$O)$_2$C$_2$F$_5$
(49 wt %)

-continued
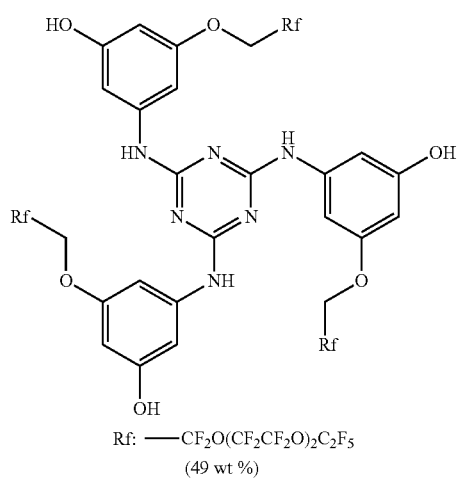
13
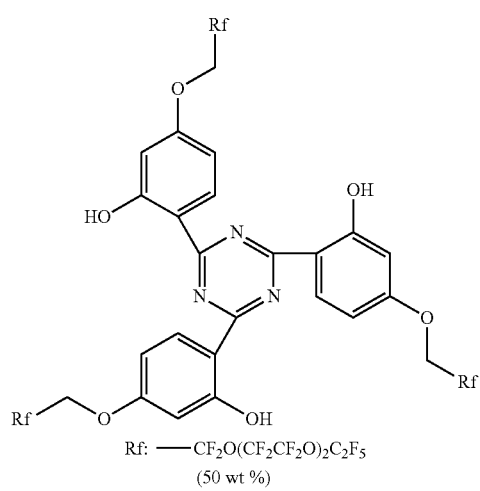
14
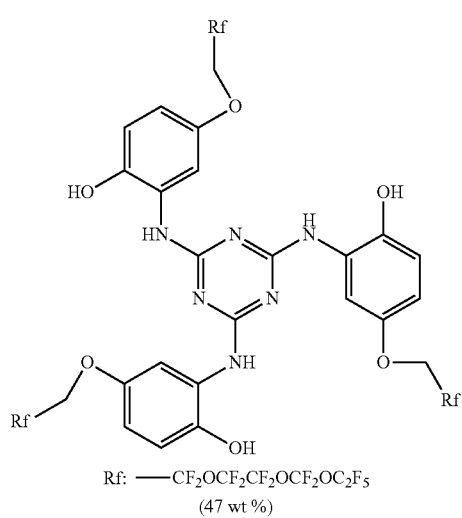
15
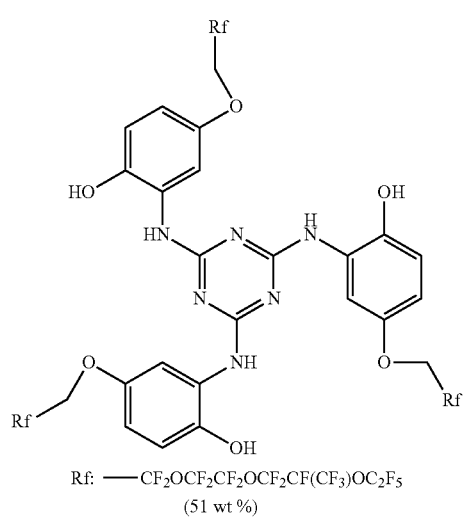
16
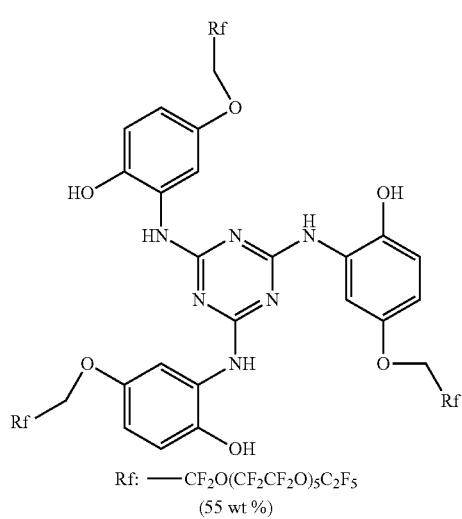
17
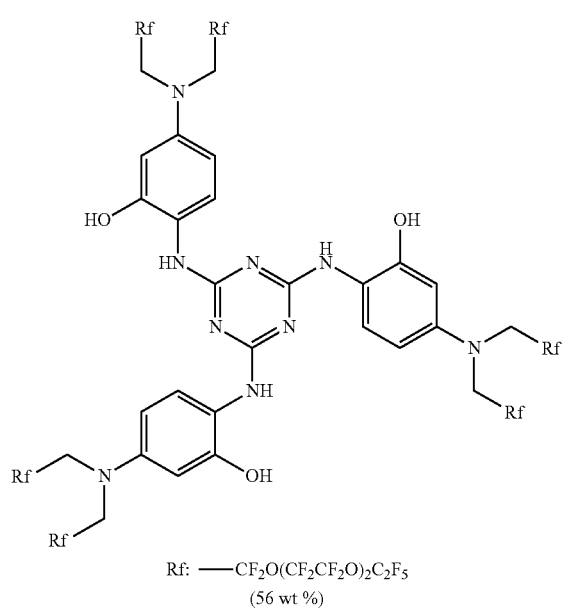
18

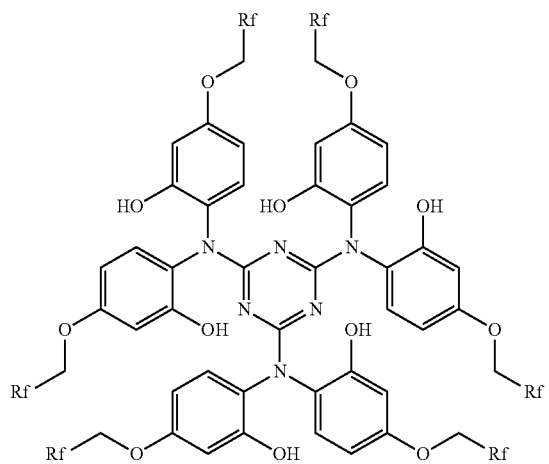
19
Rf: —CF$_2$O(CF$_2$CF$_2$O)$_2$C$_2$F$_5$
(51 wt %)
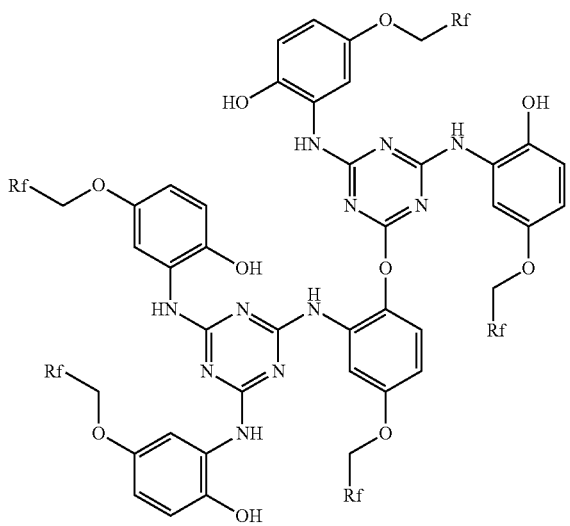
20
Rf: —CF$_2$O(CF$_2$CF$_2$O)$_2$C$_2$F$_5$
(49 wt %)
[Formula 15]
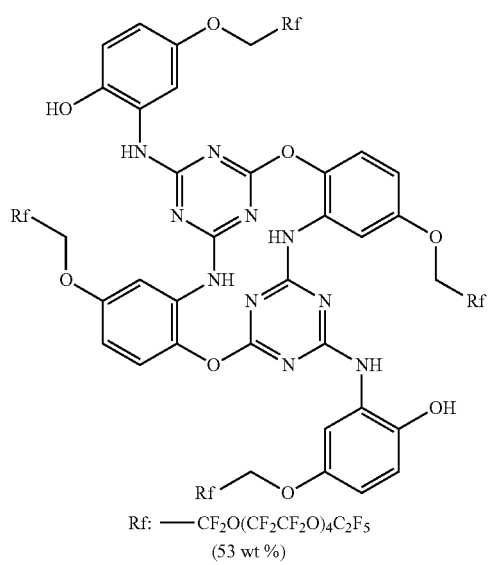
21
Rf: —CF$_2$O(CF$_2$CF$_2$O)$_4$C$_2$F$_5$
(53 wt %)
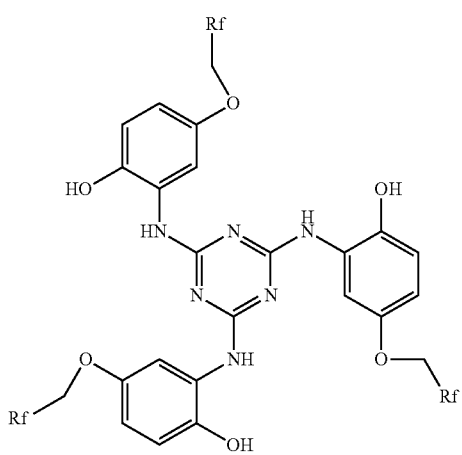
22
Rf: —CF$_2$O(CF$_2$CF$_2$O)$_6$C$_2$F$_5$
(56 wt %)
Chemical Formula: C$_{18}$H$_6$Ar$_6$O$_6$
Molecular Weight: 557.9246

-continued
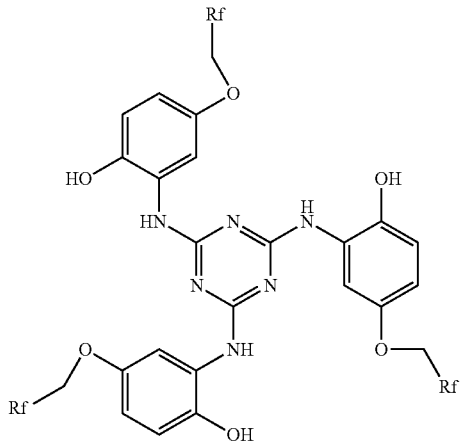
23
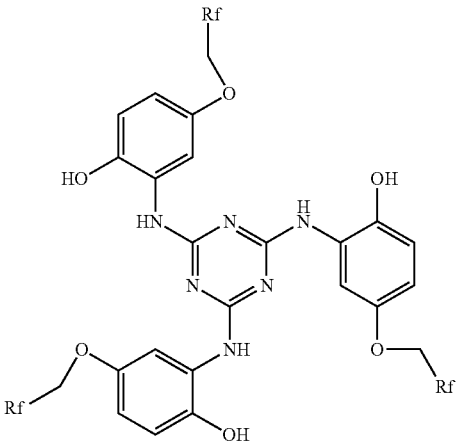
24
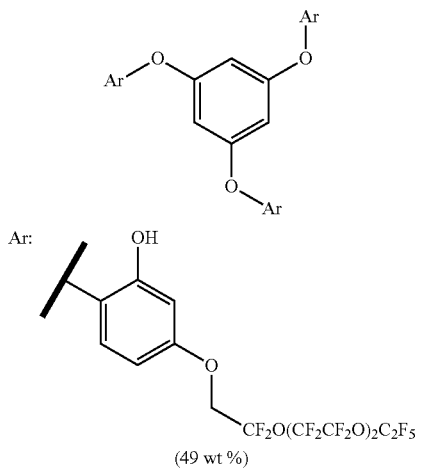
25
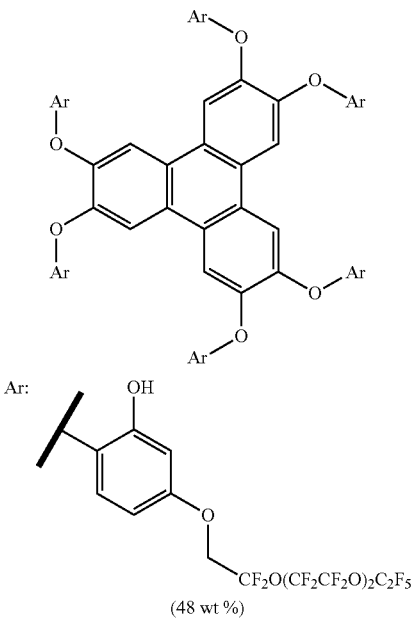
26
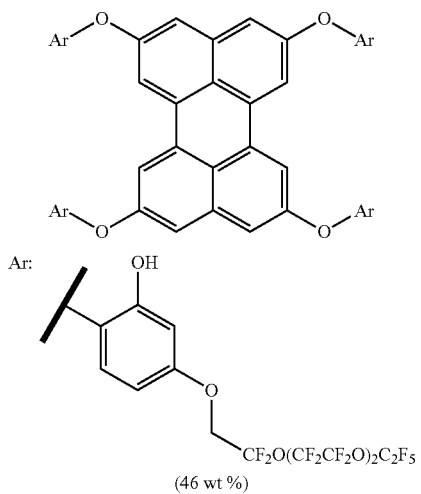
27
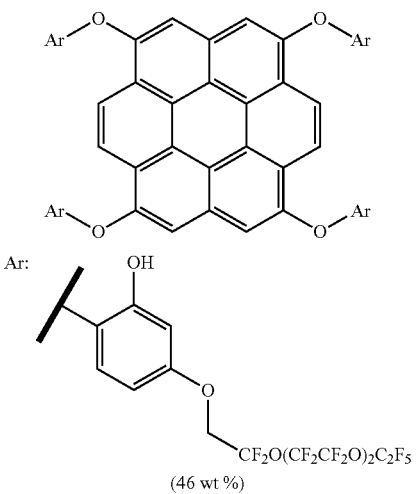
28

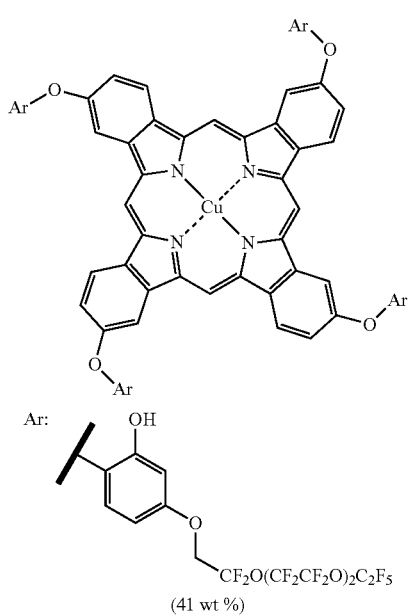
29
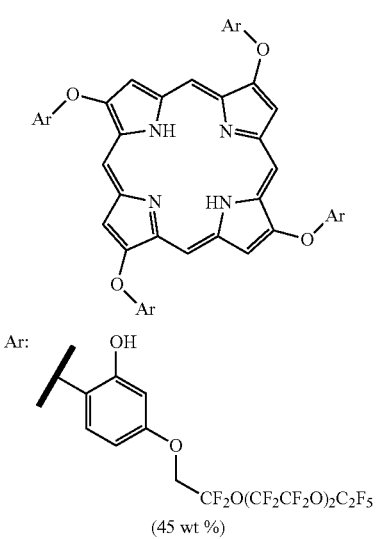
30
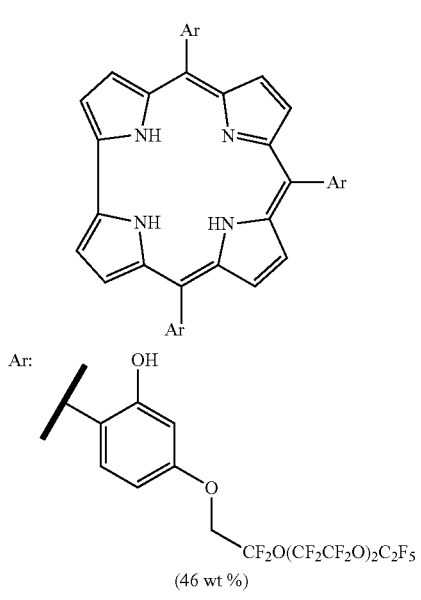
31
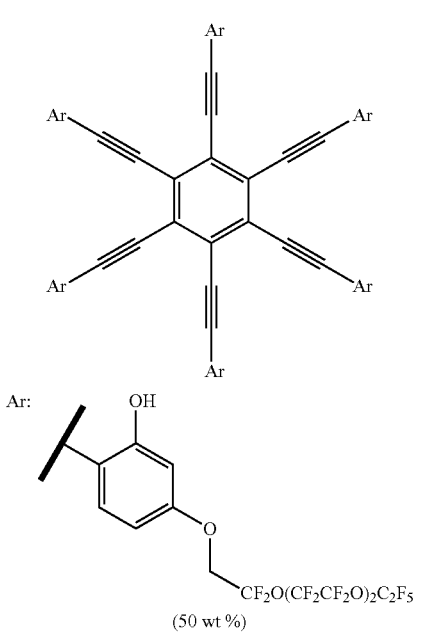
32

-continued
33
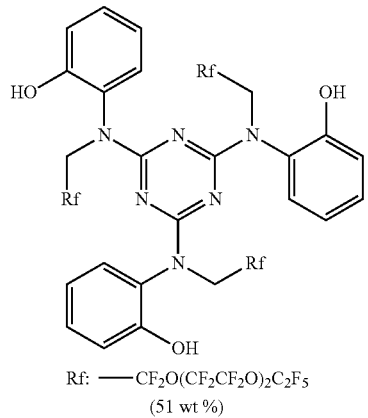
34
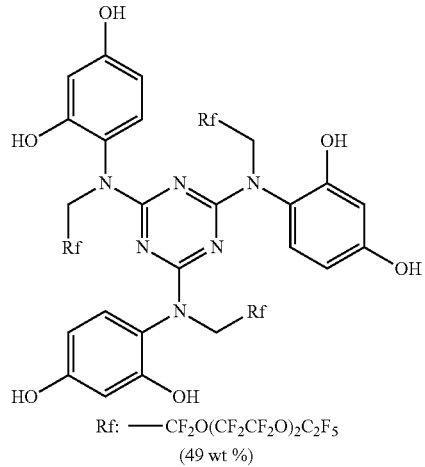
35
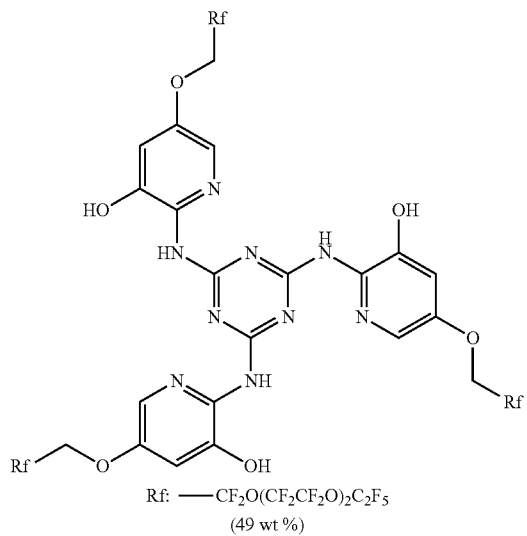
36
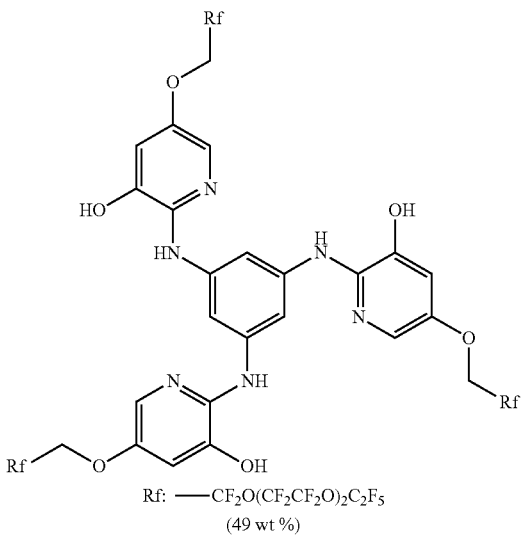
37
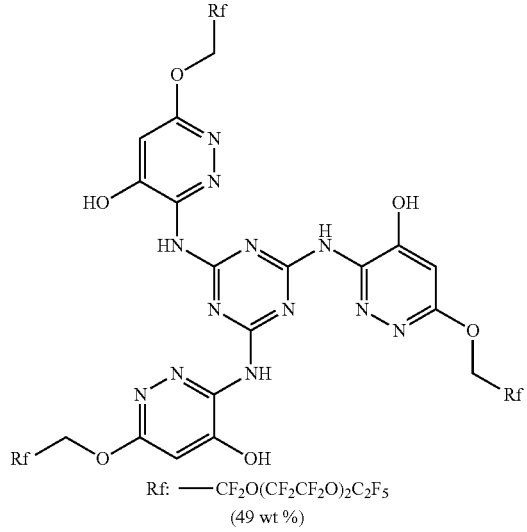
38
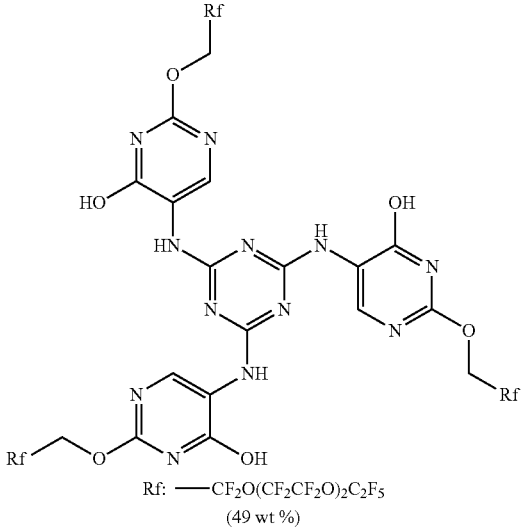

-continued
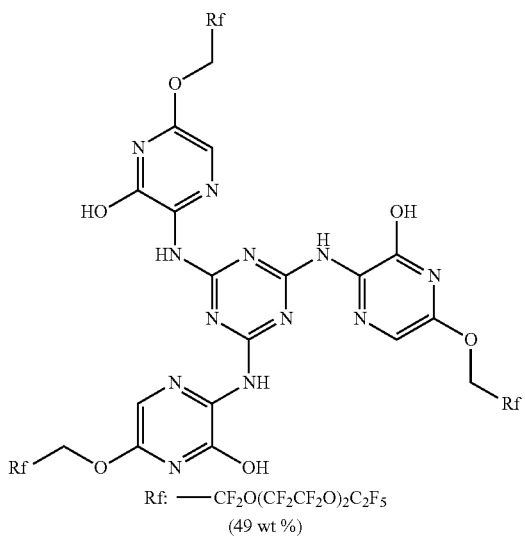
39
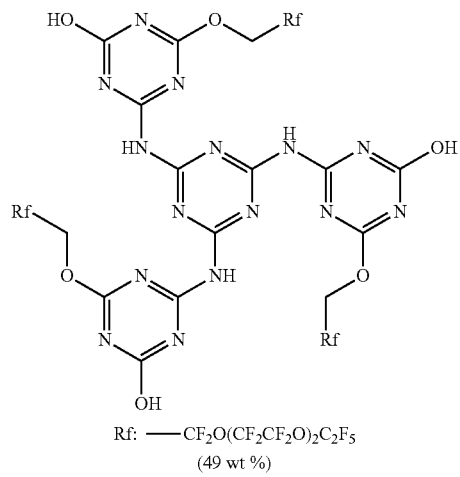
40
[Formula 16]
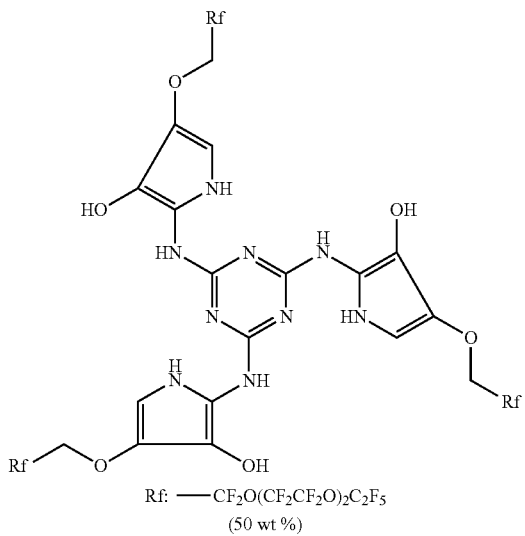
41
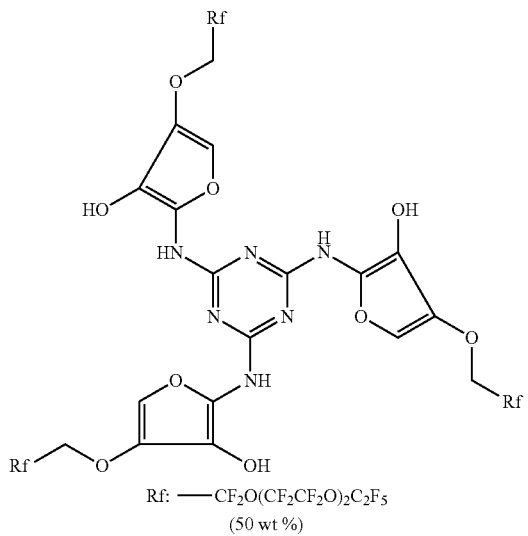
42
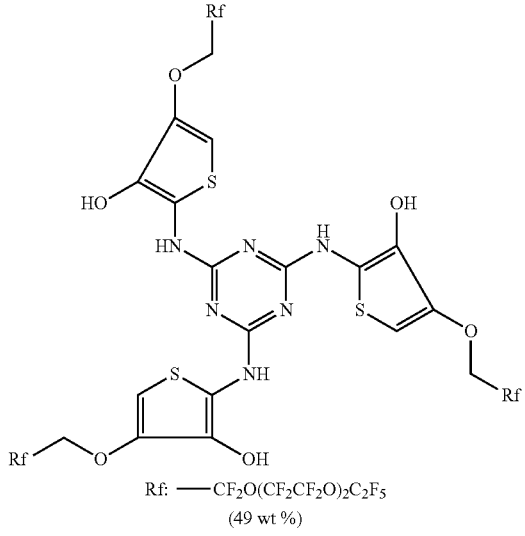
43
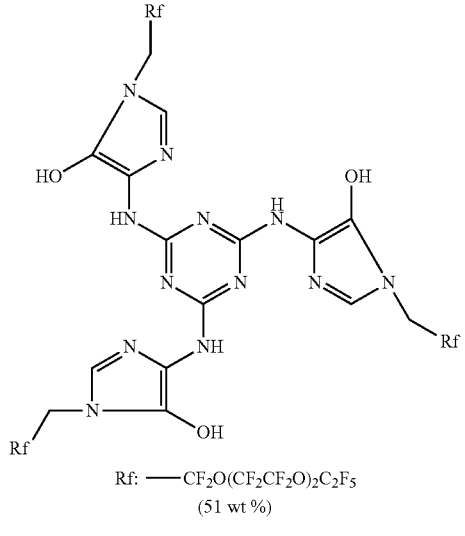
44

-continued
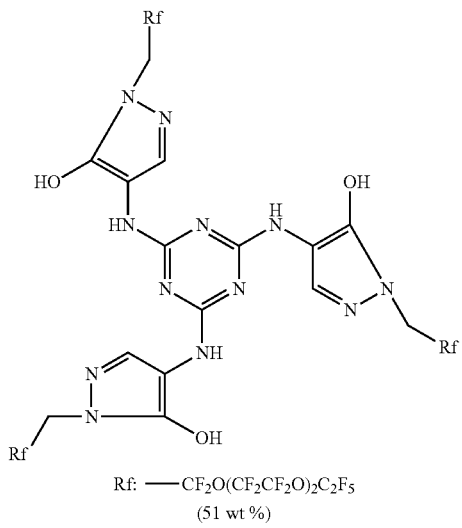
45
Rf: —CF$_2$O(CF$_2$CF$_2$O)$_2$C$_2$F$_5$
(51 wt %)
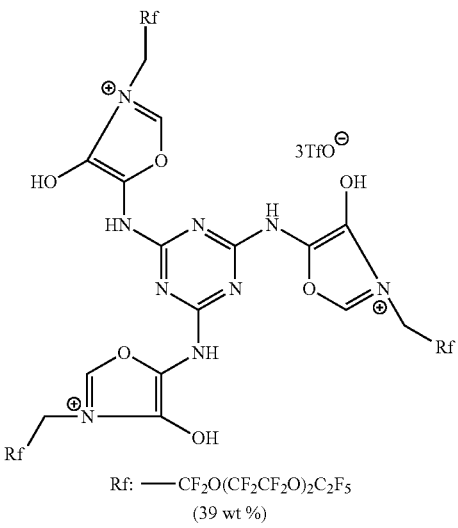
46
3TfO$^\ominus$
Rf: —CF$_2$O(CF$_2$CF$_2$O)$_2$C$_2$F$_5$
(39 wt %)
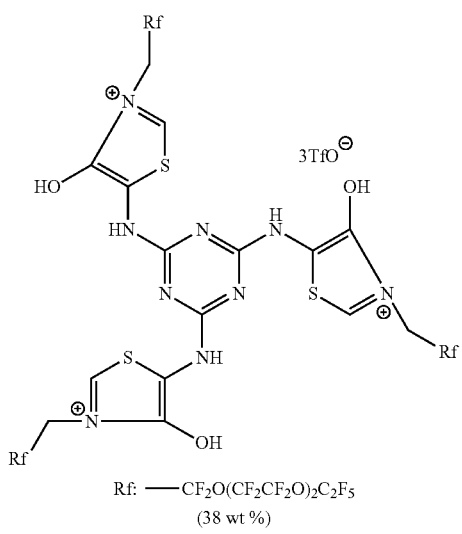
47
3TfO$^\ominus$
Rf: —CF$_2$O(CF$_2$CF$_2$O)$_2$C$_2$F$_5$
(38 wt %)
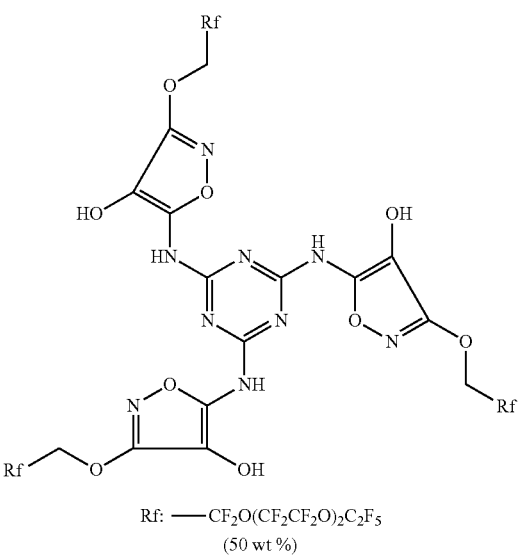
48
Rf: —CF$_2$O(CF$_2$CF$_2$O)$_2$C$_2$F$_5$
(50 wt %)
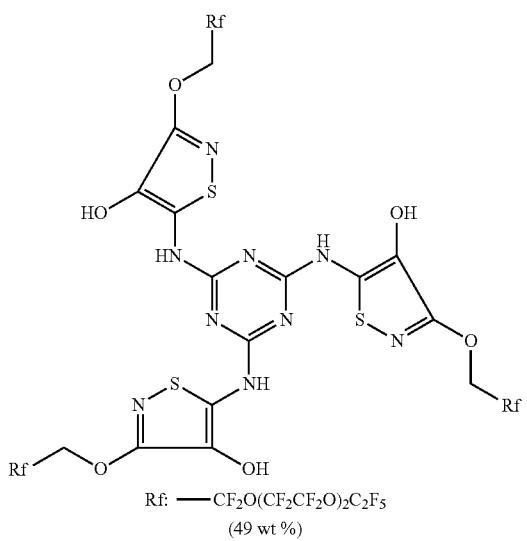
49
Rf: —CF$_2$O(CF$_2$CF$_2$O)$_2$C$_2$F$_5$
(49 wt %)
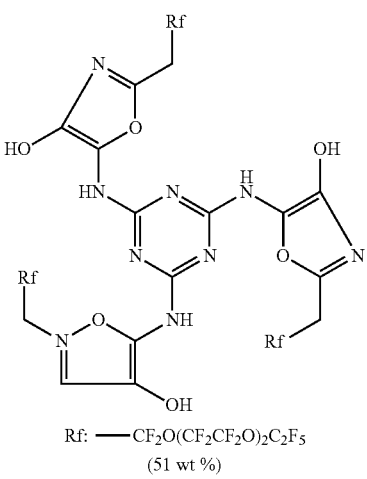
50
Rf: —CF$_2$O(CF$_2$CF$_2$O)$_2$C$_2$F$_5$
(51 wt %)

-continued
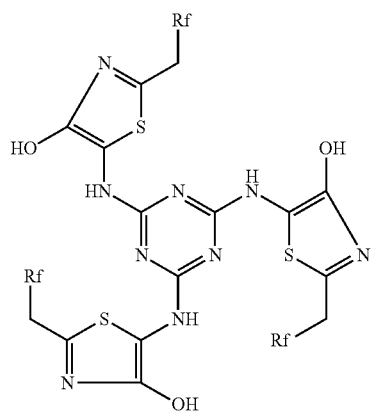
51
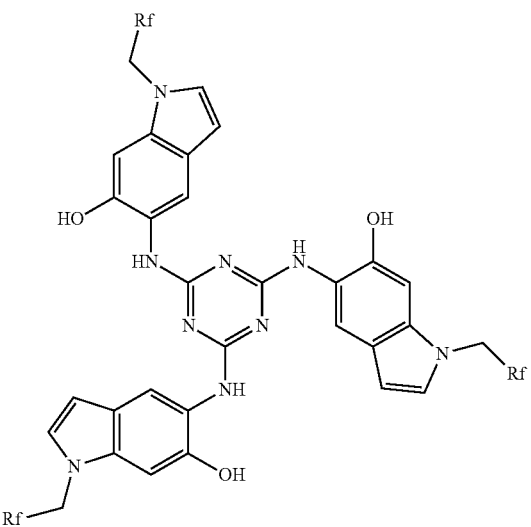
52
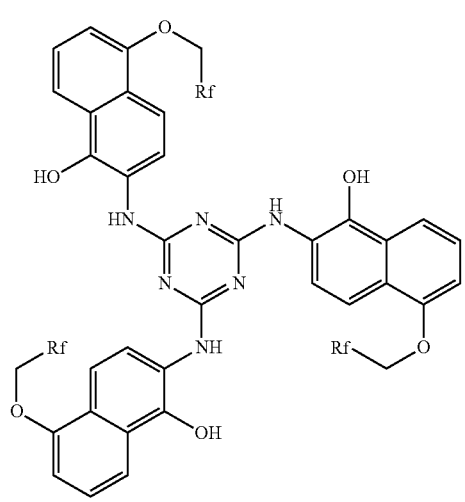
53
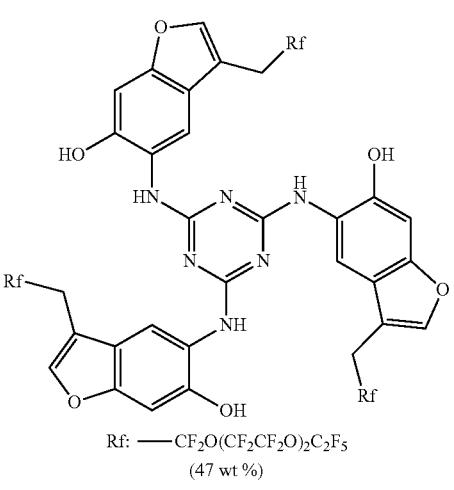
54
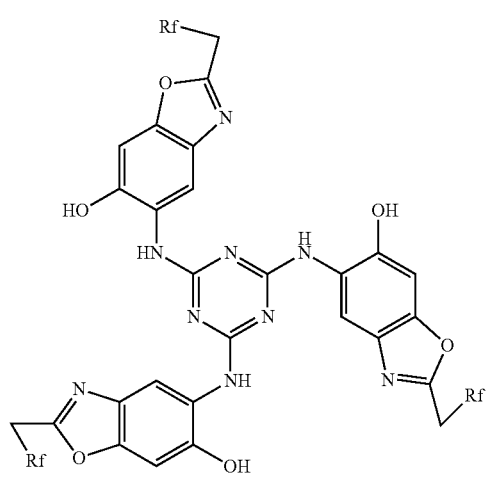
55
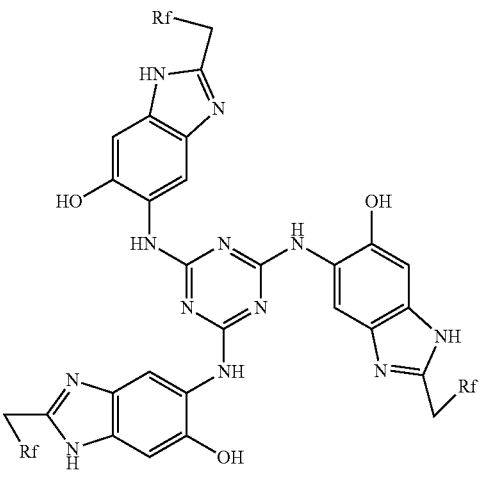
56

[Formula 17]
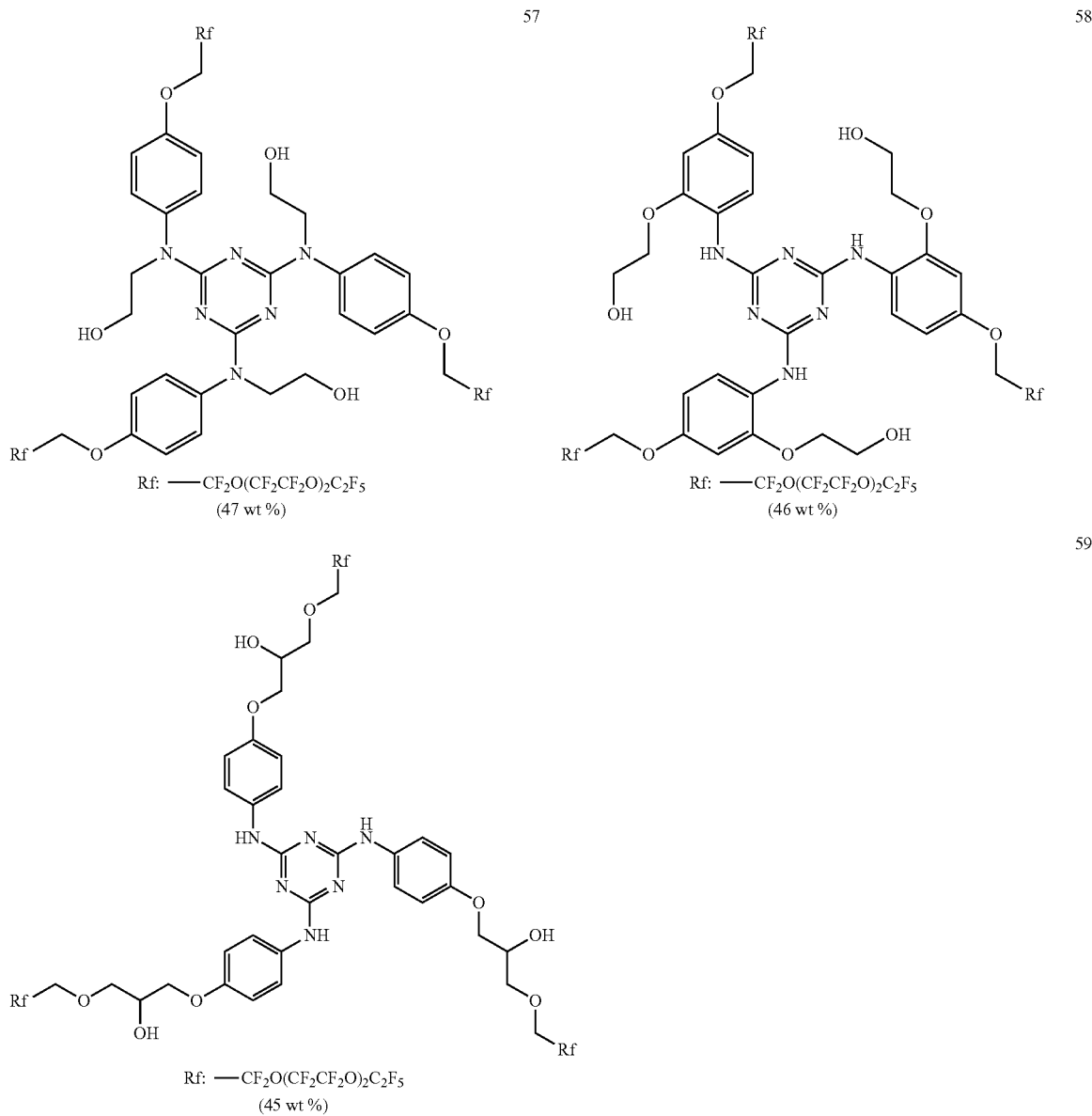

-continued
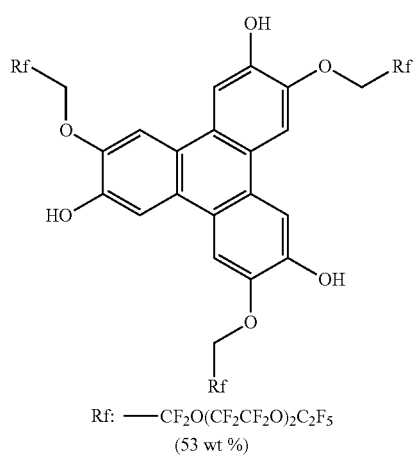
60
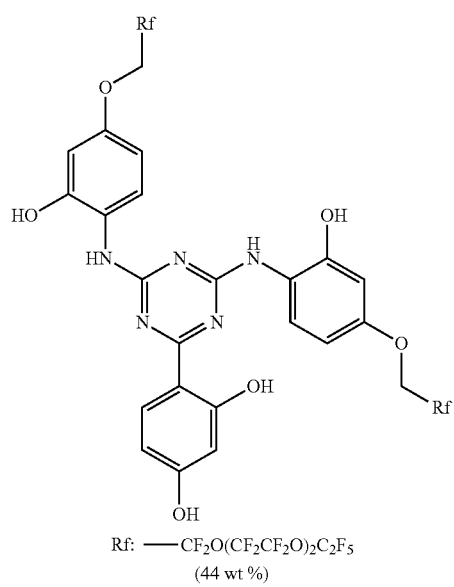
61
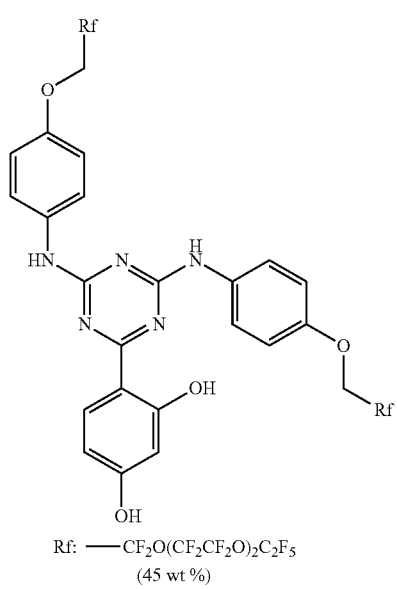
62
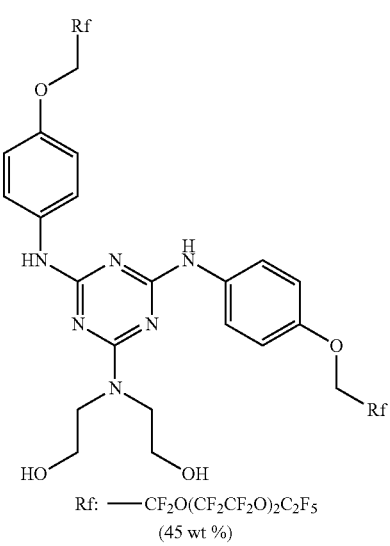
63
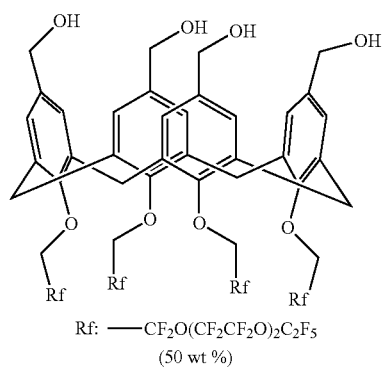
64
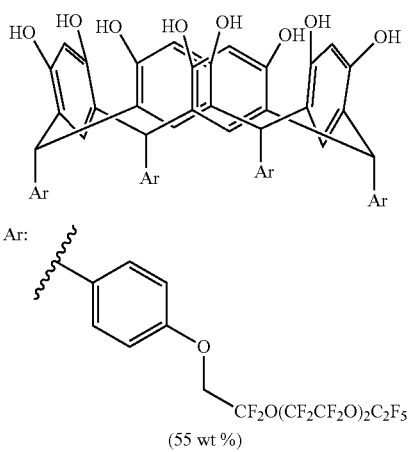
65

-continued
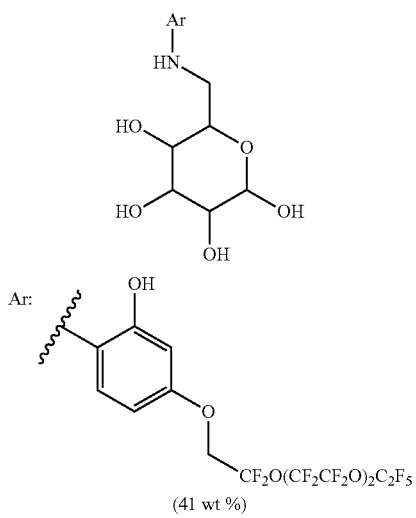
66
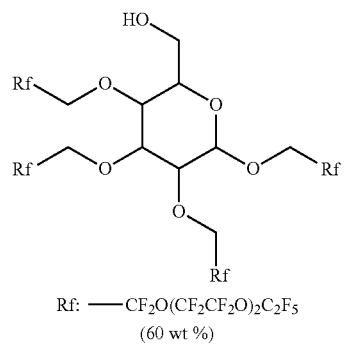
67
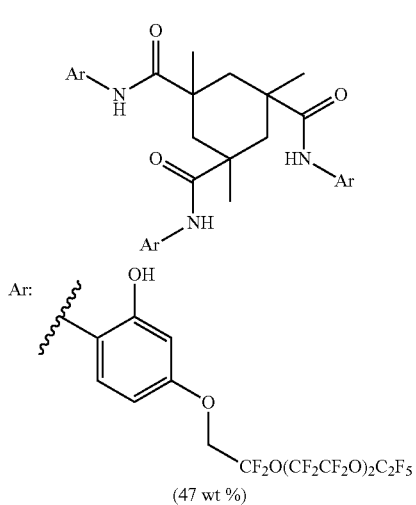
68
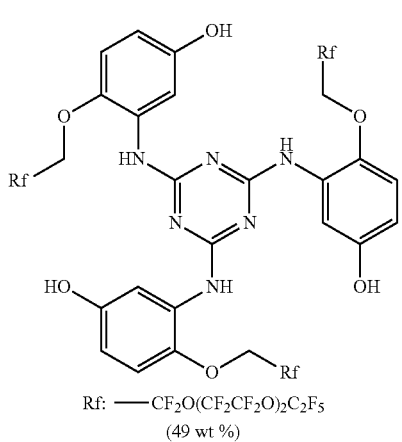
69
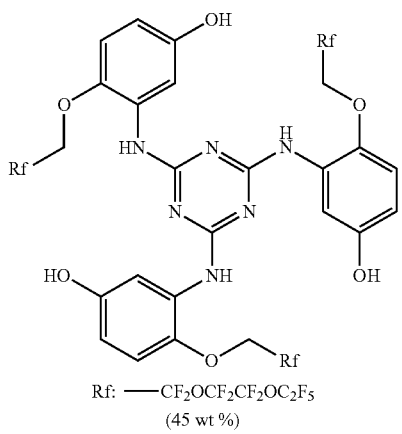
70
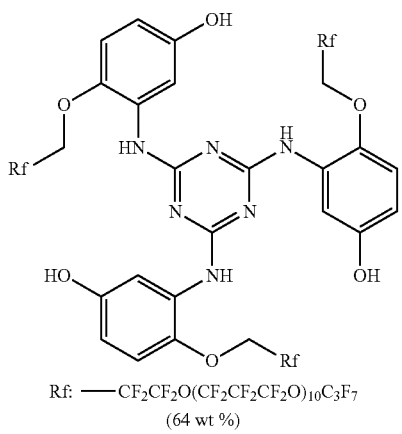
71

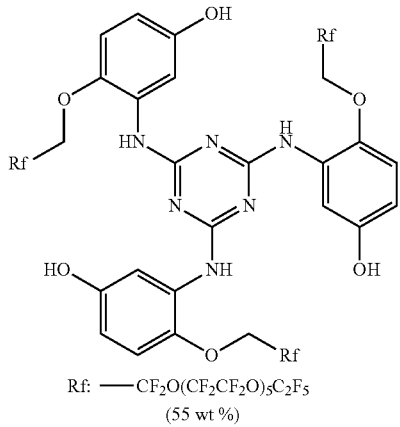
Rf: —CF$_2$O(CF$_2$CF$_2$O)$_5$C$_2$F$_5$
(55 wt %)
[Formula 18]
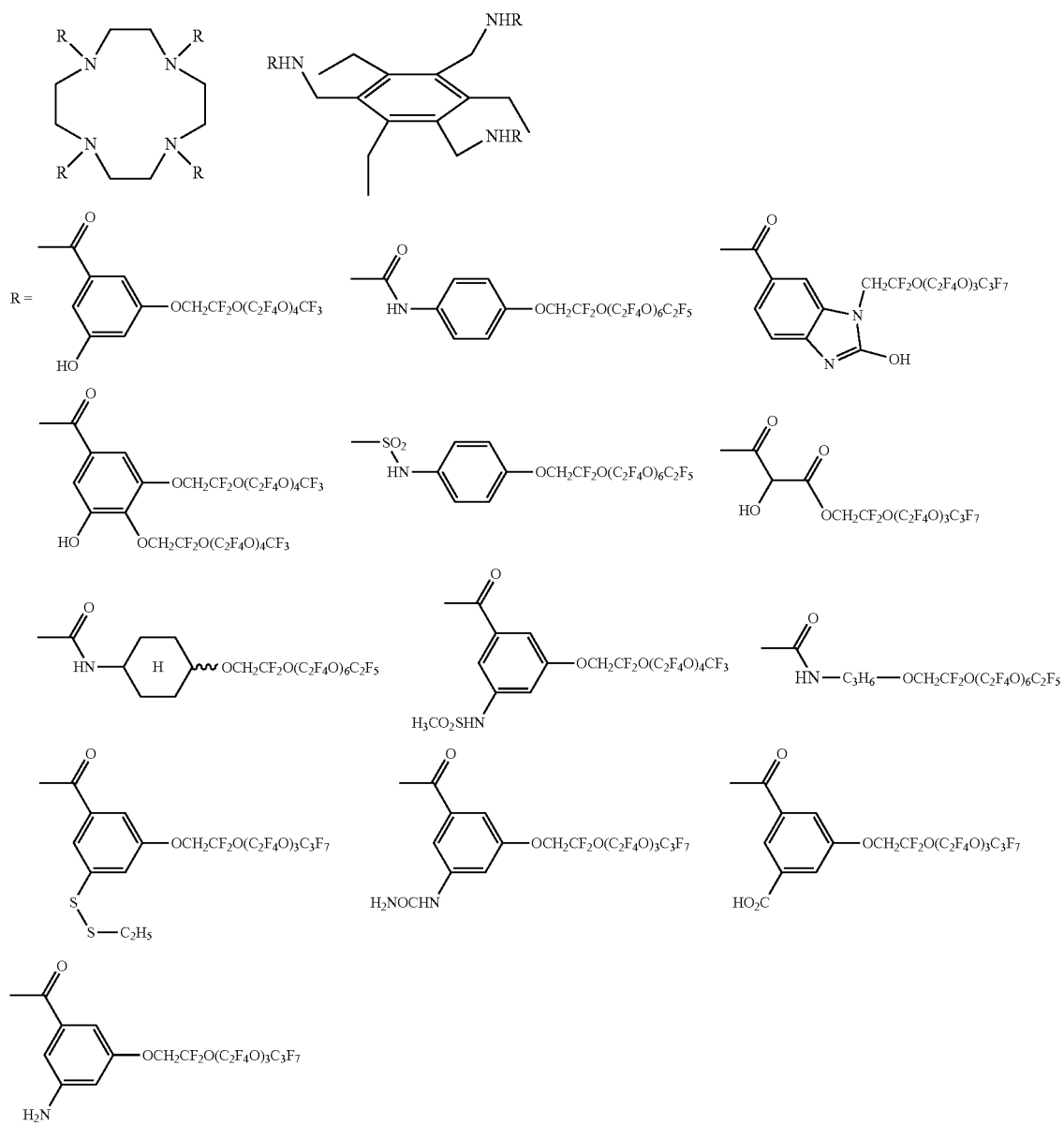

[Formula 19]
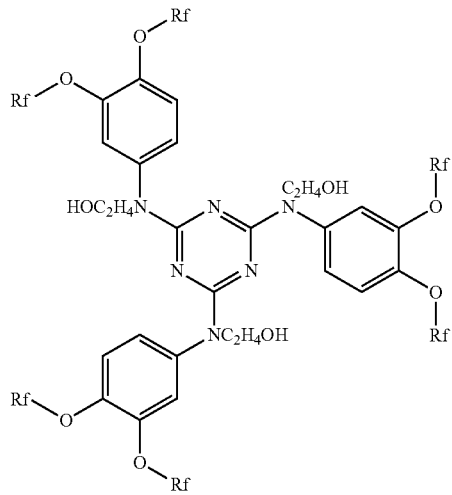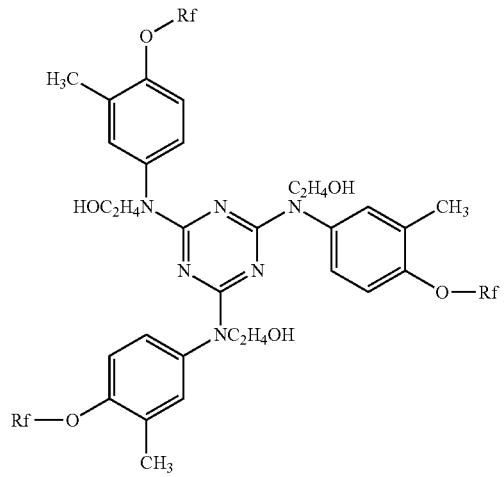
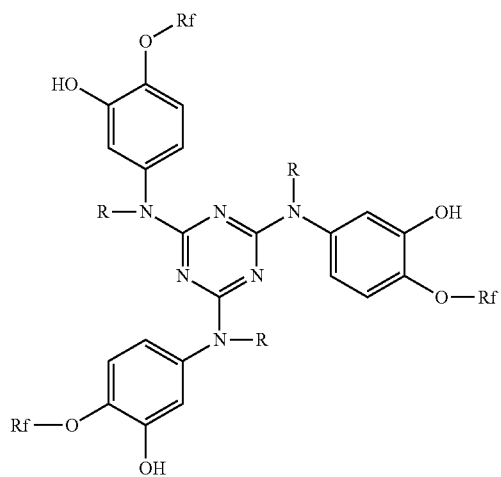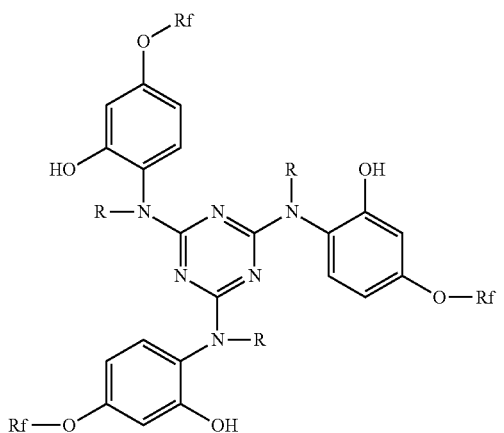
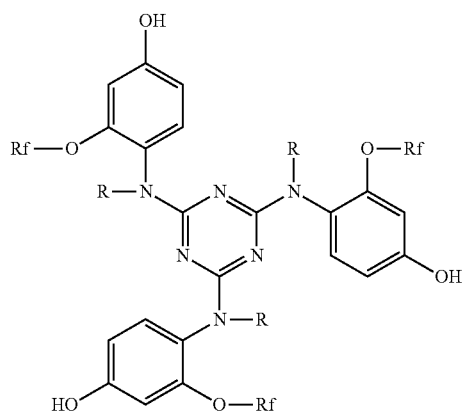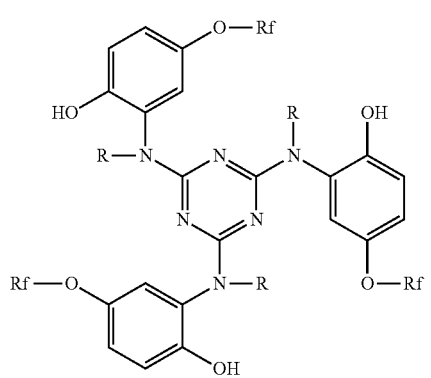

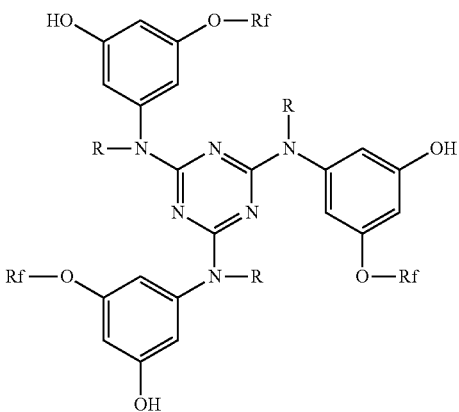
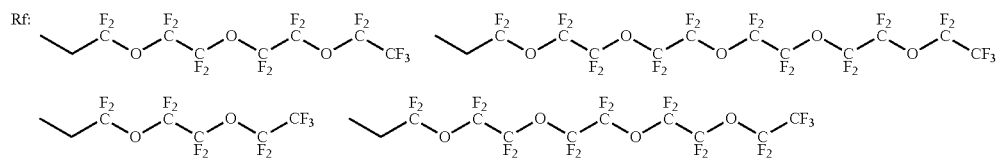
[Formula 20]
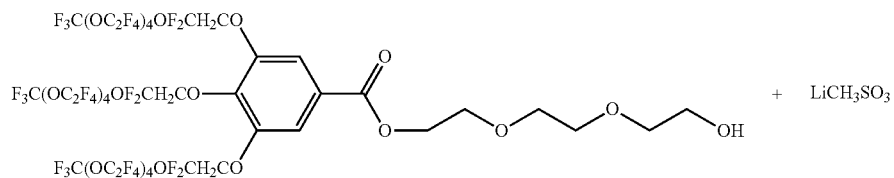
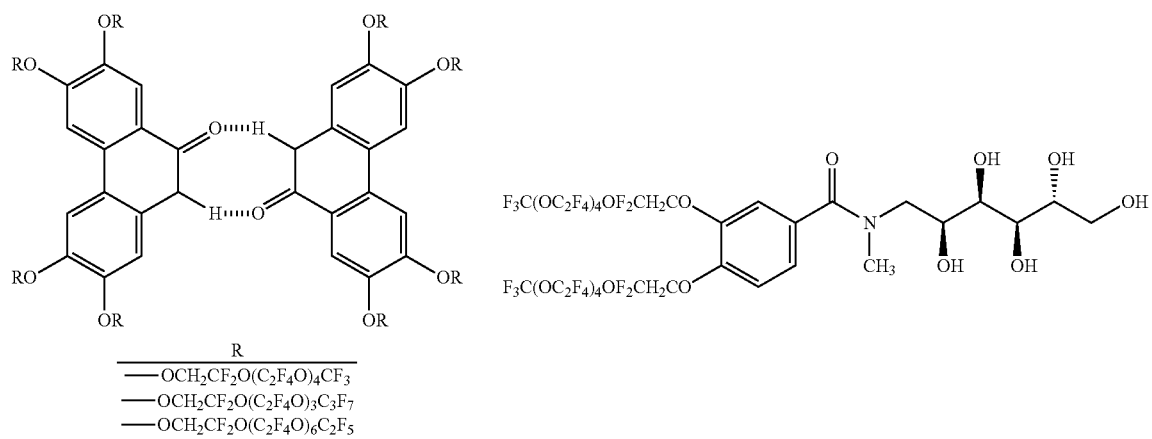

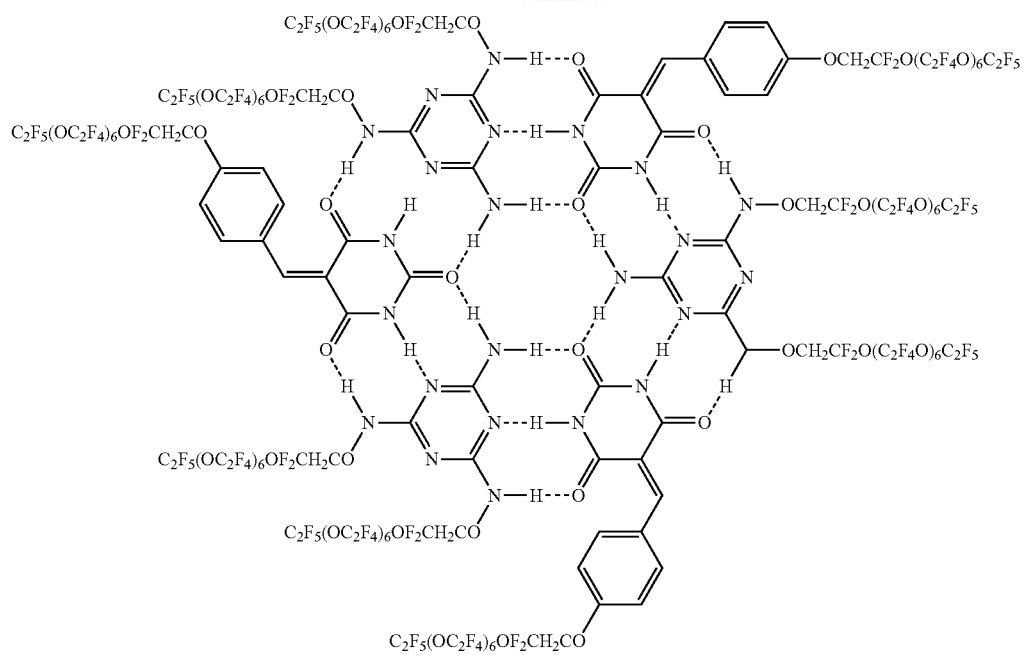
[Formula 21]
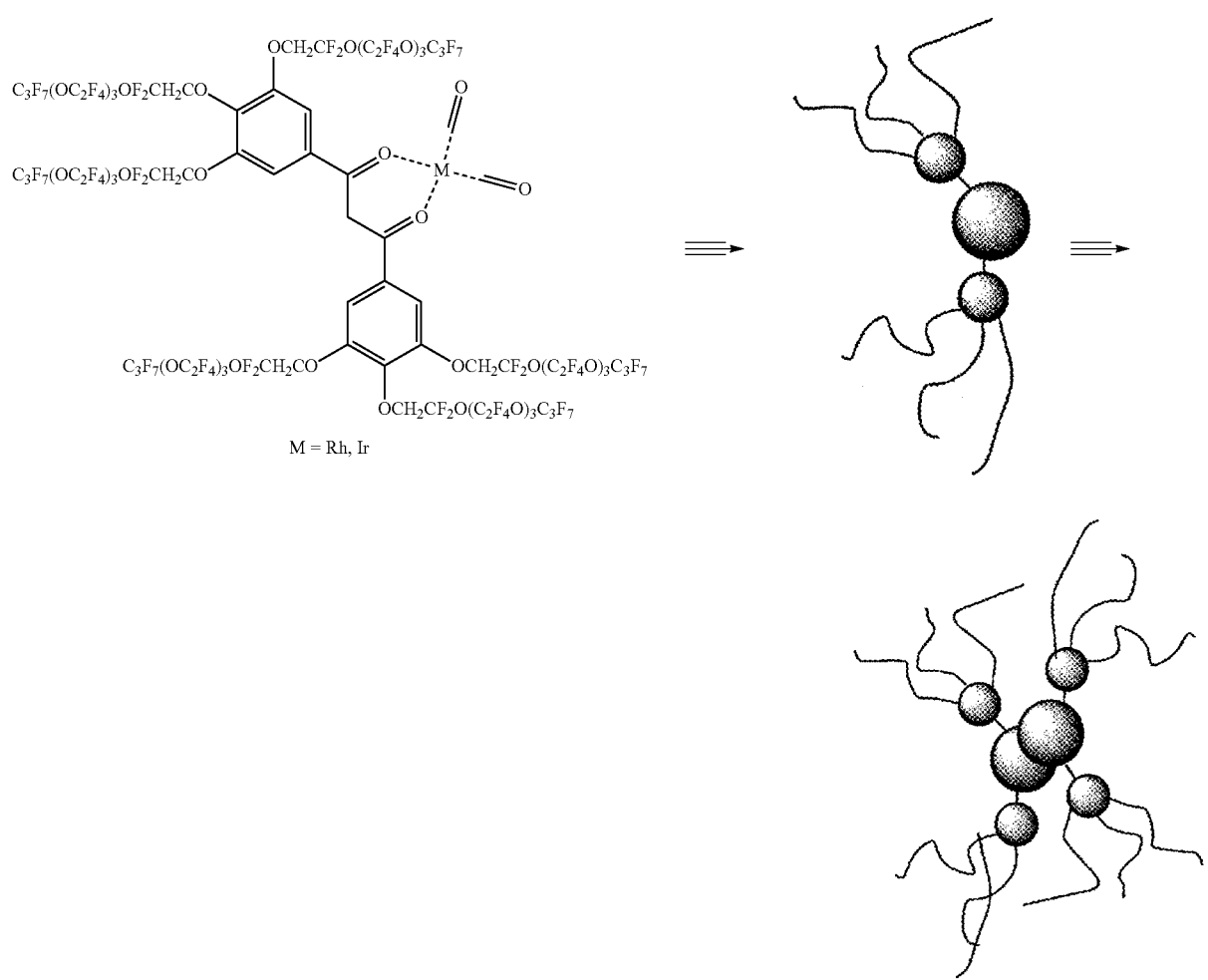
M = Rh, Ir

[Formula 22]

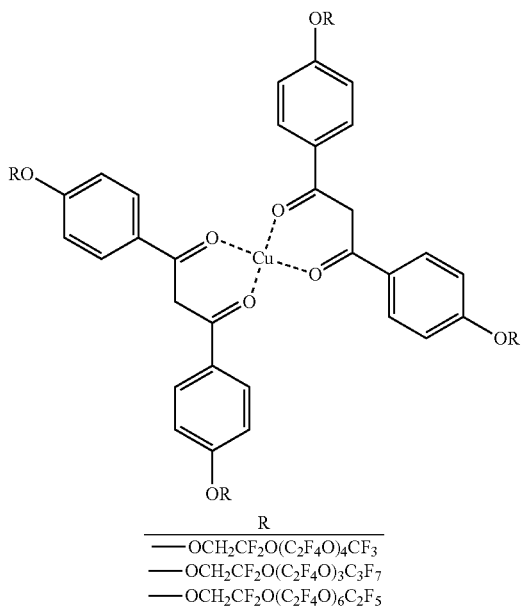

| R |
|---|
| —OCH$_2$CF$_2$O(C$_2$F$_4$O)$_4$CF$_3$ |
| —OCH$_2$CF$_2$O(C$_2$F$_4$O)$_3$C$_3$F$_7$ |
| —OCH$_2$CF$_2$O(C$_2$F$_4$O)$_6$C$_2$F$_5$ |

[Formula 23]

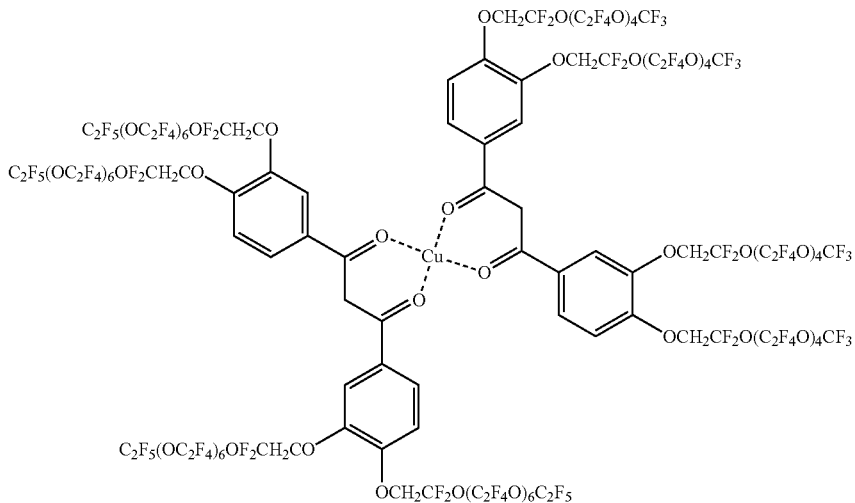

The compound represented by the formula (1) can be synthesized by a combination of various methods. For example, the compound of Formula (4) can be produced by the following method. That is, the basic constituents of the compound of the Formula (1) include a cyclic group in the center, a perfluoroalkyleneoxy group at the terminal, a linking group linking these groups, and an adsorptive group present in the central cyclic group or in the linking group. In respect of multi-point adsorption, it is preferable that a plurality of polar groups be arranged radially with the cyclic group as the center thereof. Accordingly, it is preferable that the adsorptive group be introduced by a predetermined reaction to the linking group which links the cyclic group to the perfluoroalkyleneoxy group at the terminal.

The perfluoroalkyleneoxy group chain (hereinafter, simply referred to as a "fluorine chain" in some cases) at the terminal greatly changes the polarity of the compound. Therefore, it is preferable that the perfluoroalkyleneoxy group chain be introduced around the final step of the compound synthesis. Among the examples of the adsorptive group, if a divalent adsorptive group is used, it is preferable to perform the synthesis reaction by using the polar group as a linking group of the cyclic group and a residue having the fluorine chain. For example, when a compound having a ureylene group as the adsorptive group is synthesized, if a raw material in which a plurality of amino groups binds to the cyclic group is prepared, and a residue having the fluorine chain is allowed to react as isocyanate with the raw material, the compound can be easily synthesized.

When a compound in which the fluorine chain and the linking group bind to each other by ether bonds (an ether bond is a preferable binding form for not being hydrolyzed), an aromatic compound having a hydroxyl group is allowed to react with a triflate of the fluorine chain in general. In this method, for example, when the adsorptive group is a monovalent or divalent polar group that can competitively react with the hydroxyl group of the aromatic compound, it is preferable to protect these groups in advance or to introduce the groups later.

For example, when the compound represented by Formula (4) and including a triazine ring as a center core thereof is synthesized, generally, the side chain is made into an aromatic ring by single bonds, or an aromatic or aliphatic amine or alcohol is allowed to react with cyanuric chloride. Since the polar group exemplified as the adsorptive group becomes competitive over this reaction in some cases, it is preferable to protect the polar group or to introduce the polar group later during the reaction. Though the terminal fluorine chain may be introduced first or later, it is easy to introduce the terminal fluorine chain later in general.

In Formula (4), the compound in which the triazine ring has been substituted with another cyclic group (for example, an aza-crown ether residue such as 12-aza-crown-4) is basically also the same as the aromatic cyclic compound. The aza-crown can be synthesized in the same manner as described above by allowing isocyanate and acid chloride to react with a divalent imino group to form a linking portion.

The lubricant composition of the invention may contain other compounds according to the uses together with the compound represents by Formula (1), within a range that does not diminish the effect of the invention. For example, the lubricant composition of the invention may contain the following compounds (a) to (d), within a range that does not diminish the effect of the invention. The lubricant composition of the invention may contain 2 or more kinds selected from the following compounds (a) to (d). By the addition of the following compounds (a) to (d), the viscosity of the lubricant composition of the invention is reduced, and as a result, friction (for example, in case of a magnetic recording medium, reduction in friction between a head and media) is intended to be further reduced.

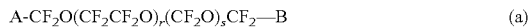

$A\text{-}CF_2O(CF_2CF_2O)_r(CF_2O)_sCF_2\text{--}B$     (a)

[A and B independently represent $OHCH_2-$ or at least one kind of group selected from the following formula; r is any number from 1 to 30; and s is any number from

[Formula 24]

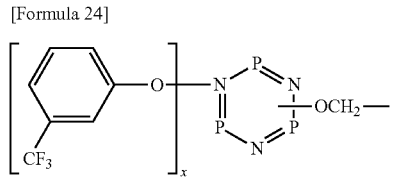

here, x is any number from 1 to 5]

$X-CF_2O(CF_2CF_2O)_m(CF_2O)_nCF_2-Y$     (b)

[X and Y independently represent a group selected from F, $HO(CH_2CH_2O)_tCH_2-$, $HOCH_2CH(OH)CH_2OCH_2-$, $HOOC-$, and a piperonyl group; m is any number from 1 to 60; n is any number from 1 to 60; and t is any number from 1 to 30]

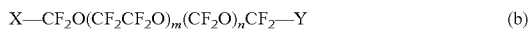

$F[CF(CF_3)CF_2O]_u CF(CF_3)-X'$     (c)

[X' represents F or $COOH-$; and u is any number from 1 to 60]

$F[CF_2CF_2CF_2O]_v CF_2CF_2CH_2-Z$     (d)

[Z represents a group selected from F, $HO-$, and $COOH-$; and v is any number from 1 to 60]

Examples of the compound of the Formula (a) include "Fomblin Z-dol" (manufactured by Solvay Solexis, Inc.), "MORESCO PHOSFAROL A20H" (manufactured by MATSUMURA OIL RESEARCH CORP.), and the like. Examples of the compound of the Formula (b) include "Fomblin Z-03", "Z-dol TX", "Z-tetraol", "Z-DIAC", "AM2001", "AM3001" (all manufactured by Solvay Solexis, Inc.), and the like. Examples of the compound of Formula (c) include "KRYTOX 143", "157FS" (manufactured by DuPont), and the like. Examples of the compound of Formula (d) include "DemnumSA", "DemnumSH" (all manufactured by DAIKIN INDUSTRIES, Ltd.), and the like.

The lubricant composition of the invention may be prepared as a coating liquid including a solvent. In an embodiment in which the lubricant composition is used as a material for a lubricating layer of a magnetic recording medium and the like, it is preferable to prepare the lubricant composition as a coating liquid and to form a thin layer (about 5 Å to 20 Å) by coating the coating liquid on the surface of a substrate or the like. There is no particular limitation on the solvent used for the preparation of the coating liquid. For example, commercially available products such as "Vertrel XF-UP" (manufactured by Du Pont-Mitsui Fluorochemicals Co., Ltd.), "HFE-7100□L" (manufactured by Sumitomo 3M, Ltd.), "HFE-7200" (manufactured by Sumitomo 3M, Ltd.), "AK-225" (manufactured by ASAHI GLASS CO., LTD.), acetone, and 2-butanone can be used. The concentration of the compound of formula in the coating liquid can be determined according to the thickness of the layer to be formed, coating amount, and the like, but the concentration is generally about 0.001% to 0.5% by mass.

2. Film and Laminate

The invention also relates to a film formed of the lubricant composition of the invention. The film of the invention can be formed by preparing the lubricant composition of the invention as a coating liquid and coating the coating liquid on the substrate surface, for example. There is no particular limitation on the coating method, and the film can be formed by a well-known method. Specifically, various coating methods such as a dip coating method, a spin coating method, a dip spin method, and an LB method can be used. The film can also be formed by vacuum deposition. In an embodiment in which the film of the invention is used as a lubricating layer of a magnetic recording medium such as a magnetic recording disk, or as a lubricating layer of a magnetic recording head, a film showing the excellent state of the coated surface is required to be formed as a thin film (for example, a thickness of about 5 Å to 20 Å). For the use, it is preferable to use a dip coating method, a spin coating method, and vacuum deposition, and particularly, the dip coating method is preferable.

Though there is no particular limitation on the solvent used for the preparation of a coating liquid, in the case of dip coating method, it is preferable to use a fluorine-based solvent such as "Vertrel XF-UP" (manufactured by Du Pont-Mitsui Fluorochemicals Co., Ltd.), "HFE-7100□L" (manufactured by Sumitomo 3M, Ltd.), "HFE-7200" (manufactured by Sumitomo 3M, Ltd.) for the preparation, among the above-described solvents.

There is no particular limitation on a substrate for forming the film of the invention, and the substrate can be selected according to the use. An example of the substrate includes a substrate in which at least a portion of the surface thereof includes carbon such as diamond-like carbon as a main material. When the lubricant composition of the invention is coated on the surface of the substrate including carbon such as diamond-like carbon as a main material, it is assumed that in the compound of the Formula (1), the cyclic group X as the center core thereof is oriented horizontally to the substrate surface, and the perfluoropolyether (PFPE) chain as the side chain thereof is oriented vertically. As a result, a particularly high lubricating performance is expected to be expressed. For example, when the lubricant composition (containing a compound that includes —$(OCF_2CF_2)_kOC_nF_{2n+1}$ (here, k+n is 8 or less, and k is 6 or less) at the terminal, as the compound of Formula (1)) of the invention is prepared as a coating liquid by using a fluorine-based solvent, and a film is formed by a dip coating method on the substrate surface formed of diamond-like carbon, in a FT-IR RAS spectrum of the film, a very strong peak attributed to a $CF_3$ group is created near 1260 cm$^{-1}$ (specifically, a range of ±5 cm$^{-1}$). On the other hand, when the same compound is formed as an LB monolayer film, and the FT-IR RAS spectrum is measured in the same manner, a very strong peak attributed to the $CF_3$ group is created near 1260 cm$^{-1}$ (specifically, a range of ±5 cm$^{-1}$). That is, from these results, it can be mentioned that the state of the molecules of the compound of Formula (1) in the film that is formed on the surface formed of carbon is the same as the state of the compound in the LB monolayer film. It is considered that the LB monolayer film is formed in a state in which hydrophilic or polar portions in the molecule face a water surface, and hydrophobic portions of the perfluoropolyether (PFPE) chain converge and are concentrated in an air interface side. Accordingly, the molecules of the compound of Formula (1) in the film that is formed on the surface formed of carbon are also assumed to form a film, in a state in which the PFPE chain is oriented vertically with respect to the substrate surface and concentrated. The uniformity of the molecular state between the LB monolayer film and the compound of Formula (1) can be confirmed from a result that the strength of the peak attributed to the $CF_3$ group near 1260 cm$^{-1}$ is equal to or greater than 50% of the strength of the same peak of the LB monolayer film. The peak strength could be identical in some cases, that is, could be 100%.

In all compounds for a lubricant used for a magnetic recording medium, which are used in the related art and include the PFPE chain, the long PFPE chain is oriented horizontally with respect to the substrate surface. The present inventors consider that such a property is a cause of limiting the performance of the lubricant in the related art. As described above, in the lubricant composition of the invention, the PFPE chain is oriented vertically, and for example, the $CF_3$ group positioned at the terminal of the PFPE chain is present in the uppermost surface of the lubricating layer that contacts a magnetic head. On the other hand, in the compound of the related art in which the PFPE chain is oriented horizontally with respect to the substrate surface, an alkylenoxy fluoride group such as $CF_2CF_2O$ is present on the uppermost surface of the lubricating layer. Compared to this state, a state in which the $CF_3$ group forms the uppermost surface of the lubricating layer is expected to further reduce the surface energy stochastically.

As described above, in the past, there was a problem in that —$OCF_2O$— was degraded in the presence of aluminum oxide (α-$Al_2O_3$) that was a constituent component of a magnetic head. If the PFPE chain is oriented vertically, it is possible to arrange —$OCF_2O$— far away from the magnetic head. In addition, in the lubricant "FOMBLIN Z-TETRAOL" manufactured by Ausimont, Inc., when a polar adsorptive group is present at both terminals of the chain-like PFPE chain, the polar adsorptive group may interact with the adjacent adsorptive groups at the PFPE chain terminal. However, when the adsorptive groups at both terminals of the same molecule interact with each other, if the adsorptive groups are adsorbed onto the substrate surface, the film thickness becomes half of the chain-like PFPE chain at the maximum, and becomes approximately the thickness of —$(CF_2CF_2O)_{10}$ provided that the average molecular weight is 2000. Consequently, concerns over the creation of the lubricating layer looking like a densely wooded plain cannot be dispelled, and it is easy to imagine —$OCF_2O$— being degraded and transferred to the head. Therefore, the lubricating technique in the related art based on the premise of the horizontal orientation of the chain-like PFPE chain can be mentioned as a technique that has limitations for meeting the requirement for making the film thinner.

In respect of the adsorption efficiency, 2 chain-like PFPE chains are arranged in the molecule at the maximum. However, if the molecule has a structure in which 3 or more of the PFPE chains are radially arranged from the center of the molecule, and the adsorptive groups are arranged in the center core or the junction between the PFPE chain and the center core, it is easy to provide the adsorptive group with three or more adsorption points, and the chain-like PFPE chain can be expected to yield a preferable adsorption effect. In this case, by dividing the PFPE chain into a plurality of side chains, the length can be shortened, which is expected to directly lead to thinning of the lubricating layer. Particularly, if the center core is made into a flat cyclic structure, the substrate surface itself serves as an anisotropic field, and the flat cyclic structure, that is, a disk-like structure also has anisotropic property and planarity. Therefore, when the adsorptive group as a polar group is present near the disk surface, it would be enthalpically stable if the adsorptive group is oriented horizontally along the substrate surface. Meanwhile, a fact that the PFPE chain which extends radially from the disk surface also has a water-repellent property and oil-repellent property and tends to extend in a direction away from a polar surface, that is, extend vertically with respect to the substrate surface has been confirmed particularly in the LB monolayer film of a disk-like molecule that includes a hydrophobic side chain (see Kawata, K., The Chemical Record, Vol. 2, pp 59-80 (2002)).

As described above, the molecule of the compound of the Formula (1) can form a film on the surface of a carbon material such as diamond-like carbon, by vertically orienting and concentrating the PFPE chain. As a result, compared to the compound for lubricant in the related art, which includes the PFPE chain oriented horizontally, the compound of Formula (1) is expected to improve in all respects such as lubricating property, adsorptiveness, and durability.

In the use of a laminate that includes a lubricating film on a substrate in which at least a portion of the surface includes carbon as a main material, a magnetic recording medium, a head slider, and the like described later are included.

Hereinafter, as an example, a method of forming a lubricating film formed of the lubricant composition of the invention on a protective layer of a magnetic recording medium will be described.

An example of the method of forming the lubricating film on the protective layer of the magnetic recording medium includes 3 steps such as a pre-treatment step, a coating step, and a post-treatment step.

The purpose of the pre-treatment step is to wash and activate the protective layer surface, and the method thereof is not particularly limited. Examples of the method include UV irradiation, a plasma treatment, and the like. If the protective layer surface is sufficiently cleaned and activated, the pre-treatment step can be omitted.

The coating step is a step of coating the protective layer surface of the magnetic recording medium having undergone the pre-treatment with the lubricant composition, and forming a lubricating layer. The coating method is the same as the example of the film formation method described above. For the lubricating film of the magnetic recording medium, it is required that a film showing an excellent coated surface state is formed into a thin film (for example, a thickness of about 5 Å to 20 Å). In order to meet this requirement, it is preferable to form the film by using a dip coating method, a spin coating method, and vacuum deposition. Particularly, if the dip coating method is used, while a substrate is dipped in coating liquid of the lubricant composition, the compound of the Formula (1) is adsorbed onto and oriented in the protective layer surface. Accordingly, the dip coating method is particularly desirable.

The solvent used for the preparation of the coating liquid is the same as the solvent described above. To the coating liquid, other compounds (for example, other fluorine-based lubricants and the like) may be added according to the use, within a range that does not diminish the effect of the invention.

The purpose of the post-treatment step is to promote the lubricant composition to be adsorbed onto the protective layer surface. There is no particular limitation on the post-treatment method, but annealing, UV irradiation, and the like are preferable as the method. As an annealing condition, a temperature of 50° C. to 150° C. is preferable, and in a case of UV irradiation, it is preferable to use a UV lamp including light of wavelengths of 185 nm and 254 nm.

3. Magnetic Recording Medium

The lubricant composition of the invention is useful as a lubricant composition for a magnetic recording medium.

Hereinafter, the magnetic recording medium of the invention that uses the lubricant composition of the invention will be described.

The lubricant composition of the invention is suitable as a material of a lubricating layer of a magnetic recording medium such as a magnetic recording disk and a magnetic tape. In the present specification, the "magnetic recording medium" includes all of a magnetooptical recording medium such as MO that concurrently uses magnetism and light, and a heat-assisted type recording medium that concurrently uses magnetism and heat, in addition to a hard disk, a Floppy (registered trademark) disk, a magnetic tape, and the like that only use magnetism for recording and reading information.

FIG. 1 is a schematic cross-sectional view of an example of a magnetic recording disk which is an embodiment of the magnetic recording medium of the invention. The relative relationship between the thicknesses of the respective layers may not match with the relationship of the actual magnetic recording disk in some cases. The magnetic recording disk shown in FIG. 1 includes a substrate 1 formed of an aluminum alloy or the like, and a plating film 2 of Ni—P or the like coated on the substrate 1 as a hard base layer. The magnetic recording disk also includes a base film layer 3 that is formed on the plating film 2 by sputtering or the like and is a metal film such as Cr; a magnetic recording layer 4 that is formed of a metal alloy such as a Co—Cr—Ta alloy; and a protective film layer 5 that is formed by the deposition of carbon such as diamond-like carbon. On the protective film layer 5, a lubricating layer formed of the lubricant composition of the invention is formed. The protective film layer 5 and the lubricating layer 6 reduce the abrasion damage of a disk and a head, which is caused, for example, when the magnetic head and the disk perform contact-slide at a high speed. Since the lubricating layer 6 is formed of the lubricant composition of the invention, the lubricating layer 6 is excellent in terms of adsorptiveness with respect to the protective layer and the surface smoothness, and shows a superior lubricating property. Consequently, head contamination is reduced, and the abrasion damage caused during the contact-slide between the disk and head is also reduced, whereby a magnetic recording disk with high reliability can be obtained.

The lubricant composition of the invention is also useful for forming a lubricating film of DTM (Discrete Track Media) and BPM (Bit Patterned Media). The lubricant composition of the invention has characteristics such as high viscosity and low vapor pressure property. Therefore, particularly in a process in which a concave-convex shape of the surface is not refilled, the lubricant composition can reduce the transfer of a non-adsorptive lubricant that excessively accumulates in a concave portion to the head, and the movement of the non-adsorptive lubricant to the surface of a data portion.

The lubricant composition of the invention is also useful as a lubricating film for heat-assisted recording of assisting energy and microwave-assisted recording. Particularly, since the lubricant composition of the invention has excellent heat durability, the lubricant composition is useful as a lubricating film for heat-assisted magnetic recording.

4. Head Slider

The invention also relates to a head slider that is provided with a magnetic head and includes a lubricating film formed of the lubricant composition of the invention on at least a portion of the surface. If the lubricating film is formed on the magnetic head surface, it is possible to reduce the friction force caused when the head contacts the disk. In addition, the compound of Formula (1) contained in the lubricant composition of the invention has a property in which the compound can coat the substrate surface with high density. Accordingly, the reduction in the contaminant attachment to the head is expected.

As a method of forming the lubricating film formed of the lubricant composition of the invention on the head slider surface, it is possible to use the above-described method of forming the lubricating film which is formed on the protective layer of the magnetic recording medium, and the preferable embodiment thereof is also the same. Moreover, the film thickness is also about the same as the film thickness of the lubricating film formed on the magnetic recording medium.

Between the head slider surface and the lubricating film formed of the lubricant composition of the invention, a protective layer may be formed. Similar to the protective layer of the magnetic recording medium, the protective layer is preferably formed by the deposition of carbon such as diamond-like carbon. The molecules of the compound of Formula (1) which is contained in the lubricant composition of the invention are preferable since the molecules show high adsorptiveness with respect to a surface formed of the material, and the PFPE chain can be oriented vertically and form a film by being concentrated, as described above.

EXAMPLE

Hereinafter, the invention will be described in more detail by using examples. The materials, reagents, ratios, operations, and the like shown in the following examples can be appropriately changed as long as the change does not depart from the scope of the invention. Consequently, the range of the invention is not limited to the following examples.

1. Synthesis of Compound of Formula (1)

Synthesis Example of Example Compound 1

Ester Reduction:
70 g of sodium boron hydride (manufactured by Sigma-Aldrich Co. LLC.), 1 L of tetrahydrofuran, and 0.5 L of distilled water were introduced to a 3 L three-neck flask, and 400 g of methyl-perfluoro-3,6,9-trioxaundecanoate (manufactured by Exfluor Research Corporation) was added thereto under ice cooling. Thereafter, the resultant was stirred for 2 hours at room temperature, followed by ice cooling, and 0.5 L of 4 mol/L hydrochloric acid water was added thereto. Subsequently, an organic layer was extracted, and the solvent was distilled away under reduced pressure, thereby obtaining 340 g of 1H,1H-perfluoro-3,6,9-trioxaundecanol.

Triflylation:
320 g of 1H,1H-perfluoro-3,6,9-trioxaundecanol, 3 L of methyl chloride, and 160 mL of triethylamine were introduced to a 5 L three-neck flask, and 150 mL of trifluoromethanesulfonic acid anhydride (manufactured by Tokyo Chemical Industry Co., Ltd.) was added thereto at low temperature. Thereafter, the resultant was stirred for 10 minutes at the same temperature, and 1 L of 1 mol/L hydrochloric acid water was added thereto. Subsequently, an organic layer was extracted, and the solvent was distilled away under reduced pressure. The obtained residue was purified by distillation under reduced pressure, thereby obtaining 360 g of 1H,1H-perfluoro-3,6,9-trioxaundecanyl trifluoromethanesulfonate.

Alkylation:
340 g of 1H,1H-perfluoro-3,6,9-trioxaundecanyl trifluoromethanesulfonate, 80 g of 2-hydroxybenzoxazole, and 100 mL of N,N-dimethylacetamide were introduced to a 500 mL three-neck flask, and 120 g of potassium carbonate was added thereto at room temperature. Thereafter, the resultant was stirred for 1 hour at 120° C., and then potassium carbonate was removed by filtration. The resultant was washed and extracted with 100 mL of 1 mol/L hydrochloric acid water, and the solvent was distilled away under reduced pressure. Hexane was added to the obtained residue to perform extraction, and the solvent was distilled away under reduced pressure, thereby obtaining 300 g of 2-(1H,1H-perfluoro-3,6,9-trioxaundecanoxy)benzoxazole.

Acid Hydrolysis:
300 g of 2-(1H,1H-perfluoro-3,6,9-trioxaundecanoxy)benzoxazole was introduced to a 2 L three-neck flask, and 300 mL of ethanol and 300 mL of concentrated hydrochloric acid were added thereto at room temperature. Thereafter, the resultant was stirred for 2 hours at 100° C., and 300 g of sodium acetate and 1 L of water were added thereto, followed by extraction by using an organic solvent. Subsequently, the solvent was distilled away under reduced pressure, thereby obtaining 260 g of 2-hydroxy-4-(1H,1H-perfluoro-3,6,9-trioxaundecanoxy)aniline.

Triallylmelamination:
260 g of 2-hydroxy-4-(1H,1H-perfluoro-3,6,9-trioxaundecanoxy)aniline, 700 mL of N,N-dimethylacetamide, and 28 g of cyanuric chloride (manufactured by Tokyo Chemical Industry Co., Ltd.) were introduced to a 2 L three-neck flask, and 70 g sodium acetate and 140 mL of water were added thereto under ice cooling. Thereafter, the resultant was stirred for 10 hours at 50° C. and then washed and extracted by using 1 mol/L of hydrochloric acid water, and the solvent was distilled away under reduced pressure. The obtained residue was washed with methylene chloride, thereby obtaining 140 g of Example Compound 1.

Synthesis Example of Example Compound 2

Ester Hydrolysis:
400 g of methyl perfluoro-3,6,9-trioxaundecanoate (manufactured by Exfluor Research Corporation) and 600 mL of methanol were introduced to a 3 L three-neck flask, and 50 g of potassium hydroxide and 300 mL of water were added thereto under ice cooling. Thereafter, the resultant was stirred for 1 hour at room temperature, and 1 mol/L of hydrochloric acid water were added thereto by 0.6 L under ice cooling, followed by extraction by using an organic solvent. Thereafter, the solvent was distilled away under reduced pressure, thereby obtaining 400 g of perfluoro-3,6,9-tiroxaundecanoic acid.

Dehydrating Condensation:
330 g of perfluoro-3,6,9-tiroxaundecanoic acid, 3 L of acetone, and 108 g of 2-aminobenzoxazole were introduced to a 5 L three-neck flask, and 1-ethyl-3-(3-dimethylaminopropyl)carbodiimide hydrochloric acid salt (manufactured by Tokyo Chemical Industry Co., Ltd.) and 10 g of 4-dimethylaminopyridine were added thereto under ice cooling. Thereafter, the resultant was stirred for 30 minutes at room temperature, and then 1 L of 1 mol/L hydrochloric acid water was added thereto. The resultant was extracted using an organic solvent, and the solvent was distilled away under reduced pressure. The obtained residue was purified by silica gel column chromatography (3 kg of silica gel (Wakogel-C200), ethyl acetate/hexane=¼), thereby obtaining 360 g of benzoxazolyl perfluoro-3,6,9-trioxaundecanamide.

Acid Hydrolysis and Triallylmelamination:
Example Compound 2 was synthesized in the same manner, except that the 2-(1H,1H-perfluoro-3,6,9-trioxaundecanoxy)benzoxazole was changed to benzoxazolyl perfluoro-3,6,9-trioxaundecanamide in the synthesis method of Example Compound 1.

Synthesis Example of Example Compound 3

Example Compound 3 was synthesized in the same manner, except that methyl perfluoro-3,6,9-trioxaundecanoate was changed to methyl perfluoro-3,6-dioxadecanoate (manufactured by Exfluor Research Corporation) in the synthesis example of Example Compound 1.

Synthesis Example of Example Compound 4

Example Compound 4 was synthesized in the same manner, except that methyl perfluoro-3,6,9-trioxaundecanoate was changed to methyl perfluoro-3,6-dioxadecanoate (manufactured by Exfluor Research Corporation) in the synthesis example of Example Compound 2.

Synthesis Example of Example Compound 17

Example Compound 17 was synthesized in the same manner, except that methyl perfluoro-3,6,9-trioxaundecanoate was changed to methyl perfluoro-3,6,9,12,15,18-hexaoxae-icosanoate (manufactured by Exfluor Research Corporation) in the synthesis example of Example Compound 1.

2. Production of Magnetic Disk for Test

Example 1

A hard disk having the configuration as shown in FIG. 1 was produced. Specifically, the disk was produced in the following manner.

A Ni—P plating film 2 was coated on an aluminum alloy substrate 1 as a hard base layer, and then Cr as a base film layer 3, a Co—Cr—Ta alloy as a magnetic recording layer 4, and carbon as a protective film layer 5 were deposited by sputtering. On the surface of the protective film layer 5, a coating liquid prepared by the following method was coated by the following method, thereby forming a lubricating layer 6.

Preparation of Composition for Coating:

Example Compound 1 having the following structure was dissolved in a fluorine-based solvent (Vertrel, manufactured by Du Pont-Mitsui Fluorochemicals Co., Ltd.; alternatively, HFE-7100□L manufactured by Sumitomo 3M, Ltd.) or acetone in a concentration of 0.2% by mass, thereby preparing coating liquid.

[Formula 25]

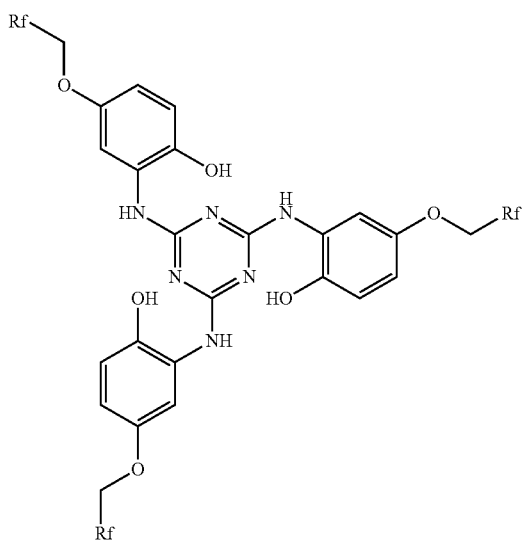

Rf: —$CF_2O(CF_2CF_2O)_2C_2F_5$
(49 wt %)

Formation of Lubricating Layer 6:

The prepared coating liquid was coated on the surface of the protective layer 5 by means of a dip coater (Mini Luber manufactured by Intevac San Jose Technology Corporation) under conditions of dipping rate: 5 mm/sec, dipping time: 60 sec, lifting rate: 1 mm/sec), followed by annealing for 1 hour at 120° C. by using an oven (Clean Oven PVC-210 manufactured by TABAI ESPEC CORPORATION) to form the lubricating layer 6, thereby obtaining a magnetic disk for test.

Example 2

A magnetic disk for test of Example 2 was obtained in the same manner, except that Example Compound 1 was changed to Example Compound 2 having the following structure in the production method of Example 1.

[Formula 26]

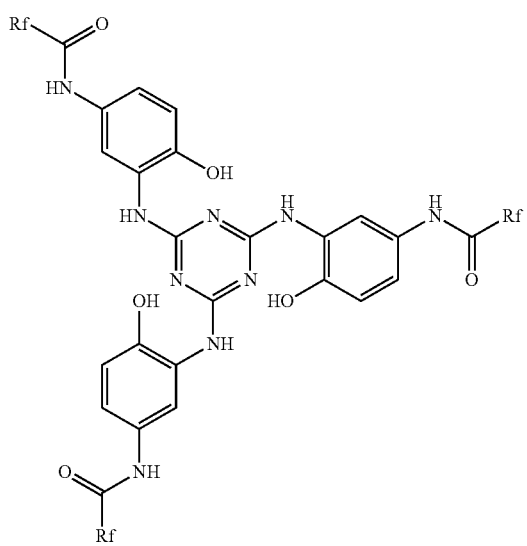

Rf: —$CF_2O(CF_2CF_2O)_2C_2F_5$
(48 wt %)

Example 3

A magnetic disk for test of Example 3 was obtained in the same manner, except that Example Compound 1 was changed to Example Compound 3 having the following structure in the production method of Example 1.

[Formula 27]

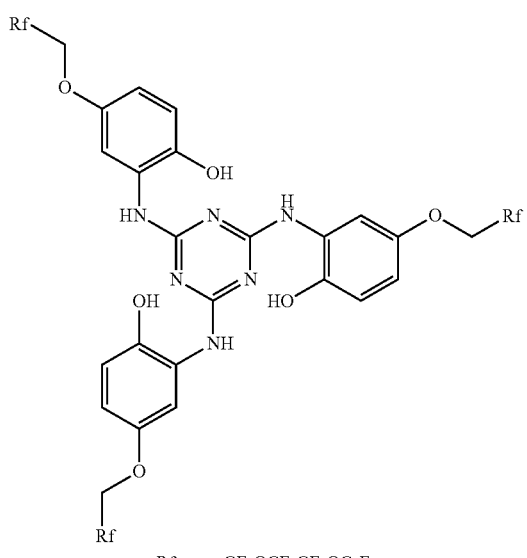

Rf: —$CF_2OCF_2CF_2OC_4F_9$
(51 wt %)

Example 4

A magnetic disk for test of Example 4 was obtained in the same manner, except that Example Compound 1 was changed to Example Compound 4 having the following structure in the production method of Example 1.

[Formula 28]

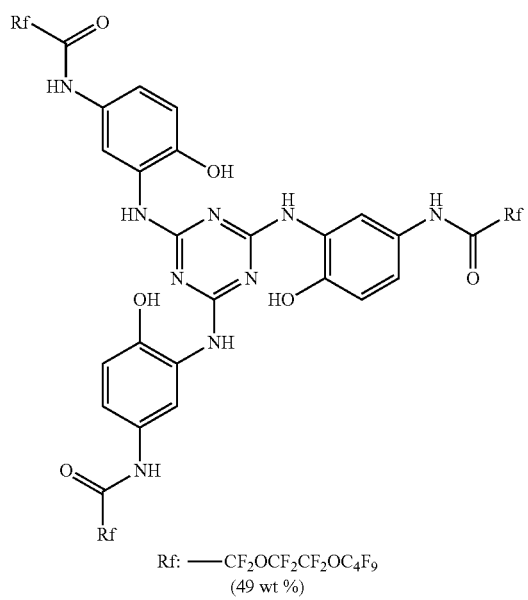

Rf: —CF$_2$OCF$_2$CF$_2$OC$_4$F$_9$
(49 wt %)

[Formula 29]

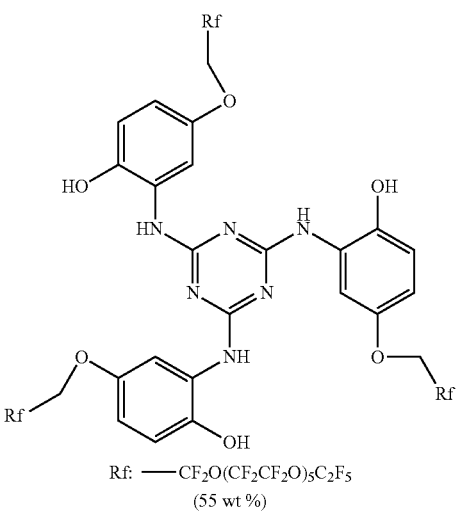

Rf: —CF$_2$O(CF$_2$CF$_2$O)$_5$C$_2$F$_5$
(55 wt %)

Example 6

A magnetic disk for test of Example 6 was obtained in the same manner, except that Example Compound 1 was changed to a compound of Example 6 having the following structure in the production method of Example 1.

[Formula 30]

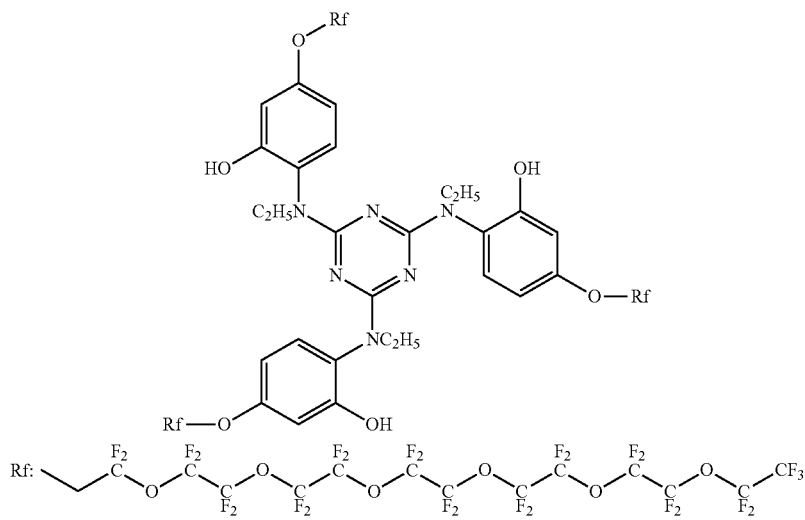

Compound of Example 6

Example 5

A magnetic disk for test of Example 5 was obtained in the same manner, except that Example Compound 1 was changed to Example Compound 17 having the following structure in the production method of Example 1.

Example 7

A magnetic disk for test of Example 7 was obtained in the same manner, except that Example Compound 1 was changed to a compound of Example 7 having the following structure in the production method of Example 1.

[Formula 31]

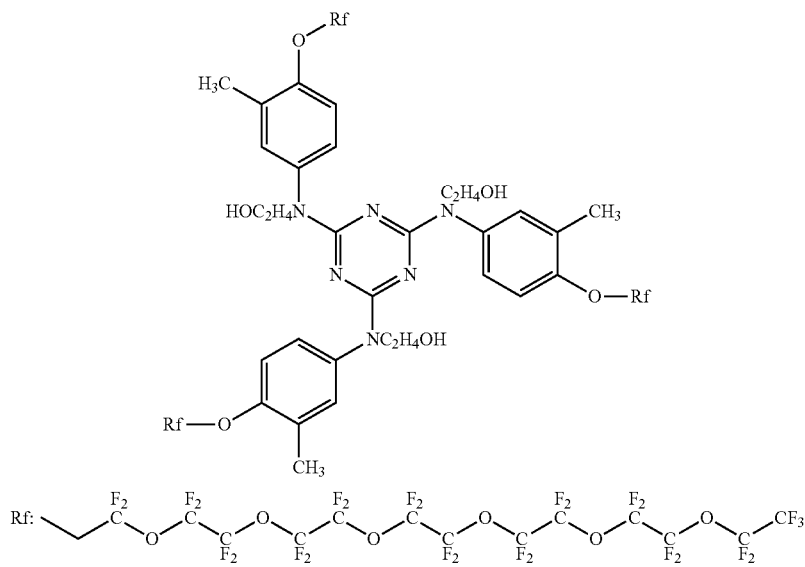

Compound of Example 7

Example 8

A magnetic disk for test of Example 8 was obtained in the same manner, except that Example Compound 1 was changed to a compound of Example 8 having the following structure in the production method of Example 1.

[Formula 32]

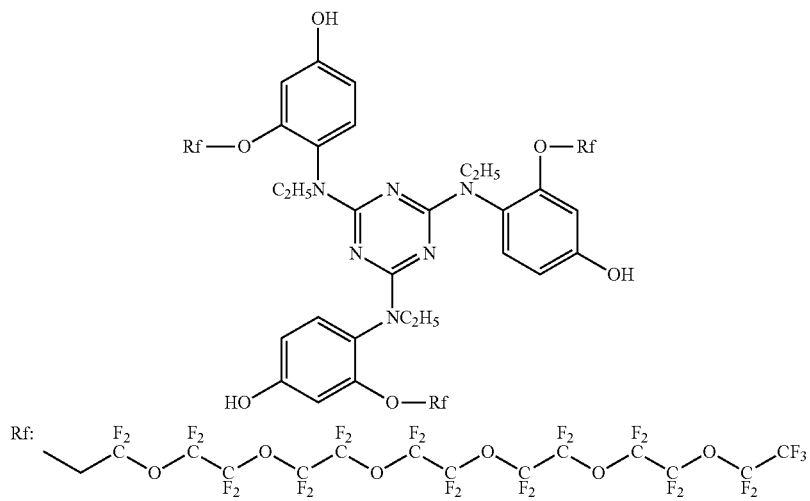

Compound of Example 8

Example 9

A magnetic disk for test of Example 9 was obtained in the same manner, except that Example Compound 1 was changed to a compound of Example 9 in the production method of Example 1.

[Formula 33]

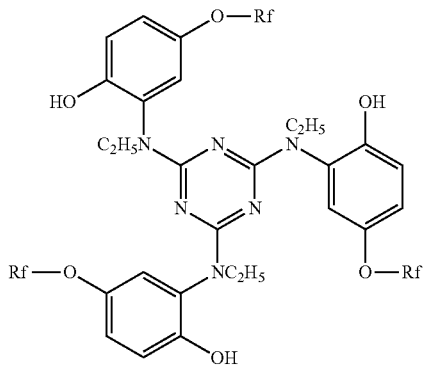

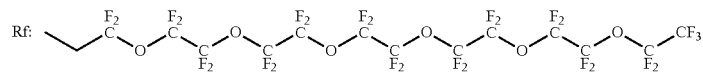

Compound of Example 9

Example 10

A magnetic disk for test of Example 10 was obtained in the same manner, except that Example Compound 1 was changed to a compound of Example 10 in the production method of Example 1.

[Formula 34]

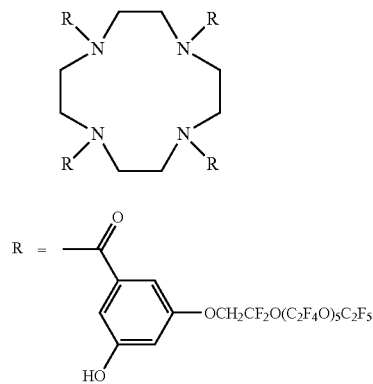

Compound of Example 10

Example 11

A magnetic disk for test of Example 11 was obtained in the same manner, except that Example Compound 1 was changed to Example Compound 5 having the following structure in the production method of Example 1.

[Formula 35]

Rf: —CF$_2$O(CF$_2$CF$_2$O)$_2$C$_2$F$_5$
(43 wt %)

Example 12

A magnetic disk for test of Example 12 was obtained in the same manner, except that Example Compound 1 was changed to Example Compound 8 having the following structure in the production method of Example 1.

[Formula 36]

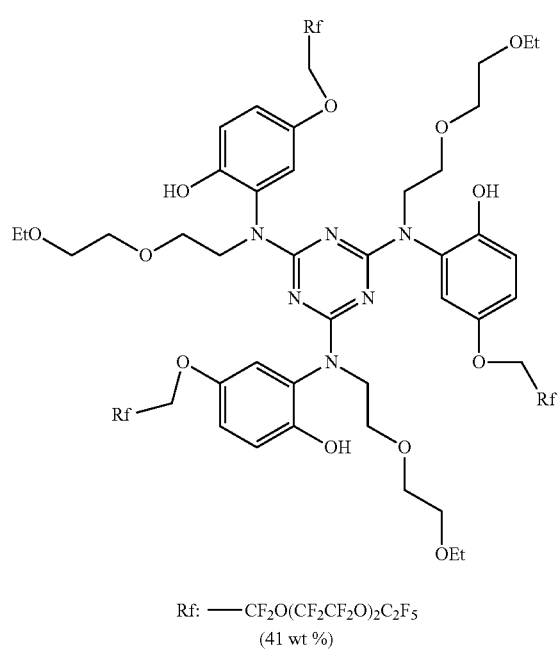

Rf: —CF$_2$O(CF$_2$CF$_2$O)$_2$C$_2$F$_5$
(41 wt %)

Example 13

A magnetic disk for test of Example 13 was obtained in the same manner, except that Example Compound 1 was changed to Example Compound 57 in the production method of Example 1.

[Formula 37]

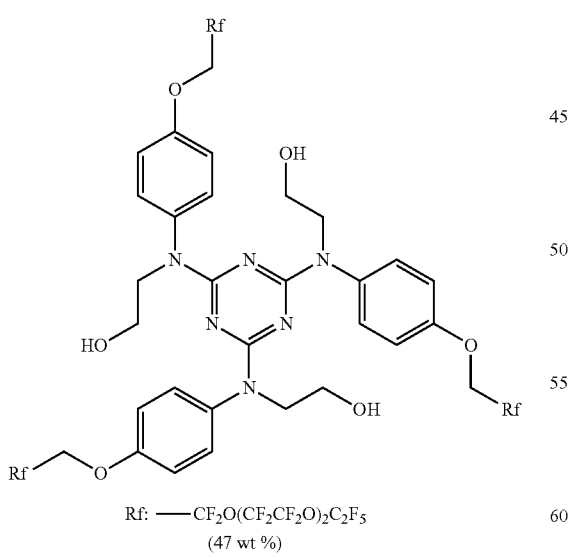

Rf: —CF$_2$O(CF$_2$CF$_2$O)$_2$C$_2$F$_5$
(47 wt %)

Example 14

A magnetic disk for test of Example 14 was obtained in the same manner, except that Example Compound 1 was changed to Example Compound 58 having the following structure in the production method of Example 1.

[Formula 38]

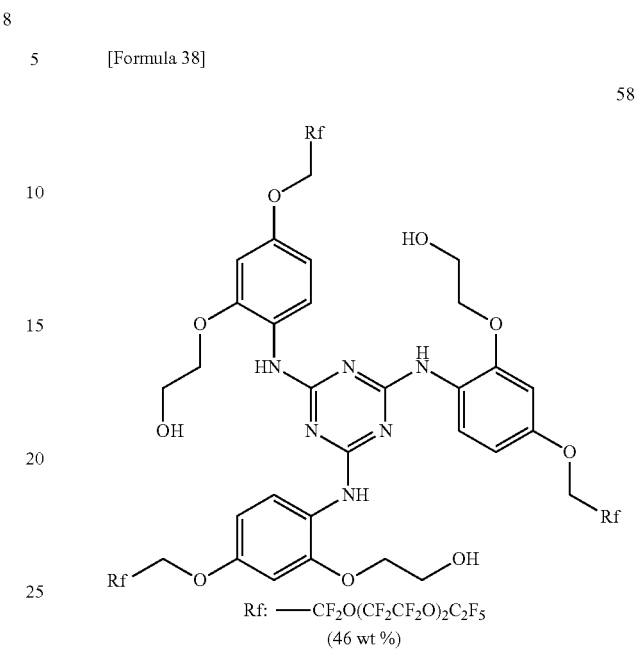

Rf: —CF$_2$O(CF$_2$CF$_2$O)$_2$C$_2$F$_5$
(46 wt %)

Example 15

A magnetic disk for test of Example 15 was obtained in the same manner, except that Example Compound 1 was changed to Example Compound 60 having the following structure in the production method of Example 1.

[Formula 39]

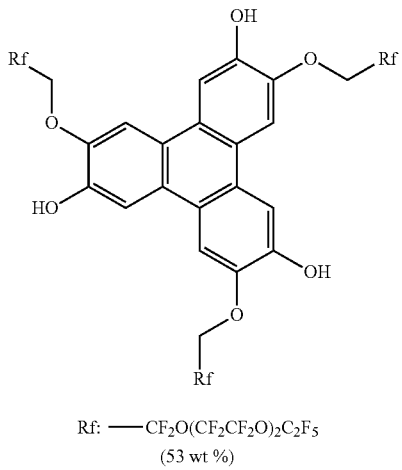

Rf: —CF$_2$O(CF$_2$CF$_2$O)$_2$C$_2$F$_5$
(53 wt %)

Comparative Example 1

A magnetic disk for test of Comparative Example 1 was obtained in the same manner, except that Example Compound 1 was changed to a compound (Fonbrin Z-tetraol, manufactured by Solvay Solexis, Inc.) represented by Formula (5) of the following structure in the production method of Example 1.

[Formula 40]

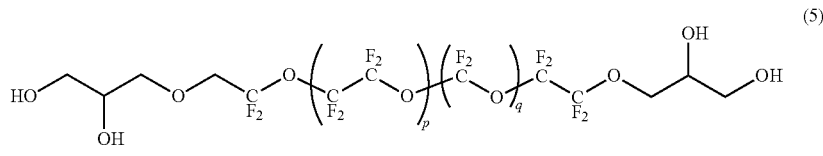

FOMBLIN Z tetraol

Mw = ~2,000

Comparative Example 2

A magnetic disk for test of Comparative Example 2 was obtained in the same manner, except that Example Compound 1 was changed to a compound represented by Formula (6) of the following structure in the production method of Example 1.

[Formula 41]

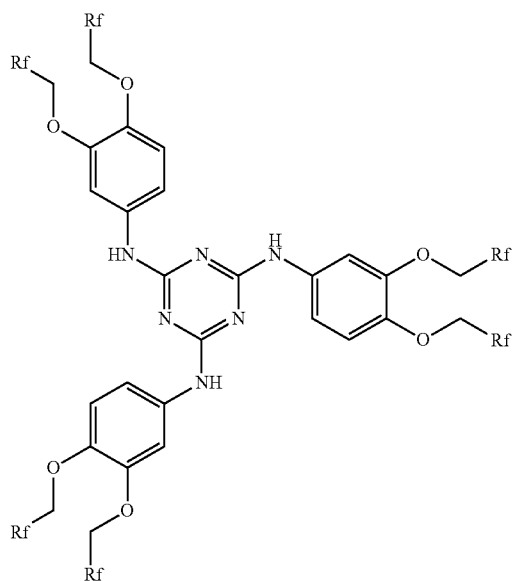

Rf: —CF$_2$O(CF$_2$CF$_2$O)$_2$C$_2$F$_5$

Comparative Example 3

A magnetic disk for test of Comparative Example 3 was obtained in the same manner, except that Example Compound 1 was changed to a compound represented by Formula (7) of the following structure in the production method of Example 1.

[Formula 42]

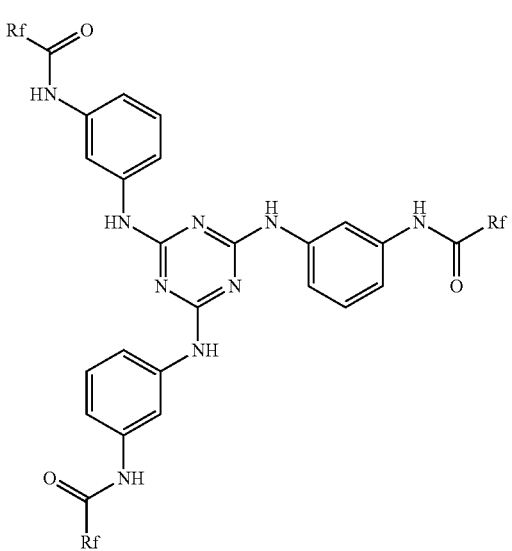

Rf: —CF$_2$OCF$_2$CF$_2$OC$_4$F$_9$

Comparative Example 4

A magnetic disk for test of Comparative Example 4 was obtained in the same manner, except that Example Compound 1 was changed to a compound represented by Formula (8) of the following structure in the production method of Example 1.

[Formula 43]

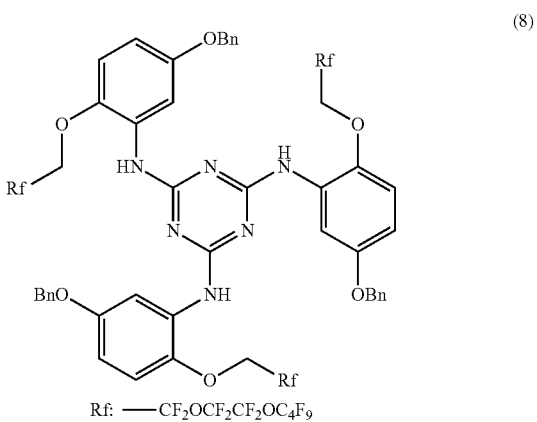

Rf: —CF$_2$OCF$_2$CF$_2$OC$_4$F$_9$

Comparative Example 5

A magnetic disk for test of Comparative Example 5 was obtained in the same manner, except that Example Compound 1 was changed to a compound represented by Formula (9) of the following structure in the production method of Example 1.

[Formula 44]

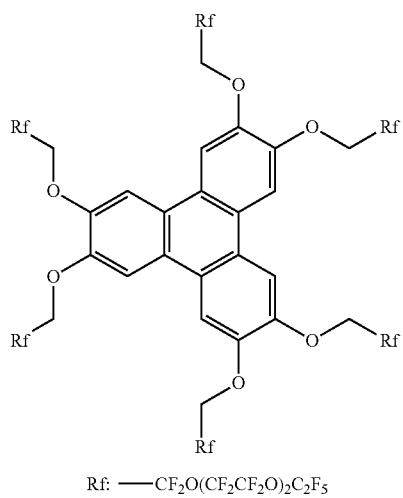

(9)

Rf: —CF$_2$O(CF$_2$CF$_2$O)$_2$C$_2$F$_5$

3. Evaluation
3.-1 Washing

Regarding the respective magnetic disks for test, surface energy measurement and evaluation of the film thickness, coated surface state, and lubricating property was performed respectively before and after washing described below.

After measurement and evaluation of the characteristics described later were performed with respect to the respective magnetic disk for test of Examples 1 to 15 and Comparative Examples 1 to 5, the magnetic disks were dipped into and washed with a fluorine-based solvent (Vertrel, manufactured by Du Pont-Mitsui Fluorochemicals Co., Ltd.; alternatively, HFE-7100□L manufactured by Sumitomo 3M, Ltd.) or an acetone solvent by means of a dip coater (Mini Luber manufactured by Intevac San Jose Technology Corporation), under conditions of a dipping rate: 5 mm/sec, dipping time: 60 sec, and a lifting rate: 1 mm/sec.

Subsequently, the characteristics described later was measured and evaluated in the same manner.

3.-2 Surface Energy Measurement (Evaluation of Adsorptiveness Between Lubricating Layer and Protective Layer)

It is preferable that the lubricating layer and the protective layer be strongly attached to each other, from the viewpoint of prevention of attachment to the head and disproportionation. If the surface energy greatly increases before and after washing, it can be mentioned that adsorptiveness is insufficient. Specifically, the surface energy was measured by the following method.

Regarding the lubricant-coated surface of the respective magnetic disks for test, the value of the surface energy was calculated using a contact angle meter (prop Master 500 manufactured by Kyowa Interface Science Co., LTD., used liquid: water, diiodomethane). It can be mentioned that the lower the surface energy value, the more suitable the lubricant is as a lubricant for the magnetic disk. The surface energy value of a magnetic disk in which the lubricating layer is not formed is about 50 mJ/m$^2$ to 70 mJ/m$^2$.

3.-3 Evaluation of Average Film Thickness

It is preferable that the average film thickness be as thin as possible, from the viewpoint of the reduction in spacing between the head and disk. However, if the film thickness is 1 Å or less, it is determined that the lubricating layer is insufficiently coated. The average film thickness of the lubricating film was measured with respect to the lubricant-coated surface of the respective magnetic disk for test by means of an SRA manufactured by HDI Instrumentation, Inc, and a sensory evaluation was made at 4 levels by the following criteria.

⊚: Ultra-thin film (1 Å to 10 Å)

○: Thin film (10 Å to 20 Å)

Δ: Thick film (20 Å or more)

x: No film (1 Å or less)

3.-4 Evaluation of Coated Surface State

It is preferable that the surface of the magnetic disk be as smooth as possible so as to reduce the false recognition and head collision. Regarding the lubricant-coated surface of the respective magnetic disk for test, the surface roughness was observed by means of visual confirmation, a laser surface inspection device (SRA-10,000 manufactured by HDI Instrumentation, Inc,), and AFM (Demension 3100 AFM manufactured by Veeco Instruments Inc.), and a sensory evaluation was made at 3 levels by the following criteria. Here, a film thickness of 1 Å or less was not evaluated.

⊚: No surface unevenness was observed by laser inspection and AFM.

○: No unevenness was observed by visual confirmation. Slight concavity and convexity were observed by laser inspection and AFM.

Δ: Unevenness was observed by visual confirmation.

3.-5 Evaluation of Lubricating Property

It is preferable that the lubricating property be as high as possible so as to prevent the disk abrasion at the time of head collision. First, the respective magnetic disks for test were rotated by a spin stand, and a reading head was caused to float. Thereafter, atmospheric pressure was reduced until head-disk contact was caused in the disk-fixed radius, and the head and disk were forcedly caused to slide on each other for a certain time. Subsequently, the disk surface was observed after the test, and a sensory evaluation was made at 3 levels by the following criteria. The used evaluation device was a HDF tester manufactured by Kubota Comps Corporation.

⊚: No scratching was caused by 10 min of sliding.

○: Scratching was caused by 5 min to 10 min of sliding.

Δ: Scratching was caused by 5 min or less of sliding.

The above measurement results and evaluation results are summarized in the following table.

TABLE 1

| Example | Before Washing Treatment | | | | After Washing Treatment | | | |
|---|---|---|---|---|---|---|---|---|
| | Surface Energy | Average Film Thickness | Coated Surface State | Lubricating Property | Surface Energy | Average Film Thickness | Coated Surface State | Lubricating Property |
| Example 1 | 20 mN/m | ○ | Δ | ⊚ | 20 mN/m | ⊚ | ○ | ○ |
| Example 2 | 13 mN/m | Δ | Δ | ⊚ | 13 mN/m | ○ | ○ | ○ |
| Example 3 | 20 mN/m | ⊚ | ○ | ⊚ | 20 mN/m | ⊚ | ○ | ○ |
| Example 4 | 14 mN/m | Δ | Δ | ⊚ | 15 mN/m | ⊚ | ○ | ○ |
| Example 5 | 12 mN/m | ○ | ○ | ⊚ | 12 mN/m | ⊚ | ⊚ | ⊚ |
| Example 6 | 14 mN/m | ○ | ○ | ⊚ | 15 mN/m | ⊚ | ⊚ | ⊚ |
| Example 7 | 13 mN/m | ○ | ○ | ⊚ | 14 mN/m | ⊚ | ⊚ | ⊚ |
| Example 8 | 14 mN/m | ○ | ○ | ⊚ | 15 mN/m | ⊚ | ⊚ | ⊚ |
| Example 9 | 14 mN/m | ○ | ○ | ⊚ | 15 mN/m | ⊚ | ⊚ | ⊚ |
| Example 10 | 13 mN/m | ○ | ○ | ⊚ | 14 mN/m | ⊚ | ⊚ | ⊚ |
| Example 11 | 15 mN/m | ○ | ○ | ⊚ | 15 mN/m | ⊚ | ⊚ | ○ |
| Example 12 | 14 mN/m | ○ | ○ | ⊚ | 15 mN/m | ⊚ | ⊚ | ○ |
| Example 13 | 14 mN/m | ○ | ○ | ⊚ | 14 mN/m | ⊚ | ⊚ | ○ |
| Example 14 | 14 mN/m | ○ | ○ | ⊚ | 14 mN/m | ⊚ | ⊚ | ○ |
| Example 15 | 12 mN/m | ○ | ○ | ⊚ | 15 mN/m | ⊚ | ⊚ | ○ |
| Comparative Example 1 | 15 mN/m | ○ | ⊚ | ○ | 16 mN/m | ○ | ⊚ | Δ |
| Comparative Example 2 | 15 mN/m | Δ | Δ | Δ | 33 mN/m | X | — | Δ |
| Comparative Example 3 | 58 mN/m | ○ | Δ | Δ | 68 mN/m | X | — | Δ |
| Comparative Example 4 | 17 mN/m | Δ | Δ | Δ | 42 mN/m | X | — | Δ |
| Comparative Example 5 | 57 mN/m | Δ | Δ | Δ | 62 mN/m | X | — | Δ |

An RAS device was installed in a sample chamber of a complete vacuum FT-IR spectrometer "FT-IR6400" manufactured by JASCO Corporation, whereby an IR spectrum was measured with respect to the respective magnetic disks.

As a result, it was confirmed that all of the magnetic disks for test of examples showed a sharp peak attributed to a stretching vibration of $CF_3$ in a range of 1255 $cm^{-1}$ to 1265 $cm^{-1}$. This result suggests that in the example compound that is on the protective layer surface, the PFPE chain is oriented vertically with respect to the layer surface.

4. Evaluation of Orientation

Figure 2:
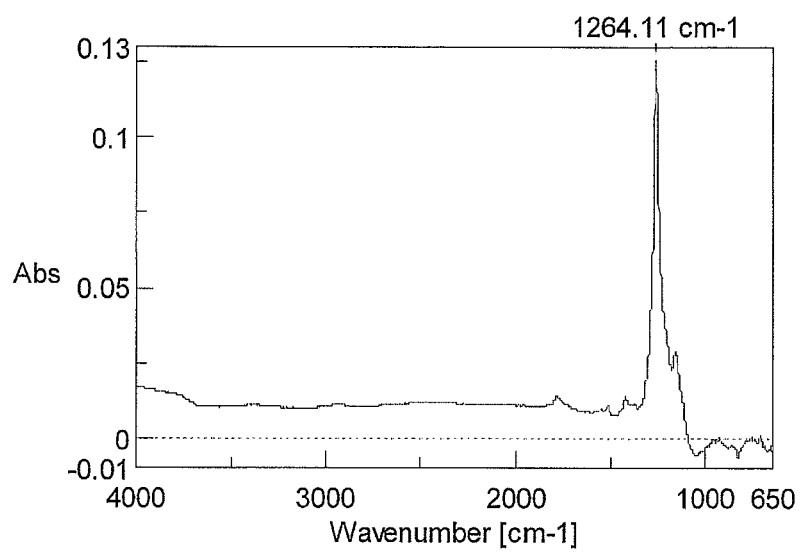
FIG. 2 is a measurement result in the form of a FT-IR RAS spectrum of an LB film of an example compound of Formula (1).
Figure 3:
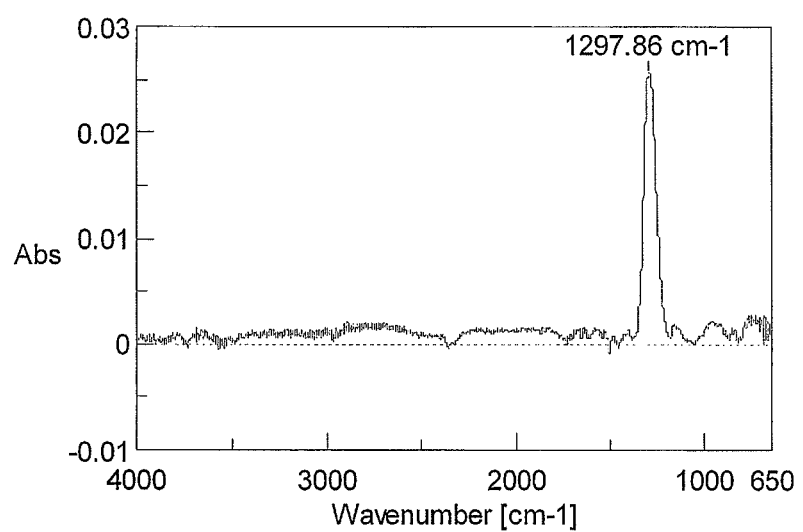
FIG. 3 is a measurement result in the form of a FT-IR RAS spectrum of an LB film of FOMBLIN Z-TETRAOL.

Regarding each of a disk-like compound having PFPE chains in a trianilino-substituted 1,3,5-triazine ring, and a disk-like compound having PFPE chains in a triphenylene ring, which were the example compounds of Formula (1) shown below; and "FOMBLIN Z-DOL" and "FOMBLIN Z-TETRAOL" having chain-like PFPE chains, a FT-IR RAS spectrum was measured using samples which were obtained by skimming the LB monolayer film thereof onto diamond-like carbon. Regarding the former two compounds, a sharp peak of a stretching vibration of $CF_3$ was confirmed at 1260 $cm^{-1}$, and regarding the latter two compounds, a slightly broad stretching vibration of $CF_2$ was confirmed at 1298 $cm^{-1}$. Since the RAS spectrum uses a polarized spectrum of IR, only the vibration of bonds in a vertical direction with respect to the substrate surface is detected. Accordingly, from the results, it is confirmed that the PFPE chains of the former two compounds are oriented vertically with respect to the substrate surface, and that the PFPE chains of the latter two compounds are oriented horizontally with respect to the substrate surface. FIGS. 2 and 3 show the measurement results of the FT-IR RAS spectrum of the LB film of the disk-like compound that has PFPE chains in the trianilino-substituted 1,3,5-triazine ring, and FIG. 3 shows the measurement results of the FT-IR RAS spectrum of the LB film of "FOMBLIN Z-TETRAOL", respectively.

[Formula 45]

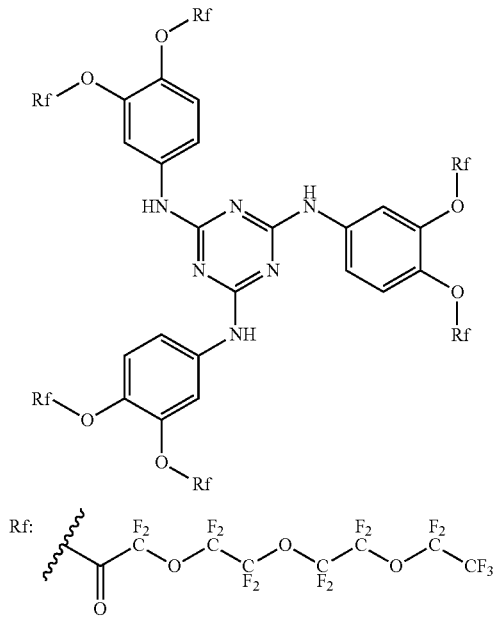

5. Production Example by Spin Coating Method and Evaluation

Magnetic disks for test were produced in the same manner as Examples 1 to 15, except that the lubricating film was formed by a spin coating method instead of a dip coating method in the production method of the Examples 1 to 15. These magnetic disks for test were evaluated in terms of the film thickness, coated surface state, and lubricating property, in the same manner as Examples 1 to 15, and as a result, all of the disks were excellent to the same degree.

A magnetic disk for test was produced in the same manner as Comparative Example 1, except that the lubricating film was formed by a spin coating method instead of a dip coating method in the production method of the Comparative example 1. This magnetic disk for test was evaluated in terms of the film thickness, coated surface state, and lubricating property as described above, and as a result, the coated surface state of this magnetic disk was worsened compared to Comparative Example 1.

From these results, it is possible to understand that the lubricant composition of the invention can form a film that shows an excellent surface state regardless of the coating method.

6. Production of Head Slider and Evaluation

6.-1 Production of Head Slider

The example compound of the following Formula (1) was dissolved in a fluorine-based solvent (Vertrel manufactured by DuPont-Mitsui Fluorochemicals Co., Ltd.) in a concentration of 0.05% by mass, thereby preparing a coating liquid.

[Formula 46]

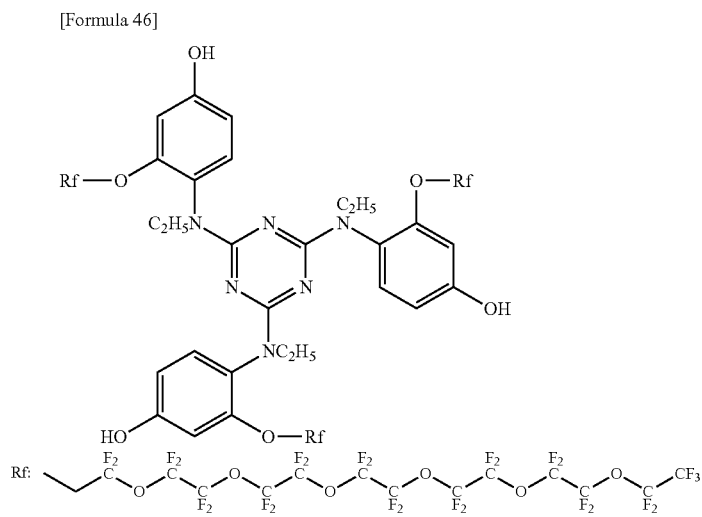

Compound of Example 8

This coating liquid was coated on a negative pressure pico-slider by a dip coating method. Specifically, the slider was dipped into the coating liquid for 1 minute, and coating was performed at a lifting rate of 1 mm/sec, followed by annealing for 1 hour at 120° C. Subsequently, the resultant was washed by being dipped into a fluorine-based solvent "HFE-7100□L" (manufactured by Sumitomo 3M, Ltd.) for 1 minute. In this manner, a head slider having a lubricating film was produced and denoted as Example 16.

Coating liquid was prepared in the same manner, except that the example compound of Formula (1) was changed to "Z-Tetraol" manufactured by Solvay Solexis, Inc., and that the concentration was set to 0.2% by mass, in the preparation of coating liquid described above. A lubricating film was formed on the head slider surface in the same manner as described above, except that this coating liquid was used. The resultant was denoted as Comparative Example 6.

In addition, as Comparative Example 7, a head slider in which the lubricating film was not formed was also prepared.

6.-2 Evaluation 2.5 inch magnetic media in which a lubricating film was formed by coating of "Z-Tetraol" were rotated at 5400 PRM in a pressure reduction spin stand, and the respective sliders of Example 16 and Comparative Examples 6 and 7 were loaded by ramp load and caused to seek a radial position at 22 mm. From when the head floated stably, the chamber pressure was reduced. When an AE sensor detected a moment in which flying height decreased, and the head contacted the media, the pressure was returned to atmospheric pressure, and the fly height was raised.

The pressure at the time when the AE detects the contact is called TDP (touch down pressure), and the pressure at the time when the AE is stabilized due to the return to the atmospheric pressure is called TOP (take off pressure). The smaller these pressures, the larger the head-disk clearance. The friction force caused during the contact was measured using a friction gauge that was installed in a head pivot portion. This operation was repeated three times, and the average thereof was calculated.

Head after the contact was observed by a microscope to observe the attachment of the lubricant to the head.

The results are shown in the following Table.

TABLE 2

| Material of Lubricating Film | | Friction (gf) | TDP (torr) | Head Contamination |
|---|---|---|---|---|
| Example 16 | Compound of Formula (1) | $\circ(\leq 3$ gf) | 402 | $\circ$ |
| Comparative Example 6 | Z-Tetraol | $\circ(\leq 3$ gf) | 400 | $\Delta$ |
| Comparative Example 7 | — | $x(\geq 3.5$ gf) | 401 | x |

Head contamination ○: No contamination, Δ: Contamination at 1 to 2 positions, x; Contamination at 3 or more positions From the results shown in the above Table, it was confirmed that the head slider having a lubricating film that was formed using the compound of Formula (1) showed low frictional property and caused less head contamination.

REFERENCE SIGNS LIST

1 substrate
2 hard base layer
3 base film layer
4 magnetic recording layer
5 protective film layer
6 lubricating layer

The invention claimed is:

1. A lubricant composition comprising at least one kind of the a compound represented by the following Formula (3):

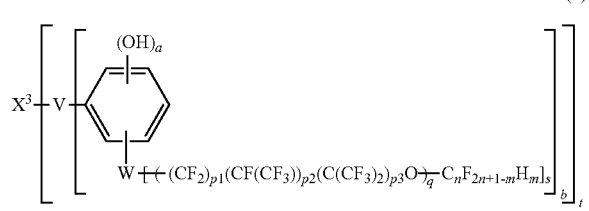

(3)

wherein $X^3$ represents a cyclic group selected from the group consisting of a triphenylene ring, a perylene ring, a triazine ring, a phthalocyanine ring, a porphyrin ring, a corrole ring, a coronene ring and an aza-crown ring, which may be substituted; V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4, provided that a+b is 2 to 5, provided that there is no limitation on the binding order of $-(CF_2)_{p1}-$, $-(CFCF_3)_{p2}-$, and $-(C(CF_3)_2)_{p3}$ which constitute $-((CF_2)_{p1}(CFCF_3)_{p2}(C(CF_3)_2)_{p3}O)-$ in a polyfluoride polyether chain in the formula, and $-((CF_2)_{p1}(CFCF_3)_{p2}(C(CF_3)_2)_{p3}O)-$ means a group in which a perfluoroalkylene unit selected from $-CF_2)_{p1}-$, $-(CFCF_3)_{p2}-$, and $-(C(CF_3)_2)_{p3}-$ and an oxygen atom are randomly distributed;

when q is 2 or greater, a plurality of $-((CF_2)_{p1}(CFCF_3)_{p2}(C(CF_3)_2)_{p3}O)-$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.

2. The lubricant composition according to claim 1, wherein $X^3$ represents a cyclic group selected from the group consisting of a triphenylene ring, a perylene ring, a triazine ring, a phthalocyanine ring, a porphyrin ring, a corrole ring, and a coronene ring, which may be substituted.

3. The lubricant composition according to claim 1, wherein at least one kind of the compound represented by Formula (3) is a compound represented by the following Formula (4):

wherein V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4, provided that a+b is 2 to 5; R represents an arbitrary substituent; and c represents a real number of 0 to 1, provided that c+t=3, and there is no limitation on the binding order of $-(CF_2)_{p1}-$, $-(CFCF_3)_{p2}-$, and $-(C(CF_3)_2)_{p3}$ which constitute $-((CF_2)_{p1}(CFCF_3)_{p2}(C(CF_3)_2)_{p3}O)-$ in a polyfluoride polyether chain in the formula, and $-((CF_2)_{p1}(CFCF_3)_{p2}(C(CF_3)_2)_{p3}O)-$ means a group in which a perfluoroalkylene unit selected from $-(CF_2)_{p1}-$, $-(CFCF_3)_{p2}-$, and $-(C(CF_3)_2)_{p3}-$ and an oxygen atom are randomly distributed;

when q is 2 or greater, a plurality of $-((CF_2)_{p1}(CFCF_3)_{p2}(C(CF_3)_2)_{p3}O)-$ may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.

4. The lubricant composition according to claim 1, wherein W is a divalent linking group including an imino group (NH or NR (R is a substituent)), an alkylene group with 1 to 20 carbon atoms (here, one carbon atom or two or more carbon atoms that are not adjacent to each other may be substituted with an oxygen atom), a carbonyl group (C=O), an oxy group (O), and a combination of 1 or more kinds selected from these groups.

5. The lubricant composition according to claim 1, wherein V is a single bond, an oxy group, —NH—, —N(alkyl)-, —N(substituted alkyl), a carbonyl group, a sulfonyl group, an alkylene group, or a combination thereof.

6. The lubricant composition according to claim 1, wherein at least one polyfluoride polyether chain in the formula is $-(OCF_2CF_2)_kOC_nF_{2n+1}$ (here, k+n is 8 or less, and k is 6 or less).

7. The lubricant composition according to claim 1, wherein a chain configured with at least one of —W and polyfluoride polyether chain in the formula is $-OCH_2CF_2-(OCF_2CF_2)_kOC_nF_{2n+1}$ (here, k+n is 8 or less, and k is 6 or less).

8. A lubricant of a disk for a magnetic recording medium comprising the lubricant composition according to claim 1.

9. A film including the lubricant composition according to claim 1.

10. The film according to claim 9, which is formed by a dip coating method, a spin coating method, or vacuum vapor deposition.

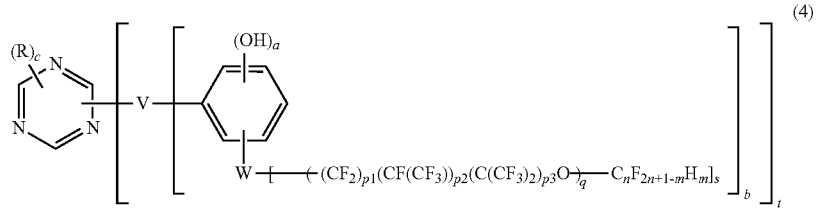

(4)

11. A laminate comprising:
a substrate in which at least a portion of the surface thereof includes carbon as a main material; and
the film according to claim 9 on the substrate.

12. A magnetic recording medium at least comprising:
a magnetic layer; and
the film according to claim 9.

13. The magnetic recording medium according to claim 12, further comprising a protective layer between the magnetic layer and the film.

14. A head slider provided with a magnetic head, comprising the film according to claim 9 on at least a portion of the surface thereof.

15. A magnetic recording device comprising the magnetic recording medium according to claim 12.

16. A compound represented by the following Formula (3):

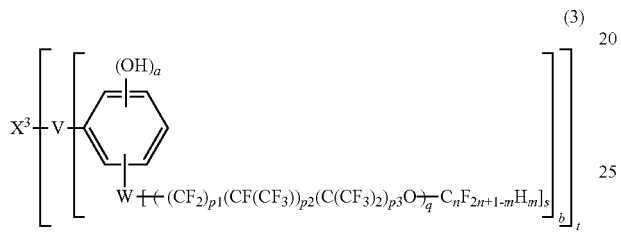

(3)

wherein $X^3$ represents a cyclic group that may be substituted; V and W independently represent a single bond or a linking group having a valency of 2 or more; p1 represents a real number of 1 to 4; p2 and p3 independently represent a real number of 0 to 4; q represents a real number of 1 to 30; n represents a real number of 1 to 10; m represents a real number of 0 to 1; s represents a real number of 1 or greater; t represents a real number of 2 or greater; and a and b independently represent a real number of 1 to 4, provided that a+b is 2 to 5, provided that there is no limitation on the binding order of —$(CF_2)_{p1}$—, —$(CFCF_3)_{p2}$—, and —$(C(CF_3)_2)_{p3}$— which constitute —$((CF_2)_{p1}(CFCF_3)_{p2}(C(CF_3)_2)_{p3}O)$— in a polyfluoride polyether chain in the formula, and —$((CF_2)_{p1}(CFCF_3)_{p2}(C(CF_3)_2)_{p3}O)$— means a group in which a perfluoroalkylene unit selected from —$(CF_2)_{p1}$—, —$(CFCF_3)_{p2}$—, and —$(C(CF_3)_2)_{p3}$— and an oxygen atom are randomly distributed;

when q is 2 or greater, a plurality of —$((CF_2)_{p1}(CFCF_3)_{p2}(C(CF_3)_2)_{p3}O)$— may be the same as or different from each other, when s is 2 or greater, a plurality of n, m, and q may be independently the same as or different from each other, when b is 2 or greater, a plurality of s and W may be independently the same as or different from each other, and when t is 2 or greater, a plurality of b and V may be independently the same as or different from each other.

17. The compound according to claim 16,
wherein $X^3$ is a substituted or unsubstituted triazine ring residue, a substituted or unsubstituted triphenylene residue, or a residue of an aza-crown ether ring.

18. A magnetic recording device comprising the head slider according to claim 14.

19. A lubricant composition comprising at least one kind of a compound represented by the Formula (3) according to claim 16.

* * * * *